US009908848B2

(12) United States Patent
Piomelli et al.

(10) Patent No.: US 9,908,848 B2
(45) Date of Patent: *Mar. 6, 2018

(54) AMIDE DERIVATIVES OF LACTAM BASED N-ACYLETHANOLAMINE ACID AMIDASE (NAAA) INHIBITORS

(71) Applicants: The Regents of the University of California, Oakland, CA (US); Universita Degli Studi Di Urbino "Carlo Bo", Urbino (IT); Fondazione Istituto Italiano di Technologia, Genoa (IT); Universita Degli Studi Di Parma, Parma (IT)

(72) Inventors: Daniele Piomelli, Irvine, CA (US); Marco Mor, Ghedi (IT); Giorgio Tarzia, Petriano (IT); Fabio Bertozzi, Genoa (IT); Andrea Nuzzi, Davoli (IT); Annalisa Fiasella, Pisa (IT); Tiziano Bandiera, Gambolo (IT); Angelo Mario Reggiani, Recco (IT)

(73) Assignees: The Regents of the University of California, Oakland, CA (US); Fondazione Istituto Italiano di Tecnologia, Genoa (IT); Universita Degli Studi di Urbino "Carlo Bo", Urbino (IT); Universita Degli Studi di Parma, Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/853,697

(22) Filed: Sep. 14, 2015

(65) Prior Publication Data

US 2016/0068483 A1 Mar. 10, 2016

Related U.S. Application Data

(63) Continuation of application No. PCT/US2014/029007, filed on Mar. 14, 2014.

(60) Provisional application No. 61/799,470, filed on Mar. 15, 2013.

(51) Int. Cl.
 *C07D 205/085* (2006.01)
(52) U.S. Cl.
 CPC .............................. *C07D 205/085* (2013.01)
(58) Field of Classification Search
 None
 See application file for complete search history.

(56) References Cited

U.S. PATENT DOCUMENTS

| 4,207,234 A * | 6/1980 | Kamiya ............... C07D 473/00 540/363 |
| 4,550,105 A | 10/1985 | Matsuo et al. |
| 4,584,132 A * | 4/1986 | Albrecht ............... C07F 9/5683 514/85 |
| 4,665,171 A | 5/1987 | Evans et al. |
| 4,683,303 A * | 7/1987 | Pfaendler ............ C07D 205/08 540/357 |
| 4,831,130 A | 5/1989 | Albrecht et al. |
| 4,870,169 A | 9/1989 | Evans et al. |
| 4,931,556 A | 6/1990 | Boyer et al. |
| 5,137,884 A | 8/1992 | Andrus et al. |
| 5,260,310 A | 11/1993 | Derungs et al. |
| 5,646,275 A | 7/1997 | Gardner et al. |
| 5,962,012 A | 10/1999 | Lin et al. |
| 6,261,595 B1 | 7/2001 | Stanley et al. |
| 6,358,978 B1 | 3/2002 | Ritzeler et al. |
| 9,321,743 B2 | 4/2016 | Piomelli et al. |
| 9,353,075 B2 | 5/2016 | Piomelli et al. |
| 2005/0131032 A1 | 6/2005 | Sit et al. |
| 2006/0281778 A1 | 12/2006 | Tagat et al. |
| 2007/0155747 A1 | 7/2007 | Dasse et al. |
| 2008/0050336 A1 | 2/2008 | Bachand et al. |
| 2009/0054526 A1 | 2/2009 | Hansen et al. |

(Continued)

FOREIGN PATENT DOCUMENTS

| EP | 0 742 223 A1 | 11/1996 |
| EP | 0 742 223 B1 | 11/1996 |

(Continued)

OTHER PUBLICATIONS

Banker, Gilbert. Modern Pharmaceutics 3rd ed. Marcel Dekker, Inc. New York, 1996.*
Sliwa, Aline. Chem. Asian J. 7 (2012) 425-434.*
Cainelli, Gianfranco. Tetrahedron: Asymmetry, vol. 8. No. 19 (1997) 3231-3235.*
Patani, George. Chem. Rev. 96 (1996) 3147-3176.*
Berdyshev, E. et al. (1998). "Effects of Cannabinoid Receptor Ligands on LPS-Induced Pulmonary Inflammation in Mice," Life Sciences 63(8): PL125-129.
Calignano, A. et al. (Jul. 16, 1998). "Control of pain initiation by endogenous cannabinoids," nature 394(6690):277-281.
Calignano, A. et al. (May 11, 2001). "Antinociceptive activity of the endogenous fatty acid amide, palmitylethanolamide," *Eur J Pharmacol* 419(2-3):191-198.

(Continued)

*Primary Examiner* — Deepak R Rao
*Assistant Examiner* — Laura M Daniel
(74) *Attorney, Agent, or Firm* — Zachary L. Terranova; Mintz, Levin, Cohn, Ferris, Glovsky and Popeo, P.C.

(57) ABSTRACT

Described herein are compounds and pharmaceutical compositions which inhibit N-acylethanolamine acid amidase (NAAA). Described herein are methods for synthesizing the compounds set forth herein and methods for formulating these compounds as pharmaceutical compositions which include these compounds. Also described herein are methods of inhibiting NAAA in order to sustain the levels of palmitoylethanolamide (PEA) and other N-acylethanolamines (NAE) that are substrates for NAAA, in conditions characterized by reduced concentrations of NAE. Also, described here are methods of treating and ameliorating pain, inflammation, inflammatory diseases, and other disorders in which modulation of fatty acid ethanolamides is clinically or therapeutically relevant or in which decreased levels of NAE are associated with the disorder.

8 Claims, 1 Drawing Sheet

(56) References Cited

U.S. PATENT DOCUMENTS

| | | |
|---|---|---|
| 2010/0311711 A1 | 12/2010 | Piomelli et al. |
| 2013/0281490 A1 | 10/2013 | Piomelli et al. |
| 2014/0094508 A1 | 4/2014 | Piomelli et al. |
| 2016/0068482 A1 | 3/2016 | Piomelli et al. |
| 2016/0235707 A1 | 8/2016 | Piomelli et al. |
| 2016/0256432 A1 | 9/2016 | Piomelli et al. |

FOREIGN PATENT DOCUMENTS

| | | |
|---|---|---|
| WO | WO-2009/049238 A1 | 4/2009 |
| WO | WO-2011/082285 A1 | 7/2011 |
| WO | WO-2013/078430 A1 | 5/2013 |
| WO | WO-2014/144547 A2 | 9/2014 |
| WO | WO-2014/144547 A3 | 9/2014 |
| WO | WO-2014/144836 A2 | 9/2014 |
| WO | WO-2014/144836 A3 | 9/2014 |

OTHER PUBLICATIONS

D'Agostino, G. et al. (Sep. 2007, e-published Jun. 12, 2007). "Acute intracerebroventricular administration of palmitoylethanolamide, an endogenous peroxisome proliferator-activated receptor-alpha agonist, modulates carrageenan-induced paw edema in mice," *J Pharmacol Exp Ther* 322(3):1137-1143.

Fiasella, A. et al. (Jul. 2014, e-published May 14, 2014). "3-Aminoazetidin-2-one derivatives as N-acylethanolamine acid amidase (NAAA) inhibitors suitable for systemic administration," *ChemMedChem* 9(7):1602-1614.

Fleisher, D. et al. (May 22, 1996). "Improved Oral Drug Delivery: Solubility Limitations Overcome by the Use of Prodrugs," *Advanced Drug Delivery Reviews* 19(2):115-130.

International Search Report dated Sep. 29, 2014, for PCT Application No. PCT/US2014/029007, filed Mar. 14, 2014, 4 pages.

Kemeny, L. et al. (2007, e-published Jan. 17, 2007). "Endogenous phospholipid metabolite containing topical product inhibits ultraviolet light-induced inflammation and DNA damage in human skin," *Skin Pharmacol Physiol* 20(3):155-161.

Lo Verme, J. et al. (Jan. 2005, e-published Oct. 1, 2004). "The nuclear receptor peroxisome proliferator-activated receptor-alpha mediates the anti-inflammatory actions of palmitoylethanolamide," *Mol Pharmacol* 67(1):15-19.

Lo Verme, J. et al. (Dec. 2006, e-published Sep. 22, 2006). "Rapid broad-spectrum analgesia through activation of peroxisome proliferator-activated receptor-alpha," *J Pharmacol Exp Ther* 319(3):1051-1061.

Mazzari, s. et al. (Apr. 1996). "N-(2-hydroxyethyl)hexadecanamide is orally active in reducing edema formation and inflammatory hyperalgesia by down-modulating mast cell activation," *Eur J Pharmacol* 300(3):227-236.

Solorzano, C. et al. (Dec. 8, 2009, e-published Nov. 19, 2009). "Selective N-acylethanolamine-hydrolyzing acid amidase inhibition reveals a key role for endogenous palmitoylethanolamide in inflammation," *PNAS USA* 106(49):20966-20971.

Solorzano, C. et al. (Aug. 12, 2010). "Synthesis and structure-activity relationships of N-(2-oxo-3-oxetanyl)amides as N-acylethanolamine-hydrolyzing acid amidase inhibitors,"*J Med Chem* 53(15):5770-5781.

Written Opinion dated Sep. 29, 2014, for PCT Application No. PCT/US2014/029007, filed Mar. 14, 2014, 6 pages.

Armirotti, Andrea et al., "β-Lactones Inhibit N-acylethanolamine Acid Amidase by S-Acylation of the Catalytic N-Terminal Cysteine," *ACS Medicinal Chemistry Letters (ACS)*, 2012, vol. 3, No. 5, pp. 422-426.

Astarita, G. et al., "Pharmacological Characterization of Hydrolysis-Resistant Analogs of Oleoylethanolamide with Potent Anorexiant Properties," *The Journal of Pharmacology and Experimental Therapeutics*, vol. 318, No. 2, received Mar. 24, 2006, accepted May 12, 2006.

Beauve, C. et al. (1999). "Synthesis, Reactivity and Biochemical Evaluation of 1,3-Substituted Azetidin-2-ones as Enzyme Inhibitors," *Tetrahedron* 55:13301-13320.

Chalker, J.M. et al. (Nov. 18, 2009). "A convenient catalyst for aqueous and protein Suzuki-Miyaura cross-coupling," *J Am Chem Soc* 131(45):16346-16347.

Dias et al., "Antimicrobial properties of highly fluorinated silver (I) tis (pyrazoili) borates," *Journal of Inorganic Biochemistry*, 2006, vol. 100, pp. 158-160.

Duranti et al., "N-(2-Oxo-3-oxetanyl)carbamic Acid Esters as N-Acylethanolamine Acid Amidase Inhibitors: Synthesis and Structure-Activity and Structure—Property Relationships," *Journal of Medicinal Chemistry*, May 2012, pp. A-M.

Evans, D.A. et al. (1985). "The Asymmetric Synthesis of β-Lactam Antibiotics- I. Application of Chiral Oxazolidones in the Staudinger Reaction," *Tetrahedron Letters* 26:3783.

He, G. et al. (May 23, 2011, e-published Apr. 27, 2011). "A practical strategy for the structural diversification of aliphatic scaffolds through the palladium-catalyzed picolinamide-directed remote functionalization of unactivated C(sp3)-H bonds," *Angewandte Chemie Int. Ed.* 50(22):5192-5196.

Higashibayashi, Shuhei et al., Synthetic studies on thiostrepton family of peptide antibiotics: synthesis of the pentapeptide segment containing dihydroxyisoleucine, thiazoline and dehydroamino acid, *Tetrahedron Letters* (Elsevier B.V.), 2004, vol. 45, No. 19, pp. 3707-3712.

Holt et al., "Inhibition of fatty acid amide hydrolase, a key endocannabinoid metabolizing enzyme, by analogues of ibuprofen and indomethacin," *Eur J Pharmacol.*, Jun. 2007, 565(1-3):26-36, Epub Mar. 2007.

International Search Report, dated Dec. 17, 2008, for International Application No. PCT/US2008/079621, filed Oct. 10, 2008, 1 page.

International Search Report and Written Opinion, dated Feb. 28, 2013, PCT application No. PCT/US2012/066421, pp. 13.

International Search Report dated Oct. 10, 2014, for PCT Application No. PCT/US2014/029413, filed Mar. 14, 2014, 5 pages.

Kumar, Y et al. (2003, e-published Oct. 2, 2003). "Process for Developing 3β-[4-(S)-Arylacetylamino-4β-(2-(2-furyl)ethyl] azetidin-2-one: A Carbacephem Key Intermediate," *Org. Proc. Res. Dev.*7(6):933-935.

Lall, Manjinder S. et al., Serine and Threonine [3 -Lactones: A New Class of Hepatitis A Virus 3C Cysteine Proteinase Inhibitors, *Journal of Organic Chemistry* (American Chemical Society), 2002, vol. 67, No. 5, pp. 1536-1547.

Li et al., "Design and Synthesis of Potent N-Acylethanolamine-hydrolyzing Acid Amidase (NAAA) Inhibitor as Anti-Inflammatory Compounds," *PLoS One*, Aug. 2012;7(8):e43023.

Lohse et al., "Incorporation of a phosphonic acid isostere of aspartic acid into peptides using Fmoc-solid phase synthesis," *Tetrahedron Letters*, 1998, vol. 39, Issue 15, pp. 2067-2070.

Mori, Tomonori et al., "Total Synthesis of Siomycin A: Construction of Synthetic Segments," *Chemistry—An Asian Journal* (Wiley—VCH Verlag), 2008, vol. 3, No. 6, pp. 984-1012.

Nissen, S.E. et al. (Mar. 28, 2007, e-published Mar. 25, 2007). "Effects of a potent and selective PPAR-α agonist in patients with atherogenic dyslipidemia or hypercholesterolemia: two randomized controlled trials," *JAMA* 297(12):1362-1373.

Office Actions and Responses for U.S. Appl. No. 13/684,017, filed Nov. 21, 2012, 110 pages.

Pu et al.; Synthesis and Acylation of Salts of L-Threonine -Lactone: A route to _-Lactone Antibiotics; *Journal of Organic Chemistry*; vol. 56, vol. 3; pp. 1280-1283, published Feb. 1, 1991.

Pu et al.; Synthesis, Stability, and Antimicrobial Activity of (+)-Obafluorin and Related beta-Lactone Antibiotics; *Journal of Organic Chemistry*, vol. 59, No. 13, pp. 3642-3655 (1994).

Sasso, O. et al. (May 2012, e-published Mar. 7, 2012). "Peripheral FAAH inhibition causes profound antinociception and protects against indomethacin-induced gastric lesions," *Pharmacol Res* 65(5):553-563.

Saturnino et al., "Synthesis and biological evaluation of new potential inhibitors of N-acylethanolamine hydrolyzing acid amidase," *Bioorganic & Medicinal Chemistry Letters*, 2010, vol. 20, Issue 3, pp. 1210-1213.

(56) References Cited

OTHER PUBLICATIONS

Spetzler et al., "Preparation and application of O-amino-serine, Ams, a new building block in chemoselective ligation chemistry," Journal of Peptide Science, 1999, vol. 5, Issue 12, pp. 582-592.

Stigers, Dannon J. et al., "Incorporation of chlorinated analogues of aliphatic amino acids during cell-free protein synthesis," Chemical Communications (Royal Soc of Chemistry), 2011, 47(6):1839-1841.

Tsuboi, K. et al. (Mar. 25, 2005, e-published Jan. 17, 2005). "Molecular characterization of N-acylethanolamine-hydrolyzing acid amidase, a novel member of the choloylglycine hydrolase family with structural and functional similarity to acid ceramidase," J Biol Chem 280(12):11082-11092.

Tsuboi, K. et al. (Aug. 2007). "The N-acylethanolamine-hydrolyzing acid amidase (NAAA)," Chem Biodivers 4(8):1914-1925.

Ueda et al. "A second N-acylethanolamine hydrolase in mammalian tissues," Neuropharmacology, 2005, vol. 48, pp. 1079-1085.

Valls, Nativitat et al., Synthesis of β-chloro α-amino acids: (2S,3R)- and (2S,3S)-3-chloroleucine, Tetrahedron Letters (Elsevier B.V.), 2006, vol. 47, No. 22, pp. 3701-3705.

Wang, Zheming et al., "β-Lactone probes identify a papain-like peptide ligase in *Arabidopsis thaliana*," Nature Chemical Biology (Nature Publishing Group), 2008, vol. 4, No. 9, pp. 557-563.

Written Opinion dated Oct. 10, 2014, for PCT Application No. PCT/US2014/029413, filed Mar. 14, 2014, 4 pages.

Written Opinion dated Dec. 17, 2008, for PCT Application No. PCT/US2008/079621, filed Oct. 10, 2008 4 pages.

\* cited by examiner

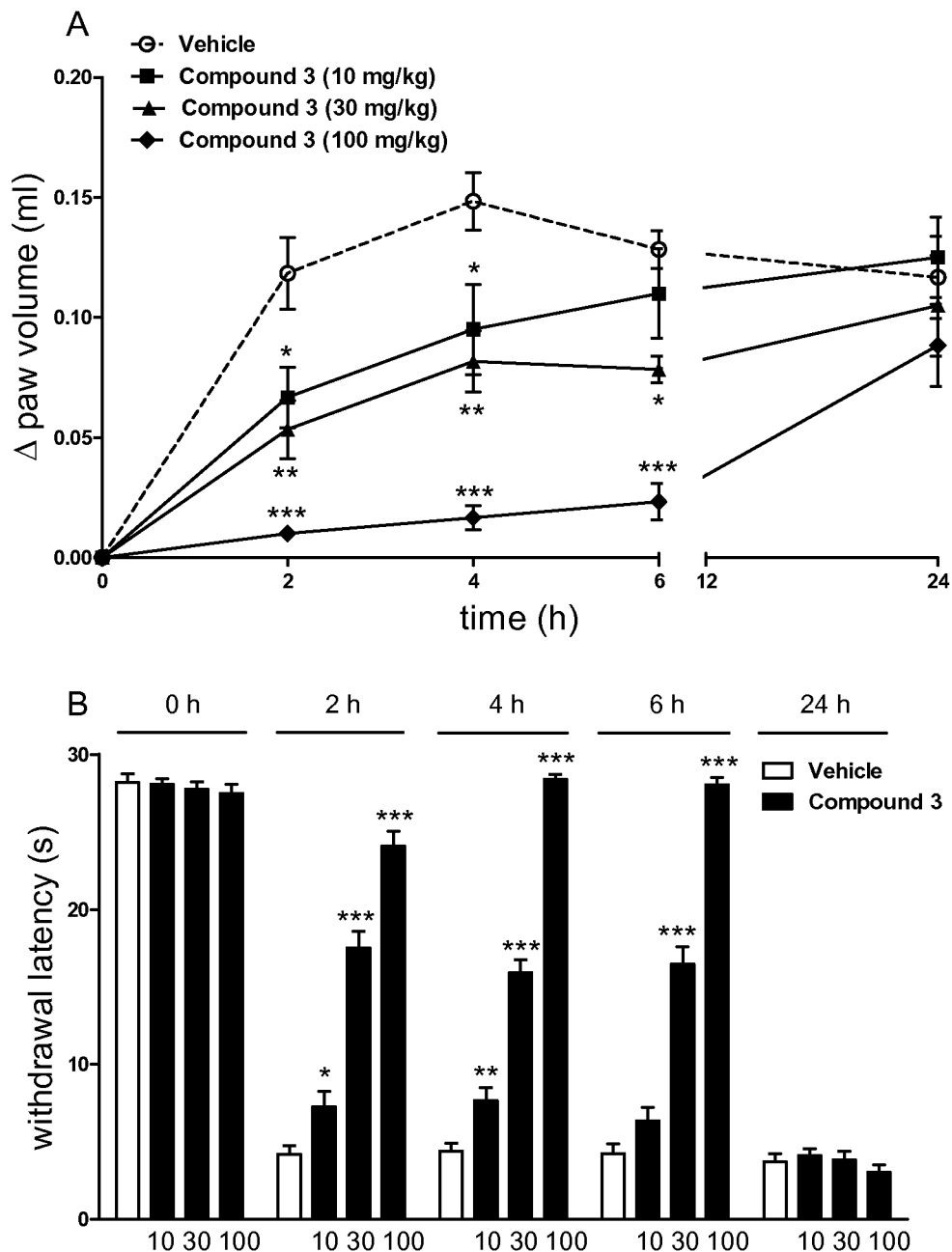

AMIDE DERIVATIVES OF LACTAM BASED N-ACYLETHANOLAMINE ACID AMIDASE (NAAA) INHIBITORS

CROSS-REFERENCES TO RELATED APPLICATIONS

This application is a continuation of International Patent Application No. PCT/US2014/029007, filed Mar. 14, 2014, which in claims the benefit of U.S. Provisional Patent Application No. 61/799,470, filed Mar. 15, 2013, all of which are incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with Government support under Grant No. DA012413, awarded by the National Institutes of Health. The Government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 79828-903322_ST25.TXT, created Mar. 12, 2014, 1035 bytes, machine format IBM-PC, MS-Windows operating system, is hereby incorporated by reference.

BACKGROUND OF THE INVENTION

While there are numerous compositions and methods known in the art to treat pain and inflammation, numerous difficulties remain. Most significantly, side effects over long administration periods and/or higher dosages often limit the use of such drugs. For example, certain COX-2 inhibitors are implicated in adverse cardiovascular events and aspirin-type pain medication often increase the risk of intestinal bleeding. In other examples, ibuprofen and acetaminophen tend to negatively impact hepatic function, especially at higher dosages.

Ethanolamides of long-chain fatty acids, usually referred to as N-acylethanolamines (NAEs), are present in numerous lower and higher organisms, and mammals with a wide variety of functions. For example, anandamide, a polyunsaturated fatty acid-type NAE, was demonstrated to have cannabimimetic activity. In contrast, saturated and monounsaturated NAEs are inactive as ligands of cannabinoid receptors. However, such compounds have been reported to possess a variety of other biological activities. For example, N-oleoylethanolamine (OEA), a monounsaturated fatty acid-type NAE, was shown to be anorexic via the peroxisome proliferator-activated receptor-α (PPAR-α), and N-stearoylethanolamine (SEA), a saturated fatty acid-type NAE, to be pro-apoptotic and anorexic.

N-palmitoylethanolamine (PEA), the naturally occurring amide of palmitic acid and ethanolamine, is a member of the saturated fatty acid-type NAE family. PEA has been shown to inhibit peripheral inflammation and mast cell degranulation (Mazzari et al., *European Journal of Pharmacology* 1996, 300, 227-36; Berdishev et al., *Life Science* 1998, 63, 125-129; D'Agostino et al., *Journal of Pharmacology and Experimental Therapeutics* 2007, 322, 1137-1143), as well as to exert antinociceptive effects in rats and mice (Calignano et al., *Nature* 1998, 394, 277-281; Calignano et al., *European Journal of Pharmacology* 2001, 419, 191-198).

These properties have been shown to be dependent on PPAR-α, and PEA activates this nuclear receptor with a potency comparable to the synthetic agonist WY14,643 (Lo Verme et al., *Molecular Pharmacology* 2005, 67, 15-19; Lo Verme et al., *Journal of Pharmacology and Experimental Therapeutics* 2006, 319, 1051-1061).

In the carrageenan-induced paw edema and phorbol ester-induced ear edema models, PEA applied as a drug attenuates inflammation in wild-type mice, but has no effect in mice lacking PPAR-α(see LoVerme et al., *Molecular Pharmacology* 2005, 67, 15-19). PEA was also found to suppress pain behaviors induced, in mice, by chemical tissue injury, nerve damage, or inflammation (see LoVerme et al., *Journal of Pharmacology and Experimental Therapeutics* 2006, 319, 1051-1061).

In addition to the pharmacological activities shown in animal models, PEA has been reported to attenuate skin inflammation in humans (Kemeny et al., *Skin Pharmacology and Physiology* 2007, 20, 155-161).

Activation of PPAR-α by selective receptor agonists could be envisaged as a viable approach for the treatment of inflammatory and pain states. However, the prolonged clinical use of PPAR-α agonists has been linked to serious adverse events, which include oncogenesis, renal dysfunction, and cardiovascular toxicity (Nissen et al., *JAMA* 2007, 297, 1362-1373). Sustaining PEA signaling at PPAR-α by protecting this lipid amide from degradation is envisaged as an alternative to direct PPAR-α activation by receptor agonists.

NAEs are substrate of the N-acylethanolamine acid amidase (NAAA), an enzyme that catalytically hydrolyzes the NAE to ethanolamine and the corresponding fatty acid. NAAA is a cysteine hydrolase that belongs to the N-terminal nucleophile (Ntn) family of enzymes (Tsuboi et al., *Journal of Biological Chemistry* 2005, 280, 11082-11092; Tsuboi et al., *Chemistry and Biodiversity* 2007, 4, 1914-1925). NAAA exhibits a substantial preference for PEA over other NAEs. Therefore, inhibition of NAAA is expected to decrease the inactivation and restore the levels of PEA in pathological conditions characterized by markedly reduced concentrations of this signaling molecule.

There exists a problem in the field to which the instant invention pertains related to the preparation of new inhibitors of NAAA for use in the preparation of pharmaceutical composition therapeutics. Surprisingly, the instant invention solves this as well as several other problems in the relevant field by providing, inter alia, small molecule chemical inhibitors of NAAA as well as methods for treating pain and inflammation.

BRIEF SUMMARY OF THE INVENTION

In one aspect, the present invention provides compound having the structure of Formula I:

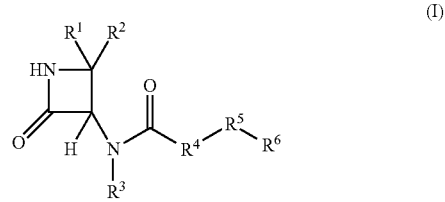

In Formula I, $R^1$ and $R^2$ are each independently selected from hydrogen, alkyl, aryl, cycloalkyl, arylalkyl, or cycloalkylalkyl; or $R^1$ and $R^2$ form a cycloalkyl substituent together with the carbon to which they are attached. $R^3$ is selected from hydrogen or alkyl. $R^4$ is selected from the group consisting of alkyl, alkenyl, alkynyl, aryl, cycloalkyl, heteroaryl, heterocyclyl, heteroarylalkyl, or heterocycloalkyl. $R^5$ is absent or is selected from the group consisting of alkyl, alkoxy, aryl, aryloxy, cycloalkyl, —O—, —S—, —C(O)—, heteroaryl, or heterocyclyl. $R^6$ is absent or is selected from hydrogen, alkyl, alkoxy, aryl, aryloxy, arylalkyloxy, arylalkyl, cycloalkyl, heteroaryl, cycloalkyloxy, heterocycloalkyl, heterocycloalkyloxy, and heterocyclyl. $R^1$, $R^2$, $R^3$, $R^4$, $R^5$, and $R^6$ are each independently optionally substituted with 1-4 substituents selected from hydrogen, lower alkyl, lower alkoxy, aryl, $NR^aR^b$, cyano, halogen, or hydroxyl. $R^a$ and $R^b$ are each independently selected from hydrogen or alkyl. Also included are the pharmaceutically acceptable salt, ester, or prodrug of a compound of Formula I.

In a second aspect, the present invention provides a pharmaceutical composition including one or more compounds having a structure selected from Formulae I, II, III, IV, V, VI, or VII, or a pharmaceutically acceptable formulation thereof, and a pharmaceutically acceptable excipient, carrier or diluent.

In a third aspect, the present invention provides a method of treating a mammal suffering from an inflammatory condition including administering to the mammal a compound having the structure selected from Formula I, II, III, IV, V, VI, or VII.

In a fourth aspect, the present invention provides a method of treating a mammal suffering from a painful or pruritogenic pathological state not attributable to inflammation including administering to the mammal a compound having the structure selected from Formula I, II, III, IV, V, VI, or VII.

In a fifth aspect, the present invention provides a method of treating a mammal suffering from a neurodegenerative disorder, including administering to the mammal a compound having the structure selected from Formula I, II, III, IV, V, VI, or VII.

In a sixth aspect, the present invention provides a method of inhibiting NAAA including contacting the NAAA in vitro with a compound having the structure selected from Formula I, II, III, IV, V, VI, or VII.

BRIEF DESCRIPTION OF THE DRAWINGS

FIG. 1 shows the effects of intraperitoneal administration of compound 3 on carrageenan-induced hyperalgesia and edema. Compound 3 (10-100 mg/kg) reduced paw edema (A) and heat hyperalgesia (B) measured immediately before (0 h) and at various times after compound 3 injection. Results are expressed as mean±SEM (n=6, each group). * $p<0.05$,  $p<0.01$ and * $p<0.001$ vs. vehicle.

DETAILED DESCRIPTION OF THE INVENTION

I. General

The present invention provides compounds and pharmaceutical compositions which inhibit NAAA as well as methods of inhibiting NAAA using small organic compounds and pharmaceutical compositions. Also provided are compounds for use as a medicament in the treatment of pathologies where modulation of the levels of PEA and other NAE (e.g., PEA, SEA) is needed, such as in the treatment of inflammation and pain and other disorders where modulation of palmitoylethanolamine, OEA or NAE (OEA, SEA) levels is clinically relevant. Also provided are methods for modulating the levels of NAE (OEA, SEA) in a subject by administering a composition set forth herein. Also provided are methods for treating conditions associated with reduced levels of NAE, including acute inflammation, chronic inflammation, acute pain, acute inflammatory pain, chronic inflammatory pain, and neuropathic pain, by administering a therapeutically effective amount of a compound of Formula I according to the invention. Also provided are pharmaceutical compositions which include a compound set forth herein, or a pharmaceutically acceptable salt thereof, and pharmaceutically acceptable excipients, carriers and/or diluents. Also provided are methods for preparing compounds of Formula I through a process consisting of suitable synthetic transformations.

II. Definitions

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer Verlag.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). As used herein, the following terms have the meanings ascribed to them unless specified otherwise.

It is noted here that as used in this specification and the appended claims, the singular forms "a," "an," and "the" include plural reference unless the context clearly dictates otherwise.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. The term "pharmaceutical composition" indicates a composition suitable for pharmaceutical use in a subject, including an animal or human. A pharmaceutical composition generally comprises an effective amount of an active agent and a pharmaceutically acceptable carrier.

The term "pharmaceutically acceptable carrier" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in REMINGTON'S PHARMACEUTICAL SCIENCES (Mack Publishing Co., Easton, 19th ed. 1995). Preferred pharmaceutical carriers depend upon the intended mode of administration of the active agent. Typical modes of administration are described below.

The term "effective amount" means a dosage sufficient to produce a desired result on health, including, but not limited to, disease states. The desired result may comprise a subjective or objective improvement in the recipient of the dosage. A subjective improvement may be, for instance with respect to pain, decreased sensation of pain (e.g., noninflammatory pain, neuropathic pain). An objective improvement may be, for instance, an increased ability to move or use (e.g., place weight upon) an affected limb or a longer period of uninterrupted sleep, or a behavioral response indicating an increased tolerance of a painful stimuli.

A "prophylactic treatment" is a treatment administered to a subject who does not have the subject condition (e.g., pain), wherein the treatment is administered for the purpose of decreasing the risk of developing the condition or to counter the severity of the condition (e.g., inflammation; pain, including but not limited to, acute pain, chronic pain, inflammatory pain, non-inflammatory pain, neuropathic pain and pain expected to result from the expected or likely occurrence of a painful event (e.g., surgery)) if one were to develop.

A "therapeutic treatment" is a treatment administered to a subject who has the condition (e.g., pain, and/or exhibits signs or symptoms of pain including but not limited to, acute pain, chronic pain, cancer pain, inflammatory pain, non-inflammatory pain, neuropathic pain, wherein treatment is administered for the purpose of diminishing or eliminating those signs or symptoms) to be treated.

A "therapeutically effective amount" is an amount of an agent sufficient to reduce the signs and/or symptoms of the disease or condition or to prevent, oppose, or reduce their progression. The compound are generally administered to a patient for treatment in a therapeutically effective amount.

The term "treating" means combating, reducing, shortening, alleviating or eliminating a condition or symptoms thereof of the subject (e.g., pain, inflammation).

Pain, particularly severe pain, can be a stressor. Thus, in one aspect the invention is drawn to methods of treating chronic pain conditions, including neuropathic pain, and chronic or intermittent pain associated with chronic health conditions as such conditions are often substantial stressors. "Neuropathic pain" is pain caused by a primary lesion or dysfunction of the nervous system. Such pain is chronic and involves a maintained abnormal state of increased pain sensation, in which a reduction of pain threshold and the like are continued, due to persistent functional abnormalities ensuing from an injury or degeneration of a nerve, plexus or perineural soft tissue. Such injury or degeneration may be caused by wound, compression, infection, cancer, ischemia, or a metabolic or nutritional disorder such as diabetes mellitus. Neuropathic pain includes, but is not limited to, neuropathic allodynia wherein a pain sensation is induced by mechanical, thermal or another stimulus that does not normally provoke pain, neuropathic hyperalgesia wherein an excessive pain occurs in response to a stimulus that is normally less painful than experienced. Examples of neuropathic pain include diabetic polyneuropathy, entrapment neuropathy, phantom pain, thalamic pain after stroke, post-herpetic neuralgia, atypical facial neuralgia pain after tooth extraction and the like, spinal cord injury, trigeminal neuralgia and cancer pain resistant to narcotic analgesics such as morphine. The neuropathic pain includes the pain caused by either central or peripheral nerve damage. And it includes the pain caused by either mononeuropathy or polyneuropathy (e.g., familial amyloid polyneuropathy). As compared to inflammatory pain, neuropathic pain is relatively resistant to therapy with nonsteroidal anti-inflammatory agents and opioid substances (e.g, morphine).

Neuropathic pain may be bilateral in mirror image sites, or may be distributed approximately according to the innervation of the injured nerve, it may persist for months or years, and be experienced as a burning, stabbing, shooting, throbbing, piercing electric shock, or other unpleasant sensation.

The term "alkyl", as used herein, indicates a saturated aliphatic hydrocarbon radical, including straight chain and branched chain radicals of 1 to 16 carbon atoms. More preferably, an alkyl group has 1 to 12 carbon atoms. The term "lower alkyl", as used herein, refers to straight chain and branched chain radicals of 1 to 6 carbon atoms. Non-limiting examples of alkyl are, for instance, methyl, ethyl, propyl, isopropyl, n-butyl, iso-butyl, tert-butyl, n-amyl, iso-amyl, n-hexyl, n-heptyl, n-octyl and the like. Any alkyl group may be unsubstituted or substituted.

The term "alkenyl", as used herein, indicates an alkyl group, as defined herein, consisting of at least two carbon atoms and containing at least one carbon-carbon double bond. Representative examples include, but are not limited to, ethenyl, 1-propenyl, 2-propenyl, 1- or 2-butenyl, 1- or 2-pentenyl, 1-, 2- or 3-hexenyl, 2,4-hexadienyl and the like. Any alkenyl group may be unsubstituted or substituted.

The term "alkynyl", as used herein, indicates an alkyl group, as defined herein, consisting of at least two carbon atoms and containing at least one carbon-carbon triple bond. Representative examples include, but are not limited to, ethynyl, 1-propynyl, 2-propynyl, 1- or 2-butynyl, 1- or 2-pentynyl and the like. Any alkynyl group may be unsubstituted or substituted.

The term "cycloalkyl", as used herein, indicates a 3- to 7-membered all-carbon monocyclic ring, which may contain one or more double bonds but does not have a completely conjugated pi-electron system. Examples of cycloalkyl groups include, without limitation, cyclopropane, cyclobutane, cyclopentane, cyclopentene, cyclohexane, cyclohexene, cyclohexadiene, cycloheptane, norbornane. A cycloalkyl group may be unsubstituted or substituted.

The term "aryl", as used herein, indicates a hydrocarbon consisting of a mono-, bi- or tricyclic ring system, wherein the rings are fused together or linked to each other covalently and at least one of the carbocyclic rings is aromatic. Not limiting examples of aryl groups include, but are not limited to, phenyl, alpha- or beta-naphthyl, 9,10-dihydroanthracenyl, indanyl, fluorenyl, biphenyl and the like. An aryl group may be unsubstituted or substituted.

The term "heteroaryl", as used herein, indicates a mono-, bi- or tricyclic ring system containing from one to three heteroatoms selected from nitrogen, oxygen and sulfur, wherein the rings are fused together or linked to each other covalently and at least one of the rings is aromatic. Not limiting examples of heteroaryl groups include pyrrolyl, furoyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, thiadiazolyl, tetrazolyl, pyridyl, pyrazinyl, pyrimidinyl, pyridazinyl, quinolinyl, isoquinolinyl, quinazolinyl, quinoxalinyl and the like. A heteroaryl group may be unsubstituted or substituted.

The terms "heterocycloalkyl," "heterocyclyl" or "heterocyclic ring", as used herein, mean a 3- to 7-membered, saturated or partially unsaturated carbocyclic ring wherein one or more carbon atoms are independently replaced by nitrogen, oxygen and sulfur. The heteroatom nitrogen and sulfur are optionally oxidized, and the nitrogen atom(s) are optionally quaternized. Not limiting examples of heterocyclyl groups include, for instance, radicals derived from oxirane, aziridine, oxetane, azetidine, tetrahydrofuran, dihydrofuran, tetrahydrothiophene, dihydrothiophene, pyrrolidine, dihydropyrrole, pyran, dihydropyran, tetrahydropyran, tetrahydrothiopyran, piperidine, pyrazoline, oxazoline, isoxazolidine, isoxazoline, thiazolidine, thiazoline, isothiazoline, dioxane, piperazine, morpholine, thiomorpholine, examethyleneimine, homopiperazine, and the like. A heterocyclyl group or a heterocyclic ring may be unsubstituted or substituted.

The term "substituted", as used herein, means that in each of the above alkyl, alkenyl, alkynyl, cycloalkyl, aryl, heteroaryl, heterocyclyl and heterocyclic radical, one or more hydrogen atoms can be independently replaced by a substituent (which is not to be further substituted beyond that indicated) selected from the group consisting of alkyl, substituted alkyl, aryl, substituted aryl, arylalkyl, alkoxy, cycloalkyloxy, aryloxy, arylalkyloxy, hydroxy, heteroarylalkyloxy, heterocyclyloxy, trifluoromethoxy, carboxy, acyl, aroyl, heteroaroyl, halogen, nitro, cyano, alkoxycarbonyl, aryloxycarbonyl, arylalkyloxycarbonyl, cycloalkyloxycarbonyl, heteroaryloxycarbonyl, heterocyclyloxycarbonyl, acyloxy, alkylthio, arylthio, alkysulfinyl, arylsulfinyl, alkylsulfonyl, arylsulfonyl, —O-aroyl, —O-heteroaroyl, —C(=O)—NR$^h$R$^k$, and —NR$^p$R$^q$, wherein each of R$^h$, R$^k$, R$^p$, and R$^q$ independently represents hydrogen, unsubstituted or substituted alkyl, unsubstituted or substituted cycloalkyl, unsubstituted or substituted aryl, unsubstituted or substituted aralkyl, unsubstituted or substituted heteroaryl, acyl, aroyl, heteroaroyl, unsubstituted or substituted heterocyclyl, and when R$^h$ and R$^k$, and R$^p$ and R$^q$ are taken together (i.e. connected directly to each other) with the nitrogen atom to which they are bound, the group —NR$^h$R$^k$ and the group NR$^p$R$^q$ represent a heterocyclyl residue. Any substituent as provided above is not itself further substituted.

The term "aromatic" refers to a moiety wherein the constituent atoms make up an unsaturated ring system, all atoms in the ring system are sp$^2$ hybridized and the total number of π electrons is equal to 4n+2, wherein n is an integer.

The term "acyl", as used herein, means a group obtained by removing the hydroxy group from a carboxylic acid, where said carboxylic acid is an alkyl carboxylic acid, an alkenyl carboxylic acid, an alkynyl carboxylic acid, a cycloalkyl carboxylic acid or a heterocyclic carboxylic acid. Examples of such carboxylic acids include, but are not limited to, acetic acid, propanoic acid, 2-butenoic acid, 2-butynoic acid, cyclopropyl carboxylic acid, cyclobutyl carboxylic, oxetanyl carboxylic acid, tetrahydropyranyl carboxyic acid, and the like.—

The term "aryloxy", as used herein, means a group —O-Acyl.

The term "alkoxy", as used herein, means an unsubstituted or substituted alkyl chain linked to the remainder of the molecule through an oxygen atom. Examples of alkoxy include, but are not limited to, methoxy, ethoxy, propyloxy, isopropyloxy, benzyloxy and the like.

The term "alkoxycarbonyl", as used herein, means a group —C(=O)O-Alkyl, wherein the alkyl is unsubstituted or substituted.

The term "alkysulfinyl", as used herein, means a group —S(O)-Alkyl.

The term "alkylsulfonyl", as used herein, means a group —SO$_2$-Alkyl.

The term "alkylthio", as used herein, means a group —S-Alkyl.

The term "arylalkyl" or "aralkyl", as used herein, means an unsubstituted or substituted alkyl chain in which one of the hydrogen atom is substituted by and aryl group. Examples of aralkyl include, but are not limited to, benzyl, phenethyl, and the like.

The term "arylalkyloxy", as used herein, means an unsubstituted or substituted aralkyl group linked to the remainder of the molecule through an oxygen atom. Examples of aralkyloxy include, but are not limited to, benzyloxy, phenethyloxy, and the like.

The term "arylalkyloxycarbonyl", as used herein, means a group —C(=O)O-Aralkyl, wherein the aralkyl is unsubstituted or substituted.

The term "aroyl", as used herein, means a group obtained by removing the hydroxy group from an aryl carboxylic acid.

The term "aryloxy", as used herein, means an unsubstituted or substituted aryl group linked to the remainder of the molecule through an oxygen atom. Examples of aryloxy include, but are not limited to, phenoxy, alpha- or beta-naphthyloxy, biphenyloxy and the like.

The term "aryloxycarbonyl", as used herein, means a group —C(=O)O-Aryl, wherein the aryl is unsubstituted or substituted.

The term "arysulfinyl", as used herein, means a group —S(O)-Aryl.

The term "arylsulfonyl", as used herein, means a group —SO$_2$-Aryl.

The term "arylthio", as used herein, means a group —S-Aryl.

The term "carboxy" means a —COOH radical.

The term "cyano" means a —CN radical.

The term "cycloalkyloxy", as used therein, means an unsubstituted or substituted cycloalkyl group linked to the remainder of the molecule through an oxygen atom. Examples of cycloalkyloxy include, but are not limited, to cyclopropyloxy, cyclobutyloxy, cyclopentyloxy, cyclopentenyloxy, cyclohexyloxy, cyclohexenyloxy, cyclohexadienyloxy, cycloheptanyloxy and the like.

The term "cycloalkyloxycarbonyl", as used therein, means a group —C(=O)O—Cycloalkyl, wherein the cycloalkyl is unsubstituted or substituted.

The term "halogen", as used herein, indicates fluorine (F), chlorine (Cl), bromine (Br) or iodine (I).

The term "heteroaroyl", as used herein, indicates a group obtained by removing the hydroxy group from a heteroaryl carboxylic acid.

The term "heteroaryloxy", as used therein, means an unsubstituted or substituted heteroaryl group linked to the remainder of the molecule through an oxygen atom.

The term "heteroaryloxycarbonyl", as used therein, means a group —C(=O)O—Heteroaryl, wherein the heteroaryl is unsubstituted or substituted.

The terms heterocycloalkyloxy or "heterocyclyloxy", as used therein, means an unsubstituted or substituted heterocyclyl group linked to the remainder of the molecule through an oxygen atom.

The term "heterocyclyloxycarbonyl", as used therein, means a group —C(=O)O-Heterocyclyl, wherein the heterocyclyl is unsubstituted or substituted.

The term "hydroxy", as used herein, means a —OH radical.

The term "trifluoromethoxy" means a —OCF$_3$ radical.

A wavy bond depicted in a structure shown herein represents all possible stereochemical possibilities for the bond.

A person having ordinary skill in the art will immediately understand that the definitions of substituents (e.g. R groups) provided herein are intended to obey the standard rules of chemical valency. For clarity, where a formula provided herein requires a particular substituent, when present, to be divalent, (e.g. R$^4$ and R$^5$ in Formula I) a person having ordinary skill in the art will immediately understand that the definitions of that substituent are divalent in order to obey the standard rules of chemical valency. For example, in compounds of formula I below, when R$^4$ is set forth as being an R$^4$ substituent selected from alkyl, alkenyl, alkynyl, aryl, cycloalkyl, heteroaryl, heterocyclyl, heteroarylalkyl, and heterocycloalkyl, the R$^4$ substituent may alternatively and equivalently be referred to as alkylene, alkenylene, alkynylene, arylene, cycloalkylene, heteroarylene, heterocyclylene, heteroarylalkylene, and heterocycloalkylene, respectively. Thus, for example, where the standard rules of chemical valency require divalency for a particular substituent, that particular substituent may be equally referred to as alkyl or alkylene, alkenyl or alkenylene, alkynyl or alkynylene, aryl or arylene, cycloalkyl or cycloalkylene, heteroaryl or heteroarylene, heterocyclyl or heterocyclylene, heteroarylalkyl or heteroarylalkylene, or heterocycloalkyl or heterocycloalkylene.

III. Compounds

In some embodiments, the present invention provides a compound having the structure of Formula I:

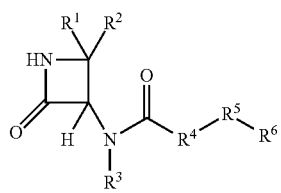

(I)

wherein R$^1$ and R$^2$ are each independently selected from the group consisting of hydrogen, alkyl, aryl, cycloalkyl, arylalkyl, and cycloalkylalkyl; or R$^1$ and R$^2$ form a cycloalkyl substituent together with the carbon to which they are attached. In some embodiments, R$^3$ is selected from the group consisting of hydrogen and alkyl. In some embodiments, R$^4$ is selected from the group consisting of alkyl, alkenyl, alkynyl, aryl, cycloalkyl, heteroaryl, heterocyclyl, heteroarylalkyl, and heterocycloalkyl (e.g., also referred herein as alkylene, alkenylene, alkynylene, arylene, cycloalkylene, heteroarylene, heterocyclylene, heteroarylalkylene, and heterocycloalkylene). In some embodiments, R$^5$ is absent or is selected from the group consisting of alkyl, alkoxy, aryl, aryloxy, cycloalkyl, —O—, —S—, —C(O)—, heteroaryl, and heterocyclyl (e.g., also referred herein as alkylene, alkoxy, arylene, aryloxy, cycloalkylene, —O—, —S—, —C(O)—, heteroarylene, and heterocyclylene). In some embodiments, R$^6$ is absent or is selected from the group consisting of hydrogen, alkyl, alkoxy, aryl, aryloxy, arylalkoxy arylalkyl, cycloalkyl, heteroaryl, cycloalkyloxy, heterocycloalkyloxy, and heterocyclyl. In Formula (I), R$^1$, R$^2$, R$^3$, R$^4$, R$^5$, and R$^6$ are each independently optionally substituted with 1-4 substituents independently selected from the group consisting of hydrogen, lower alkyl, lower alkoxy, aryl, NR$^a$R$^b$, cyano, halogen, and hydroxyl. Also, R$^a$ and R$^b$ are each independently selected from the group consisting of hydrogen and alkyl. The present invention also provides pharmaceutically acceptable salts, esters, or prodrugs of the compounds of Formula (I). In some embodiments, R$^6$ is selected from the group consisting of hydrogen, alkyl, alkoxy, aryl, aryloxy, arylalkoxy arylalkyl, cycloalkyl, heteroaryl, cycloalkyloxy, heterocycloalkyloxy, and heterocyclyl.

In some other embodiments, R$^1$ and R$^2$ are each independently selected from the group consisting of hydrogen, alkyl, aryl, cycloalkyl, arylalkyl, and cycloalkylalkyl; or R$^1$ and R$^2$ form a cycloalkyl substituent together with the carbon to which they are attached. In some embodiments, R$^3$ is selected from the group consisting of hydrogen and alkyl. In some embodiments, R$^4$ is selected from the group consisting of alkyl, alkenyl, alkynyl, aryl, cycloalkyl, heteroaryl, heterocyclyl, heteroarylalkyl, and heterocycloalkyl. In some embodiments, R$^5$ is absent or is selected from the group consisting of alkyl, alkoxy, aryl, aryloxy, cycloalkyl, —O—, —S—, —C(O)—, heteroaryl, and heterocyclyl. In some embodiments, R$^6$ is absent or is selected from the group consisting of hydrogen, alkyl, alkoxy, aryl, aryloxy, arylalkoxy, arylalkyl, cycloalkyl, heteroaryl, cycloalkyloxy, heterocycloalkyloxy, and heterocyclyl. In Formula (I), R$^1$, R$^2$, R$^3$, R$^4$, R$^5$, and R$^6$ are each independently optionally substituted with 1-4 substituents independently selected from the group consisting of hydrogen, lower alkyl, lower alkoxy, aryl, NR$^a$R$^b$, cyano, halogen, and hydroxyl. Also, R$^a$ and R$^b$ are each independently selected from the group consisting of hydrogen and alkyl. The present invention also provides pharmaceutically acceptable salts, esters, or prodrugs of the compounds of Formula (I).

In some embodiments of any of the above, R$^4$-R$^5$ together provide a 4, 5 or 6 atom chain (which may be substituted or unsubstituted) linking R$^6$ and the remainder of the molecule. In further of such embodiments, R$^4$-R$^5$ is an substituted or unsubstituted butyl, pentyl, hexyl, phenyl, methyl-phenyl, phenyl-methyl, phenyl-ethyl, or ethyl-phenyl. In these embodiments, further R$^6$ can be substituted or unsubstituted aryl, cyclohexyl, or phenyl.

In some embodiments, the present invention provides a compound having the structure selected from the group of Formulae II, III, IV, V, VI, and VII:

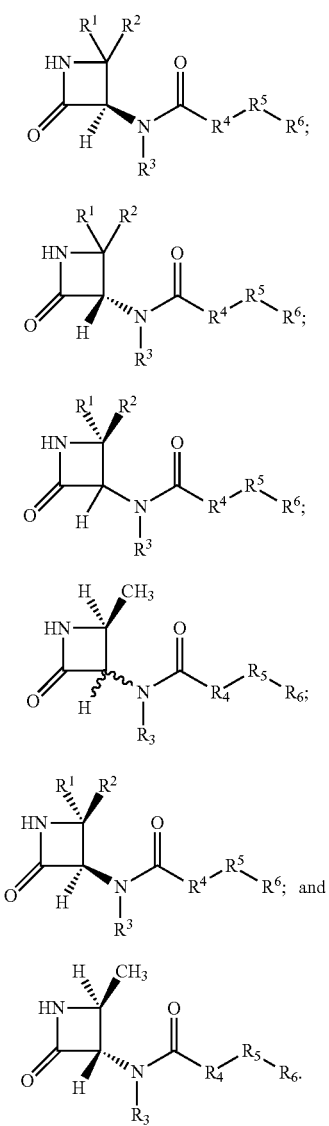

In Formula II-VII, the substituents $R^1$, $R^2$, $R^3$, $R^4$, $R^5$, and $R^6$ are as defined above.

In some embodiments, the invention provides compounds which would be embraced by any one of the above formulae I to VII, wherein $R^1$ and $R^2$ are both hydrogen or both methyl, or $R^1$ is hydrogen and $R^2$ is methyl. In further embodiments of such $R^3$ is hydrogen or methyl.

In further embodiments of any of the above compounds of any one of Formula I-VII, the compound is one in which $R^4$ is aryl (e.g., phenyl), alkyl, alkenyl, or cycloalkyl (e.g., cyclohexyl, 1-methyl-cyclohexyl). In some further embodiments, the $R^4$ alkyl is selected from the group consisting of methyl, ethyl, i-propyl, n-propyl, n-butyl, t-butyl, i-butyl, pentyl, hexyl, heptyl, octyl, nonyl, decyl, undecyl, and dodecyl. In some further embodiments, where the $R^4$ is alkenyl, the alkenyl is selected from the group consisting of propenyl, 1-propenyl, 2-propenyl, 1-butenyl, 2-butenyl, 1-pentenyl, 2-pentenyl, 3-pentenyl, 1-hexenyl, 2-hexenyl, 3-hexenyl, 1-heptenyl, 2-heptenyl, 3-heptenyl, 4-heptenyl, 1-octenyl, 2-octenyl, 3-octenyl, and 4-octenyl. These recited $R^4$ members may be substituted or unsubstituted.

In some further embodiments of the compounds of any of the above formulae, the present invention provides compounds where $R^5$ is absent, or $R^5$ is aryl (e.g., phenyl), or $R^5$ is selected from the group consisting of methyl, ethyl, propyl, and butyl; or $R^5$ is selected from the group consisting of methoxy, ethoxy, propoxy, and butoxy. These $R^5$ members, when present, may be substituted or unsubstituted.

In still further embodiments of the above compounds of any of the above formulae, the present invention provides compounds wherein $R^6$ is alkyl, cycloalkyl, or aryl. In some such embodiments, $R^6$ is an alkyl is selected from the group consisting of methyl, ethyl, i-propyl, n-propyl, n-butyl, t-butyl, i-butyl, pentyl, hexyl, heptyl, octyl, nonyl, decyl, undecyl, and dodecyl. In yet other embodiments, the $R^6$ cycloalkyl is selected from the group consisting of cyclobutyl, cyclopentyl, and cyclohexyl. In some embodiments, accordingly $R^6$ is phenyl or benzyloxy. The above recited $R^6$ members may be substituted or unsubstituted.

In yet other further embodiments of any of the above compounds of any of the above formulae, the present invention provides a compound wherein $R^4$-$R^5$-$R^6$ is selected from the group consisting of biphenyl, octyl, trans-2-octenyl, cis-2-octenyl, hexyl-phenyl, propyl-benzyloxy, 4-benzyloxy-phenyl, 1-methyl-cyclohexyl, 3-phenyl-2-propenyl, butyl-cyclohexyl, pentyl-cyclohexyl, hexyl-cyclohexyl, 2-biphenyl-ethyl, 2-phenyl-ethyl, 4-phenyl-butyl, 5-phenyl-pentyl, pentyl, hexyl, heptyl, octyl, nonyl, and decyl. These members may be substituted or unsubstituted.

In some embodiments, of any of the above formulae, the present invention provides compounds where $R^5$ is absent. In certain embodiments, $R^5$ is selected from the group consisting of methyl, ethyl, propyl, and butyl. In some embodiments, $R^5$ is selected from the group consisting of methoxy, ethoxy, propoxy, and butoxy. In yet other embodiments, $R^5$ selected from the group consisting of —O—, —S— or —C(O)—.

In some embodiments, $R^4$-$R^5$ is substituted or unsubstituted butyl, pentyl, hexyl, phenyl, methyl-phenyl, phenyl-methyl, phenyl-ethyl, or ethyl-phenyl and $R^6$ is substituted or unsubstituted aryl, cyclohexyl, or phenyl.

In still further embodiments of any of the above compounds of any of the above formula, $R^1$ and $R^2$ are unsubstituted; $R^1$, $R^2$, and $R^3$ are each unsubstituted; $R^4$ is unsubstituted, each of $R^1$, $R^2$, $R^3$, and $R^4$ is unsubstituted, $R^5$ and $R^6$ are each unsubstituted; or each of $R^1$, $R^2$, $R^3$, $R^4$, $R^5$, and $R^6$ is unsubstituted; or each of $R^1$, $R^2$, $R^3$, $R^4$, $R^5$ and $R^6$ member independently has from 0, 1, 2, or 3 substituents; from 0 to 2 substituents; or from 0 to 1 substituent. In still further embodiments of such each substituent is independently selected from the group consisting of lower alkyl and halogen (e.g., F, Cl).

In some embodiments, the present invention provides a compound selected from the group consisting of

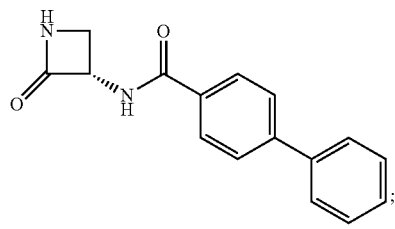

-continued
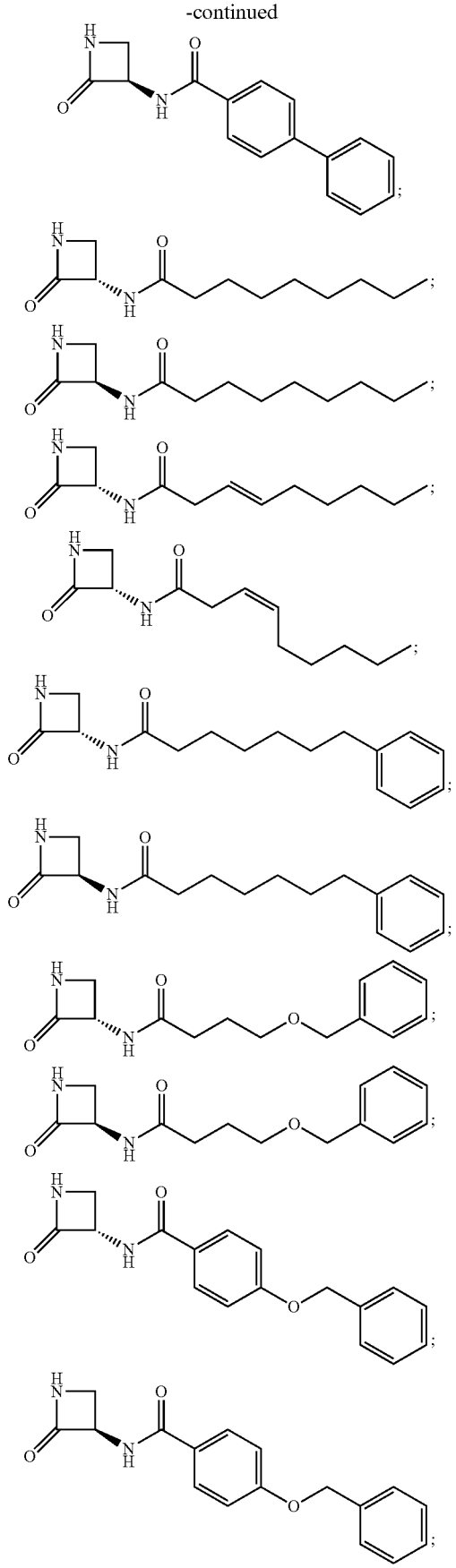
-continued
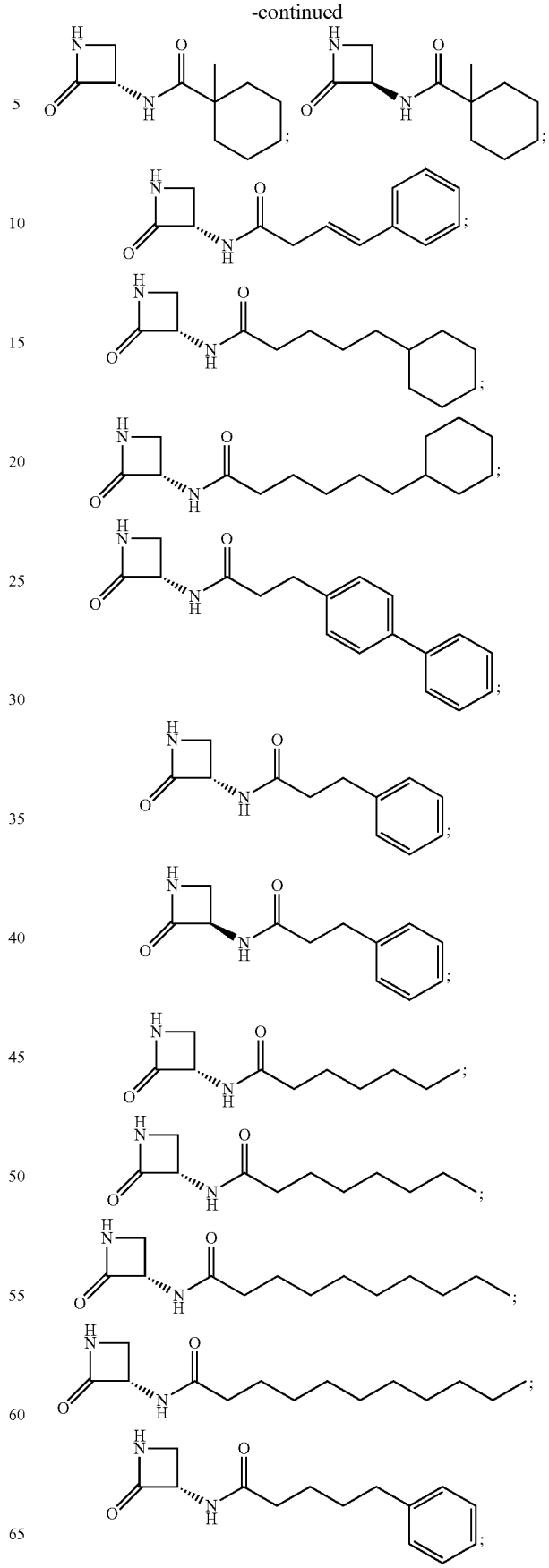

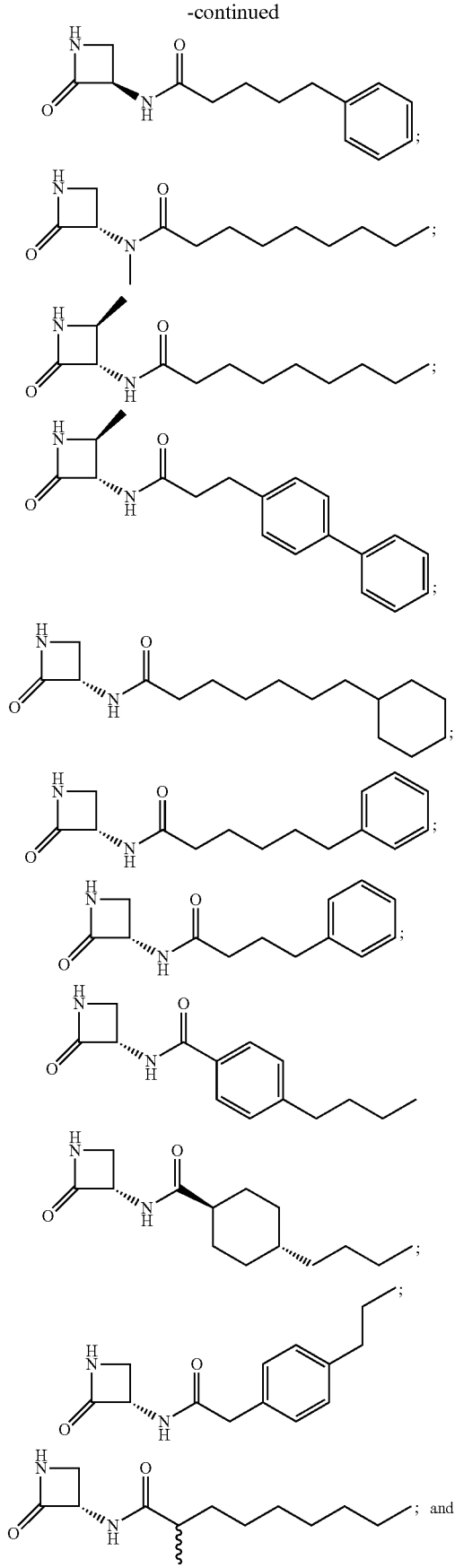

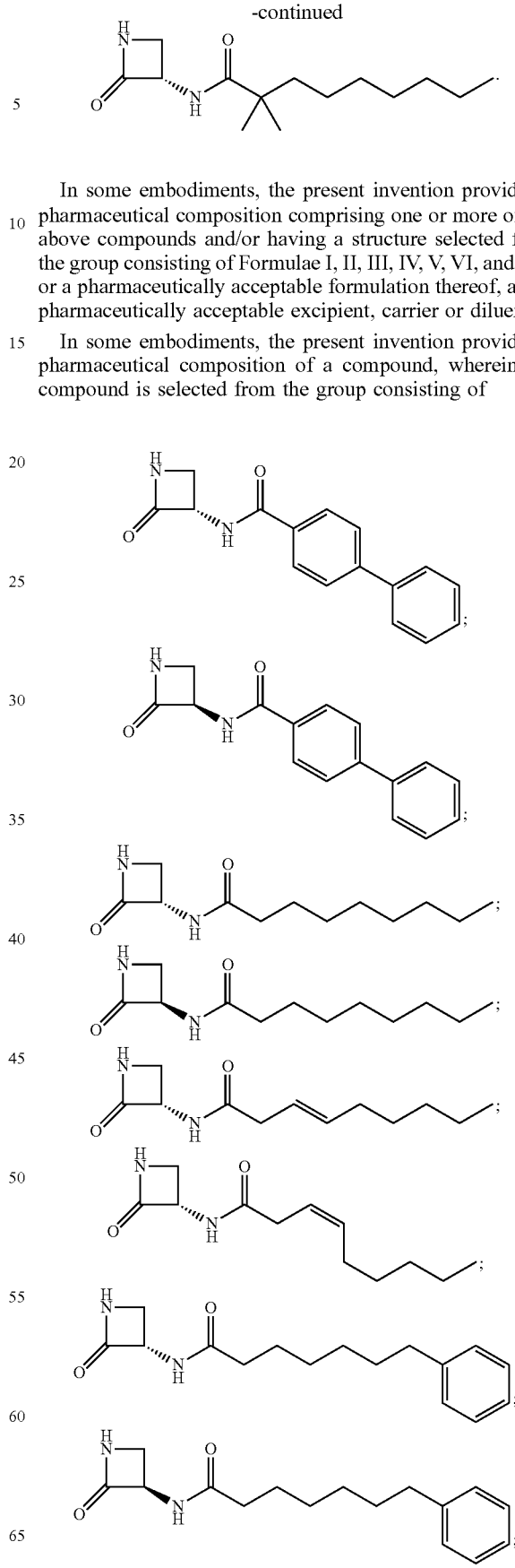

In some embodiments, the present invention provides a pharmaceutical composition comprising one or more of the above compounds and/or having a structure selected from the group consisting of Formulae I, II, III, IV, V, VI, and VII, or a pharmaceutically acceptable formulation thereof, and a pharmaceutically acceptable excipient, carrier or diluent.

In some embodiments, the present invention provides a pharmaceutical composition of a compound, wherein the compound is selected from the group consisting of 17
-continued
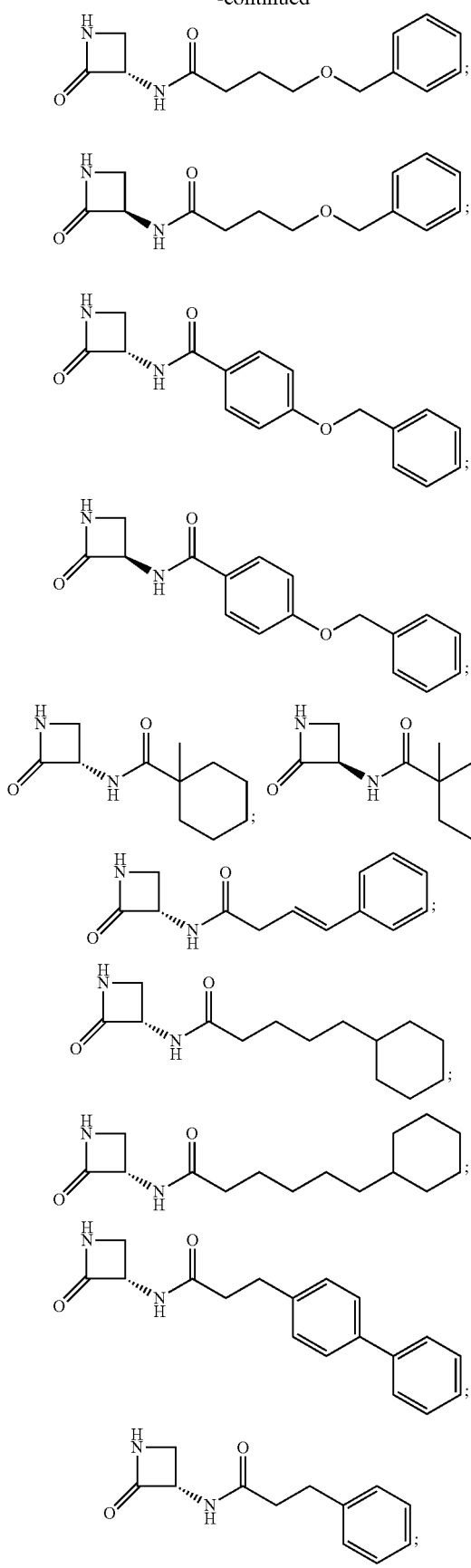
18
-continued
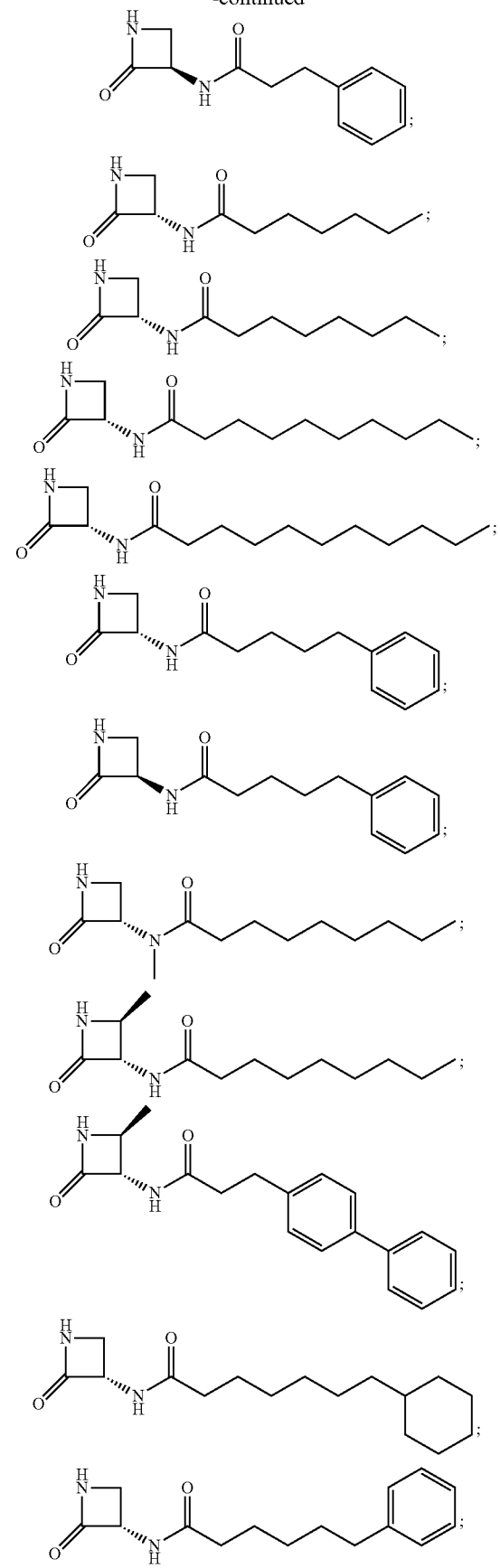

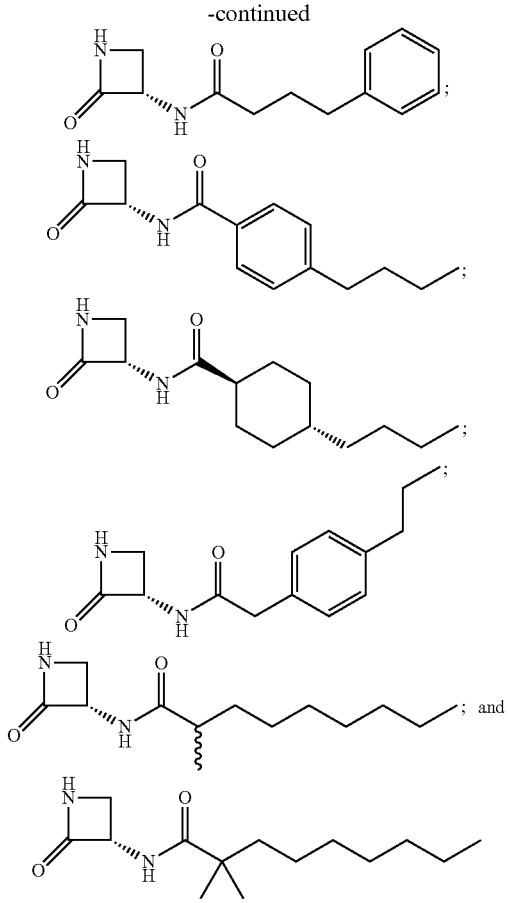

In certain embodiments, the present invention provides a compound selected from the group consisting of:
4-phenyl-N-[(3S)-2-oxoazetidin-3-yl]-benzamide
4-phenyl-N-[(3R)-2-oxoazetidin-3-yl]-benzamide
N-[(3S)-2-oxoazetidin-3-yl]-nonanamide
N-[(3R)-2-oxoazetidin-3-yl]-nonanamide
(E)-N-[(3S)-2-oxoazetidin-3-yl]-non-3-enamide
(Z)—N-[(3S)-2-oxoazetidin-3-yl]-non-3-enamide
7-phenyl-N-[(3S)-2-oxoazetidin-3-yl]-heptanamide
7-phenyl-N-[(3R)-2-oxoazetidin-3-yl]-heptanamide
4-benzyloxy-N-[(3S)-2-oxoazetidin-3-yl]-butanamide
4-benzyloxy-N-[(3R)-2-oxoazetidin-3-yl]-butanamide
4-benzyloxy-N-[(3S)-2-oxoazetidin-3-yl]-benzamide
4-benzyloxy-N-[(3R)-2-oxoazetidin-3-yl]-benzamide
1-methyl-N-[(3S)-2-oxoazetidin-3-yl]-cyclohexanecarboxamide
1-methyl-N-[(3R)-2-oxoazetidin-3-yl]-cyclohexanecarboxamide
(E)-4-phenyl-N-[(3S)-2-oxoazetidin-3-yl]-but-3-enamide
5-cyclohexyl-N-[(3S)-2-oxoazetidin-3-yl]-pentanamide
6-cyclohexyl-N-[(3S)-2-oxoazetidin-3-yl]-hexanamide
3-(4-phenylphenyl)-N-[(3S)-2-oxoazetidin-3-yl]-propanamide
3-phenyl-N-[(3S)-2-oxoazetidin-3-yl]-propanamide
3-phenyl-N-[(3R)-2-oxoazetidin-3-yl]-propanamide
N-[(3S)-2-oxoazetidin-3-yl]-heptanamide
N-[(3S)-2-oxoazetidin-3-yl]-octanamide
N-[(3S)-2-oxoazetidin-3-yl]-decanamide
N-[(3S)-2-oxoazetidin-3-yl]-undecanamide
5-phenyl-N-[(3S)-2-oxoazetidin-3-yl]-pentanamide
5-phenyl-N-[(3R)-2-oxoazetidin-3-yl]-pentanamide
N-methyl-N-[(3S)-2-oxoazetidin-3-yl]-nonanamide
N-[(2S,3S)-2-methyl-4-oxo-azetidin-3-yl]-nonanamide
3-(4-phenylphenyl)-N-[(2S,3S)-2-methyl-4-oxo-azetidin-3-yl]-propanamide
7-cyclohexyl-N-[(3S)-2-oxoazetidin-3-yl]-heptanamide
6-phenyl-N-[(3S)-2-oxoazetidin-3-yl]-hexanamide
4-phenyl-N-[(3S)-2-oxoazetidin-3-yl]-butanamide,
4-butyl-N-[(3S)-2-oxoazetidin-3-yl]-benzamide;
(1r,4R)-4-butyl-N—((S)-2-oxoazetidin-3-yl)cyclohexanecarboxamide;
N-[(3S)-2-oxoazetidin-3-yl]-2-(4-propylphenyl)acetamide;
(2R)-2-methyl-N-[(3S)-2-oxoazetidin-3-yl]nonanamide and (2S)-2-methyl-N-[(3S)-2-oxoazetidin-3-yl]nonanamide; and
2,2-dimethyl-N-[(3S)-2-oxoazetidin-3-yl]nonanamide.

Compounds of the present invention may be isolated in the form of their pharmaceutically acceptable acid addition salts, such as the salts derived from inorganic and organic acids. The term "pharmaceutically acceptable salts" refers to salts prepared from pharmaceutically acceptable, non-toxic acids including inorganic or organic acids. Such acids include hydrochloric, sulfuric, phosphoric, glycolic, malic, maleic, tartaric, succinic, citric, malonic acid and the like.

Compounds of the present invention may be in crystalline forms. In certain embodiments, the crystalline forms of the compounds described herein are polymorphs. In further embodiments, hydrates and solvates of the compounds described herein or their pharmaceutically acceptable salts are contemplated by this invention.

Compounds of the present invention may contain one or more chiral centers. Compounds containing one chiral center can occur as single enantiomers or mixtures of the two enantiomers. Such mixtures occur as racemates or racemic mixtures. Compounds containing more than one chiral center can occur as single enantiomers and pairs of enantiomers, and as stereoisomers which are not enantiomers, referred to as diastereoisomers. Compounds of Formula I are meant to encompass all possible stereoisomers and mixtures thereof.

Compounds of the present invention may containing a carbon-carbon double bond can exist as E and Z geometric isomers. Geometric isomers of compounds of Formula (I) containing one or more carbon-carbon double bonds are within the scope of the present invention.

Some of the compounds described herein may exist with different points of attachment of a hydrogen atom, referred to as tautomers. Such an example may be a ketone and its enol form known as keto-enol tautomers. The individual tautomers as well as mixture thereof are encompassed by the formulae set forth herein.

Compounds of the present invention may have unnatural ratios of atomic isotopes at one or more of their atoms. For example, the compounds may be radiolabeled with isotopes such as tritium or carbon-14. All isotopic variations of the compounds of the present invention, whether radioactive or not, are within the scope of the present invention.

The invention also encompasses active metabolites of compounds set forth herein.

In addition, prodrugs of the compounds described herein are also included within the scope of this invention. As used herein, the term "prodrug" means a compound which is converted within the body, e.g. by hydrolysis in the blood or by chemical conversion by metabolic processes, into its active form that has medical effects. As esters are readily hydrolyzed in vivo by plasma esterases, preferred prodrugs are esters of an alcohol or acid group of the drug. Pharmaceutically acceptable prodrugs are described in T. Higuchi and V. Stella, *Prodrugs as Novel Delivery Systems, Vol.* 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, which are incorporated herein by reference.

IV. Methods for Preparing Compounds

The present invention also provides methods for preparing compounds described herein.

The compounds of the invention can be prepared through a process consisting of synthetic transformations reported, for instance, in Michael Smith, Jerry March—March's Advanced Organic Chemistry: reactions mechanisms and structure—6th Edition, John Wiley & Sons Inc., 2007, which is herein incorporated as reference. It is well known to one of ordinary skill in the art that transformation of a chemical function into another may require that one or more reactive centers in the compound containing this function be protected in order to avoid undesired side reactions. Protection of such reactive centers, and subsequent de-protection at the end of the synthetic transformations, can be accomplished following standard procedures described, for instance, in Theodora W. Green and Peter G. M. Wuts—Protective Groups in Organic Synthesis, Fourth Edition, John Wiley & Sons Inc., 2006, which is herein incorporated as reference.

In one embodiment, a compound of the invention of Formula I can be obtained by reaction of a compound of Formula VIII, or a salt thereof, wherein $R^1$ and $R^2$ are each independently selected from the group consisting of hydrogen, alkyl, aryl, cycloalkyl, arylalkyl, and cycloalkylalkyl; or $R^1$ and $R^2$ form a cycloalkyl substituent together with the carbon to which they are attached, $R^3$ is selected from the group consisting of hydrogen and alkyl, and $R_4$, $R_5$, and $R_6$ are as defined above, with a compound of Formula IX,

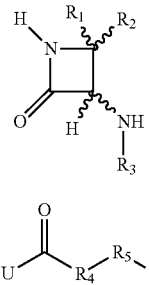

VIII

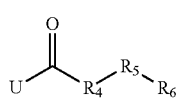

IX wherein U represents chlorine, hydroxyl, and $R_4$, $R_5$, and $R_6$ are as defined above.

A compound of Formula IX, wherein U represents chlorine, or hydroxyl is either a commercially available acyl chloride or carboxylic acid and can be prepared from suitable precursors, as known to a person skilled in the art, such as the corresponding carboxylic acids or anhydrides, according to standard synthetic methods as reported, for instance, in Michael Smith, Jerry March—March's Advanced Organic Chemistry: reactions mechanisms and structure—6th Edition, John Wiley & Sons Inc., 2007, and references cited therein, which is incorporated herein as reference.

A compound of Formula VIII wherein $R_1$, $R_2$ and $R_3$ are as defined above, can be obtained from a compound of Formula X, wherein PG1 represents a suitable nitrogen protecting group selected from, but not limited to, tert-butoxycarbonyl, benzyloxycarbonyl, and the like.

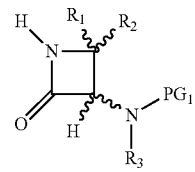

X

In another embodiment, a compound of the invention of Formula X can be obtained by selective removal of a endocyclic nitrogen protecting group from a compound of Formula XI, wherein $R_1$, $R_2$, $R_3$, PG1 are as defined above, and PG2 represents a suitable nitrogen protecting group selected from, but not limited to, hydroxyl, methoxyl, p-methoxyphenyl, O-methylbenzensulfonyl, t-butyldimethylsilyl, bis-(trimethylsilyl)-methyl, 2,4-dimethoxybenzyl, and the like.

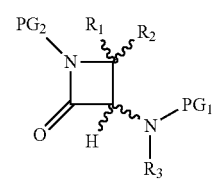

XI

A compound of Formula XI, as defined above, can be obtained by cyclization of a suitably protected compound of Formula XII, wherein $R_1$, $R_2$, $R_3$, PG1 and PG2 are as defined above.

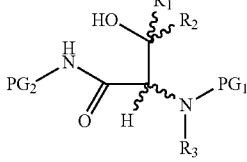

XII

A compound of Formula XII, as defined above, can be obtained by reaction of a compound of Formula XIII wherein $R_1$, $R_2$, $R_3$, and PG1 are as defined above, by treatment with a suitable amine in the presence of a carboxylic acid activating agent.

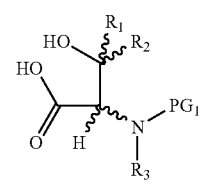

XIII

A compound of Formula XIII, as defined above, can be obtained by reaction of a compound of Formula XIV wherein $R_1$, $R_2$ and $R_3$ are as defined above, with a suitable carbamoylating agent, selected from, but not limited to, benzyl chloroformate, di-tert-butyl dicarbonate, and the like.

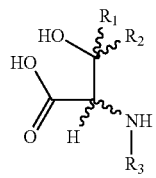

XIV

Amino acids of Formula XIV are either commercially available or can be obtained according to standard synthetic methods for the preparation of amino acids as described, for instance, in Blaskovich M. A., *Handbook on Syntheses of Amino Acids—General Routes to Amino Acids Oxford University Press, USA,* 2010, and references cited therein, which is herein incorporated as reference.

The synthesis of a compound of the invention, according to the synthetic processes described above, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified, using standard procedures, like column flash chromatography, reverse phase HPLC, preparative tin-layer-chromatography (TLC), crystallization, and the like.

The compounds described above can be prepared as exemplified in the following procedures.

A compound of the invention, as defined above, can be obtained by separating diastereoisomers or enantiomers of Formula I. In a typical procedure, diastereoisomers can be separated by fractional crystallization from a suitable solvent or by standard chromatographic techniques. The pair of enantiomers thus obtained may be separated into individual stereoisomers by standard techniques described, for example, in J. Jacques, A. Collet, S. H. Wilen—*Enantiomers, Racemates, and Resolutions*, John Wiley & Sons Inc., New York (N.Y.), 1981 and in G. Subramanian (Ed.), *Chiral Separation Techniques: a practical approach—Wiley*, Weinheim 2007, which are herein incorporated as reference. Alternatively, an enantiomer of a compound of Formula I may be obtained by stereospecific synthesis using optically pure starting materials of known configuration.

A pharmaceutically acceptable salt of a compound of Formula I, containing a basic group, can be obtained by dissolving said compound in a solvent like, for instance, acetonitrile, dioxane, tetrahydrofuran, ethanol, methanol, or dichloromethane, or mixtures thereof, and adding the proper amount of an inorganic or organic acid, dissolved in a suitable solvent such as, for instance, acetonitrile, dioxane, tetrahydrofuran, ethanol, methanol, or dichloromethane, or mixtures thereof, at a temperature ranging from −20° C. to room temperature. The salt is usually isolated by filtration of the precipitate obtained by a) cooling; b) addition of a precipitating solvent, usually diethyl ether or diisopropyl ether; or c) partial evaporation of the solvent.

A compound of Formula I, as defined as above, wherein $R^1$ and $R^2$ are each independently selected from the group consisting of hydrogen, alkyl, aryl, cycloalkyl, arylalkyl, and cycloalkylalkyl; or $R^1$ and $R^2$ form a cycloalkyl substituent together with the carbon to which they are attached, $R^3$ is selected from the group consisting of hydrogen and alkyl, and $R_4$, $R_5$, and $R_6$ are as defined as above, can be obtained by reaction of a compound of Formula VIII, as defined above, with a compound of Formula IX, as defined above, in the presence of a condensing agent selected from, but not limited to, O-(7-azabenzotriazol-1-yl)-N,N,N',N'-tetramethyluronium hexafluorophosphate, O-benzotriazole-N,N,N',N'-tetramethyl-uronium-hexafluorophosphate, benzotriazol-1-yl-oxytripyrrolidinophosphonium hexafluorophosphate, 1-hydroxybenzotrizole, and the like, in a suitable solvent, such as dichloromethane, tetrahydrofuran, dioxane, or mixtures thereof, in the presence of an organic base, such as di-isopropylethylamine or triethylamine, at a temperature ranging from −10° C. to 40° C., and for a period of time from 1 hour to 24 hours.

A compound of Formula VIII, as defined above, or a salt thereof, can be obtained by hydrogenolysis reaction of a compound of Formula X, wherein $R_1$, $R_2$ and $R_3$ are as defined above, and PG1 is benzyloxycarbonyl, either by treatment with hydrogen ($H_2$) gas in the presence of a suitable catalyst, such as 10% Pd/C, 10% Pd(OH)$_2$, and the like, or alternatively using 10% Pd on activated charcoal in the presence of cyclohexadiene, and the like, in a suitable solvent, such as dichloromethane, ethanol, tetrahydrofuran, dioxane, or ethylacetate, at a temperature ranging from −10° C. to room temperature, and for a period of time from 10 mins to 2 hours. A compound of Formula VIII is usually isolated as a salt after treatment with a dichloromethane, ethanol, or ethylacetate solution of acetic, hydrochloridric, or p-toluensulphonic acid, or the like.

A compound of Formula VIII, as defined above, or a salt thereof, can be obtained by reaction of a compound of Formula X, wherein $R_1$, $R_2$, $R_3$, are as defined above, PG1 is t-butoxycarbonyl, either by treatment with neat trifluoroacetic acid (TFA), or alternatively using hydrochloridric acid, and the like, in a suitable solvent, such as, ethanol, tetrahydrofuran, dioxane, or ethylacetate, at a temperature ranging from −10° C. to room temperature, and for a period of time from 10 mins to 24 hours. A compound of Formula VIII is usually isolated by precipitation as a salt after treatment with diethyl ether, dioxane, or the like.

A compound of the invention of Formula X, as defined above, can be obtained by selective deprotection of a compound of Formula XI wherein $R_1$, $R_2$, $R_3$, and PG1 are as defined above, and PG2 is a nitrogen protecting group, by treatment with ceric ammonium nitrate, samarium iodide, ozone/Na$_2$S$_2$O$_4$, NH$_3$(liq.)/Na, sodium stabilized in silica gel (Na-SG)/t-ButOH, cesium fluoride or the like, in a suitable solvent, such as acetonitrile, water, dioxane, tetrahydrofuran, methanol, diethylether, methyl t-butyl ether, cyclohexane, or mixtures thereof, at a temperature ranging from −10° C. to room temperature, and for a period of time from 10 mins to 2 hours.

A compound of Formula XI, as defined above, can be obtained by cyclization reaction of a compound of Formula XII, wherein $R_1$, $R_2$, $R_3$, PG1 and PG2 are as defined above, by previous activation of the hydroxyl group with suitable reagents, selected from, but not limited to, N,N'-sulfonyl-diimidazole, p-toluenesulfonyl chloride, methanesulfonyl chloride, and the like, in a solvent, such as dioxane, tetrahydrofuran, acetone, acetonitrile, N,N-dimethylformamide, or mixtures thereof, in the presence of an inorganic base, such as sodium hydride, potassium carbonate, or sodium hydrogen carbonate, at a temperature ranging from 0° C. to 50° C., and for a period of time from 1 hours to 24 hours.

A compound of Formula XII, as defined above, can be obtained by reaction of a compound of Formula XIII, wherein $R_1$, $R_2$, $R_3$, PG1 and PG2 are as defined above, with suitable amines, selected from, but not limited to, 4-methoxyaniline, methoxyamine, benzylamine, in the presence of a carboxyl-activating agent, such as 1-ethyl-3-(3-dimethylaminopropyl)-carbodiimide, N,N'-dicyclohexylcarbodiimide, N,N'-diisopropylcarbodiimide, and the like, in a solvent, such as water, tetrahydrofuran, dimethylformamide, dichloromethane or mixtures thereof, at a temperature ranging from −10° C. to room temperature, and for a period of time from 12 hours to 24 hours.

A compound of Formula XIII, as defined above, can be obtained by reaction of a compound of Formula XIV, wherein $R_1$, $R_2$ and $R_3$ are as defined above, with a suitable carbamoylating agent, selected but not limited to, benzyl chloroformate, di-tert-butyl dicarbonate, and the like. The reaction can be performed in a suitable solvent, such as dioxane, tetrahydrofuran, dichloromethane, acetonitrile, N,N-dimethylformamide, or mixtures thereof, in the presence of a suitable organic or inorganic base, such as triethylamine, di-isopropylethylamine or sodium hydrogen carbonate, and at a temperature ranging from −10° C. to 60° C., and for a period of time from 1 hour to 24 hours.

V. Pharmaceutical Compositions

The invention provides pharmaceutical compositions of the compounds described herein for modulation of the levels of palmitoylethanolamine in a subject. The pharmaceutical compositions of the present invention encompass compositions made by admixing a compound of the present invention and a pharmaceutically acceptable carrier and/or excipient or diluent. Such compositions are suitable for pharmaceutical use in an animal or human.

The pharmaceutical compositions of the present invention include a compound described herein, or a pharmaceutically acceptable salt thereof, as an active ingredient and a pharmaceutically acceptable carrier and/or excipient or diluent. A pharmaceutical composition may optionally contain other therapeutic ingredients.

The compounds of the present invention can be combined as the active ingredient in intimate admixture with a suitable pharmaceutical carrier and/or excipient according to conventional pharmaceutical compounding techniques. Any carrier and/or excipient suitable for the form of preparation desired for administration is contemplated for use with the compounds disclosed herein.

The compositions include compositions suitable for topical, parenteral, pulmonary, nasal, rectal or oral administration. The most suitable route of administration in any given case will depend in part on the nature and severity of the conditions being treated and on the nature of the active ingredient.

Some preferred compositions include compositions suitable for topical, subcutaneous, and pulmonary, in the form of nasal or buccal inhalation administration.

Other preferred compositions include compositions suitable for systemic (enteral or parenteral) administration. The systemic administration includes the oral, rectal, sublingual, sublabial administration.

The compositions may be prepared by any of the methods well-known in the art of pharmacy.

Compositions for topical administration include, but are not limited to, ointments, creams, lotions, solutions, pastes, gels, sticks, liposomes, nanoparticles, patches, bandages and wound dressings. In certain embodiments, the topical formulation comprises a penetration enhancer.

Compositions for pulmonary administration include, but are not limited to, dry powder compositions consisting of the powder of a compound described herein, or a salt thereof, and the powder of a suitable carrier and/or lubricant. The compositions for pulmonary administration can be inhaled from any suitable dry powder inhaler device known to a person skilled in the art.

Compositions for systemic administration include, but are not limited to, dry powder compositions consisting of the powder of a compound of Formula I, or a salt thereof, and the powder of a suitable carrier and/or excipient. The compositions for systemic administration can be represented by, but not limited to, tablets, capsules, pills, syrups, solutions, suspensions, films and suppository.

Administration of the compositions is performed under a protocol and at a dosage sufficient to reduce the inflammation and pain in the subject.

In some embodiments, in the pharmaceutical compositions of the present invention the active principle or active principles are generally formulated in dosage units. The dosage unit may contain from 0.1 to 1000 mg of a NAAA inhibitor per dosage unit.

In some embodiments, the amounts effective for topical or systemic administration will depend on the severity of the disease, disorder or condition, previous therapy, the individual's health status and response to the drug. In some embodiments, the dose is in the range from 0.001% by weight to about 60% by weight of the formulation.

When used in combination with one or more other active ingredients, the compound of the present invention and the other active ingredients may be used in lower doses than when each is used singly.

With respect to formulations with respect to any variety of routes of administration, methods and formulations for the administration of drugs are disclosed in *Remington: The Science and Practice of Pharmacy*, 21*st Edition*, Lippincott Williams & Wilkins Eds., 2005; and in *Ansel's Pharmaceutical Dosage Forms and Drug Delivery Systems*, 8*th Edition*. Lippincott Williams & Wilkins Eds., 2005, which are herein incorporated as reference.

VI. Administration

The compounds of the invention may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of the invention can be effective over a wide dosage range. For example, in the treatment of adult humans, dosages from about 1 to about 1000 mg, about 100 to about 500 mg, about 10 to about 100 mg, about 1 to 10 mg may be needed. These dosages may adjusted as to amounts and/or a schedule as needed to achieve relief (e.g., 4, 6, 8, 12 or 24 hour intervals; 1-, 2-, 3-, or 4-times per day). Depending on the compound, doses of the 0.05 to about 100 mg, or from about 0.1 to about 100 mg per day may be used. In choosing a regimen for patients, it may frequently be necessary to begin with a dosage of from about 2 to about 70 mg per day and when the condition is under control to reduce the dosage as low as from about 0.1 to about 10 mg per day. For example, in the treatment of adult humans, dosages from about 0.05 to about 100 mg, preferably from about 0.1 to about 100 mg, per day may be used. The exact dosage will depend upon the mode of administration, the compound of the invention involved, on the therapy desired, form in which administered, the subject to be treated and the body weight of the subject to be treated, and the preference and experience of the physician or veterinarian in charge.

Generally, the compounds of the present invention can be dispensed in unit dosage form comprising preferably from about 0.1 to about 1000 mg of active ingredient together with a pharmaceutically acceptable carrier per unit dosage. Dosage forms suitable for oral, nasal, pulmonary or transdermal administration may comprise from about 0.001 mg to about 100 mg, or from about 0.01 mg to about 50 mg of the compounds admixed with a pharmaceutically acceptable carrier or diluent. For storage and use, these preparations preferably contain a preservative to prevent the growth of microorganisms.

Kits providing a unit dosage of the compounds and compositions set forth herein are contemplated as within the present invention. Kits providing many unit dosages of the compounds and compositions set forth herein are contemplated as within the present invention. Still further, kits providing several unit dosages of the compounds and compositions set forth herein are contemplated as within the present invention. In some embodiments, the kits of the present invention include a unit dosage of a pharmaceutical composition of a compound set forth herein. In certain embodiments, the kits of the present invention include many unit dosages of a pharmaceutical composition of a compound set forth herein. In certain other embodiments, the kits of the present invention include a unit dosage of a pharmaceutical composition set forth herein.

Administration of an appropriate amount the candidate compound may be by any means known in the art such as, for example, oral or rectal, parenteral, intraperitoneal, intravenous, subcutaneous, subdermal, intranasal, or intramuscular. In some embodiments, administration is transdermal. In some other embodiments, the administration is for dermal delivery. An appropriate amount or dose of the candidate compound may be determined empirically as is known in the art. An appropriate or therapeutic amount is an amount sufficient to effect a loss of body fat or a loss in body weight in the animal over time. The candidate compound can be administered as often as required to effect a loss of body fat or loss in body weight, for example, hourly, every six, eight, twelve, or eighteen hours, daily, or weekly Formulations suitable for oral administration can consist of (a) liquid solutions, such as an effective amount of the active ingredient suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Injection solutions and suspensions can be prepared from sterile powders, granules, and tablets of the kind previously described. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

With respect to transdermal or dermal delivery routes of administration, methods for transdermal administration of drugs are disclosed in Remington's Pharmaceutical Sciences, Gennaro AR ed. 20th edition, 2000: Williams & Wilkins PA, USA. Dermal or skin patches are a preferred means for transdermal delivery of the compounds of the invention. Patches preferably provide an absorption enhancer such as DMSO to increase the absorption of the compounds. Other methods for transdermal drug delivery are disclosed in U.S. Pat. Nos. 5,962,012, 6,261,595, and 6,261,595. Each of which is incorporated by reference in its entirety.

Preferred patches include those that control the rate of drug delivery to the skin. Patches may provide a variety of dosing systems including a reservoir system or a monolithic system, respectively. The reservoir design may, for example, have four layers: the adhesive layer that directly contacts the skin, the control membrane, which controls the diffusion of drug molecules, the reservoir of drug molecules, and a water-resistant backing Such a design delivers uniform amounts of the drug over a specified time period, the rate of delivery has to be less than the saturation limit of different types of skin.

The monolithic design, for example, typically has only three layers: the adhesive layer, a polymer matrix containing the compound, and a water-proof backing. This design brings a saturating amount of drug to the skin. Thereby, delivery is controlled by the skin. As the drug amount decreases in the patch to below the saturating level, the delivery rate falls.

Compounds of the invention may be used in combination with other compounds of the invention or with other drugs that may also be useful in the treatment, prevention, suppression of a neurological or psychological disorder. Such other drugs may be administered, by a route and in an amount commonly used therefor, contemporaneously or sequentially with a compound of the invention. When a compound of the invention is used contemporaneously with one or more other drugs, a pharmaceutical composition in unit dosage form containing such other drugs and the compound is preferred. When used in combination with one or more other active ingredients, the compound of the present invention and the other active ingredients may be used in lower doses than when each is used singly.

In the pharmaceutical compositions of the present invention for oral, sublingual, subcutaneous, intramuscular, intravenous, transdermal, dermal delivery, local or rectal administration, the active principle, by itself or in association with another active principle, can be administered to animals and humans in unit forms of administration mixed with conventional pharmaceutical carriers. The appropriate unit forms of administration include oral forms such as tablets, gelatin capsules, powders, granules and solutions or suspensions to be taken orally, sublingual and buccal forms of administration, aerosols, implants, subcutaneous, intramuscular, intravenous, intranasal or intraocular forms of administration and rectal forms of administration.

In other embodiments, the pharmaceutical compositions of the present invention, the active principle or active principles are generally formulated in dosage units. The dosage unit may contain from 0.1 to 1000 mg, advantageously from 1 to 500 mg and preferably from 2 to 200 mg per dosage unit for daily administration.

In certain embodiments, the pharmaceutical compositions of the present invention are suitable for dermal delivery.

VII. Method of Use

In some embodiments, the compounds described herein, and their pharmaceutical compositions and methods of administering them are useful in treating acute inflammation, chronic inflammation, pain (including acute pain, acute inflammatory pain, chronic inflammatory pain, and neuropathic pain), and other disorders in which decreased levels of NAE are associated with the disorder. The treatment may be prophylactic or therapeutic.

In other embodiments, the pharmaceutical compositions of the present invention, the active principle or active principles are generally formulated in dosage units. The dosage unit may contain from 0.1 to 1000 mg, advantageously from 1 to 500 mg and preferably from 2 to 200 mg per dosage unit.

NAAA inhibition can increase PEA and OEA levels to inhibit peripheral inflammation and mast cell degranulation (Mazzari et al., *European Journal of Pharmacology* 1996, 300, 227-36; Berdishev et al., *Life Science* 1998, 63, 125-129; D'Agostino et al., *Journal of Pharmacology and Experimental Therapeutics* 2007, 322, 1137-1143), as well as to exert antinociceptive effects in rats and mice (Calignano et al., *Nature* 1998, 394, 277-281; Calignano et al., *European Journal of Pharmacology* 2001, 419, 191-198). These properties have been shown to be dependent on PPAR-α expression, and PEA and OEA activate this nuclear receptor with high potency (Lo Verme et al., *Molecular Pharmacology* 2005, 67, 15-19; Lo Verme et al., *Journal of Pharmacology and Experimental Therapeutics* 2006, 319, 1051-1061). In the carrageenan-induced paw edema and phorbol ester-induced ear edema models, PEA applied as a drug attenuates inflammation in wild-type mice, but has no effect in mice lacking PPAR-α(see LoVerme et al., *Molecular Pharmacology* 2005, 67, 15-19). PEA was also found to suppress pain behaviors in mice induced by chemical tissue injury, nerve damage, or inflammation (see LoVerme et al., *Journal of Pharmacology and Experimental Therapeutics* 2006, 319, 1051-1061). In addition to the pharmacological activities shown in animal models, PEA has been reported to attenuate skin inflammation in humans (Kemeny et al., *Skin Pharmacology and Physiology* 2007, 20, 155-161). Certain methods of treating pain and inflammation by inhibiting NAAA have been disclosed in the Patent Application WO2009/049238. Some compounds disclosed in WO2009/049238 have been shown to prevent the carrageenan- and LPS-induced reduction in PEA and OEA levels in leukocytes and RAW264.7 macrophages, respectively, and attenuate inflammation and tissue damage produced in mice by traumatic spinal cord injury (Solorzano et al., *Proceedings of the National Academy of Science USA* 2009, 106, 20966-20971; Solorzano et al., *Journal of Medicinal Chemistry* 2010, 53, 5770-5781). Each of these publications and patent applications are specifically incorporated herein by reference particularly with respect to the biological properties and activities of NAAA inhibitors and PEA/OEA as well as of their therapeutic uses and their biological assay methods which can be used to assess the anti-inflammatory and anti-pain as well as the other therapeutic actions of the NAAA inhibitors of the present invention.

The compounds and compositions described herein are useful for treating arthritis, wherein arthritis may include osteoarthritis, rheumatoid arthritis, gout, fibromyalgia, general arthritis, psoriatic arthritis, systemic lupus erythematosus, or septic arthritis.

The compounds and compositions described herein are useful for treating asthma, wherein asthma may include exercise-induced asthma, asthma due to an allergy, cough-variant asthma, occupational asthma, or nocturnal asthma.

The compounds and compositions described herein are useful for treating neurogenerative inflammation, wherein neurodegenerative inflammation may include Parkinson's disease or multiple sclerosis.

The compounds and compositions described herein are useful for treating neurodermatitis.

The irritable bowel syndrome (IBS) described herein may include, but is not limited to, IBS with constipation, IBS with diarrhea, or IBS with alternating constipation and diarrhea.

The inflammatory bowel disease (IBD) described herein may include Crohn's disease, ulcerative colitis, ileocolitis, ileitis, gastroduodenal Crohn's disease, or jejunoileitis

VIII. Inflammation and Inflammatory Pain

In some embodiments, the compounds described herein and their pharmaceutical compositions may be administered in therapeutically effective amounts to alleviate or treat inflammation in a subject. The treatment may be prophylactic or therapeutic. The treatment may be administered in a combination therapy with another pain reliever or anti-inflammatory agent. In some embodiments, the pain is a pain caused by inflammation or injury of a tissue. Inflammatory pain develops in response to tissue damage occurring from the noxious stimuli. The inflammation is associated with disease states including, but not limited to, acute inflammation, chronic inflammation, arthritis, rheumatoid arthritis, asthma, chronic obstructive pulmonary disease (COPD), adult respiratory disease, chronic bronchitis, emphysema, cough, inflammatory bowel disease, ulcerative colitis, lupus, graft vs. host reaction (i.e., graft vs. host disease), acute and chronic allograft rejection, acute respiratory distress syndrome, osteoarthritis, multiple sclerosis, restinosis, cystic fibrosis, crystal induced arthritis, ocular inflammation, hyperoxia-induced inflammations, dyslipidemia, myofasciitis, carpal tunnel, Alzheimer's disease, Parkinson's disease. In embodiments, the inflammation may be associated with disease states including, but not limited to, acute inflammation, chronic inflammation, arthritis, rheumatoid arthritis, asthma, chronic obstructive pulmonary disease (COPD), adult respiratory disease, chronic bronchitis, emphysema, cough, inflammatory bowel disease, ulcerative colitis, Crohn's disease, ileocolitis, ileitis, gastroduodenal Crohn's disease, jejunoileitis, lupus, graft vs. host reaction (i.e., graft vs. host disease), acute and chronic allograft rejection, acute respiratory distress syndrome, osteoarthritis, multiple sclerosis, restinosis, cystic fibrosis, crystal induced arthritis, ocular inflammation (including dry eye), corneal damage, hyperoxia-induced inflammations, dyslipidemia, myofasciitis, carpal tunnel, Alzheimer's disease, Parkinson's disease.

In some embodiments, the present invention provides a method of treating a mammal suffering from an inflammatory condition comprising administering to the mammal a compound having the structure selected from the group consisting of Formula I, II, III, IV, V, VI, and VII.

In some other embodiments, the present invention provides a method set forth herein wherein the inflammatory condition is osteoarthritis, rheumatoid arthritis, asthma, chronic obstructive pulmonary disease (COPD), adult respiratory disease, chronic bronchitis, inflammatory bowel disease, ulcerative colitis, lupus, graft vs. host reaction (i.e., graft vs. host disease), acute and chronic allograft rejection, acute respiratory distress syndrome, multiple sclerosis, restinosis, cystic fibrosis, crystal induced arthritis, ocular inflammation (including dry eye), corneal damage, hyperoxia-induced inflammation, myofascitis, polymyositis, carpal tunnel, sprains, contusions, dental pain, vasculitis, or periodontitis.

In some embodiments, the present invention provides that the inflammatory condition is contact dermatitis, atopic dermatitis, seborrhoic dermatitis, eczema, urticaria, rosacea, acne, psoriasis, lichen, psoriatic arthritis acne, skin burns deriving from various origins, surgical skin incisions, or delayed skin healing induced by diabetes, immunosuppression or other causes.

The compositions of the present invention can also be useful for treating the inflammation associated with neurodegenerative disorders such as ALS, Parkinson's, and Alzheimers disease.

The compositions of the present invention can also be useful for treating skin inflammation disorders. The compositions of the present invention can be applied locally, topically, or systemically for the treatments contemplated herein.

IX. Pain

In some embodiments, the compounds described herein and their pharmaceutical compositions may be administered in therapeutically effective amounts to alleviate or treat pain in a subject in need thereof. The treatment may be prophylactic or therapeutic. The treatment may be administered in a combination therapy with another pain reliever or anti-inflammatory agent. The treatment may be also administered in a combination with PEA and/or OEA, or other NAAA substrates with similar anti-inflammatory properties.

The compositions of the present invention can also be useful for treating neurodegenerative disorders such as ALS, Parkinson's, and Alzheimers disease.

In some embodiments, the pain is associated with disease states including, but not limited to migraine, sinus headaches, trigeminal disease, dental pain, multiple sclerosis, sarcoidosis, polymyositis, gingivitis, swelling occurring after injury, pre-term labor, sprains, contusions, surgery (prophylactically and therapeutically), trauma, bone damage, and cancer.

In other embodiments, the pain can be a neuropathic pain selected from the group of, but not limited to, post herpetic neuralgia, post trigeminal neuralgia, diabetic neuropathy, neuropathic low back pain, peripheral or polyneuropathic pain, toxic neuropathy, chronic neuropathy caused by chemotherapeutic agents, retinopathy of prematurity, diabetic retinopathy, polymyositis, vasculitis, and periodontitis.

In some embodiments, the present invention provides a method of treating a mammal suffering from a painful or pruritogenic pathological state not attributable to inflammation comprising administering to the mammal a compound having the structure selected from the group consisting of Formula I, II, III, IV, V, VI, and VII.

In some embodiments, the present invention provides that the pathological state to be treated is post herpetic neuralgia, trigeminal neuralgia, causalgia, diabetic neuropathy, neuropathic low back pain, peripheral or polyneuropathic pain, toxic neuropathy, chronic neuropathy caused by chemotherapeutic and antiviral agents, or pruritus induced by uremia, malignancies of various origin, polycythemia, jaundice or cholestasis, iron deficiency, athlete's foot, xerosis, wound healing, thyroid illness, hyperparathyroidism, or menopause.

X. Dermal Diseases, Disorders or Conditions

In some embodiments, the compositions of the invention may be administered in therapeutically effect amounts to alleviate or treat dermal diseases, disorders or conditions in a subject. The treatment may be prophylactic or therapeutic. The treatment may be administered in a combination therapy with another agent used in the treatment of dermatological diseases, disorders or conditions. In some embodiments, dermal diseases, disorders or conditions include, but are not limited to, contact dermatitis, atopic dermatitis, eczema, urticaria, rosacea, acne, psoriasis, pruritis, lichen, psoriatic arthritis acne, scarring, skin wound healing, skin burns deriving from various origins, such as sunburns or radiation therapy burns, and of various severities (first degree burn, second degree burn, third degree burn, fourth degree burns), scleroderma, solar keratosis, squamous cell carcinoma, and melanoma.

In some embodiments, the present invention provides a method of treating a mammal suffering from a neurodegenerative disorder, comprising administering to the mammal a compound having the structure selected from the group consisting of Formula I, II, III, IV, V, VI, and VII.

In some embodiments, the present invention provides that the neurodegenerative disorder is Alzheimer's dementia, Parkinson's disease, Huntington's disease, Amytrophic Lateral Sclerosis, or macular degeneration.

In other embodiments, the present invention provides a method of inhibiting NAAA comprising contacting the NAAA in vitro with a compound having the structure selected from the group consisting of Formula I, II, III, IV, V, VI, and VII.

In other embodiments, the present invention provides a method, as set forth herein, wherein the compound is selected from the group consisting of

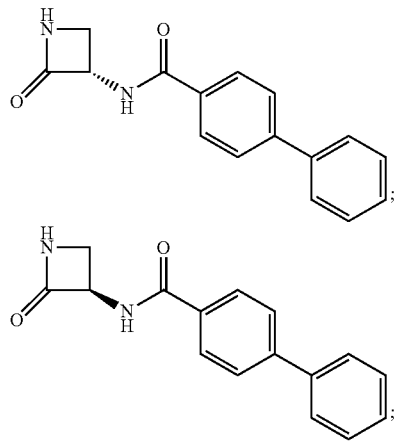

33
-continued
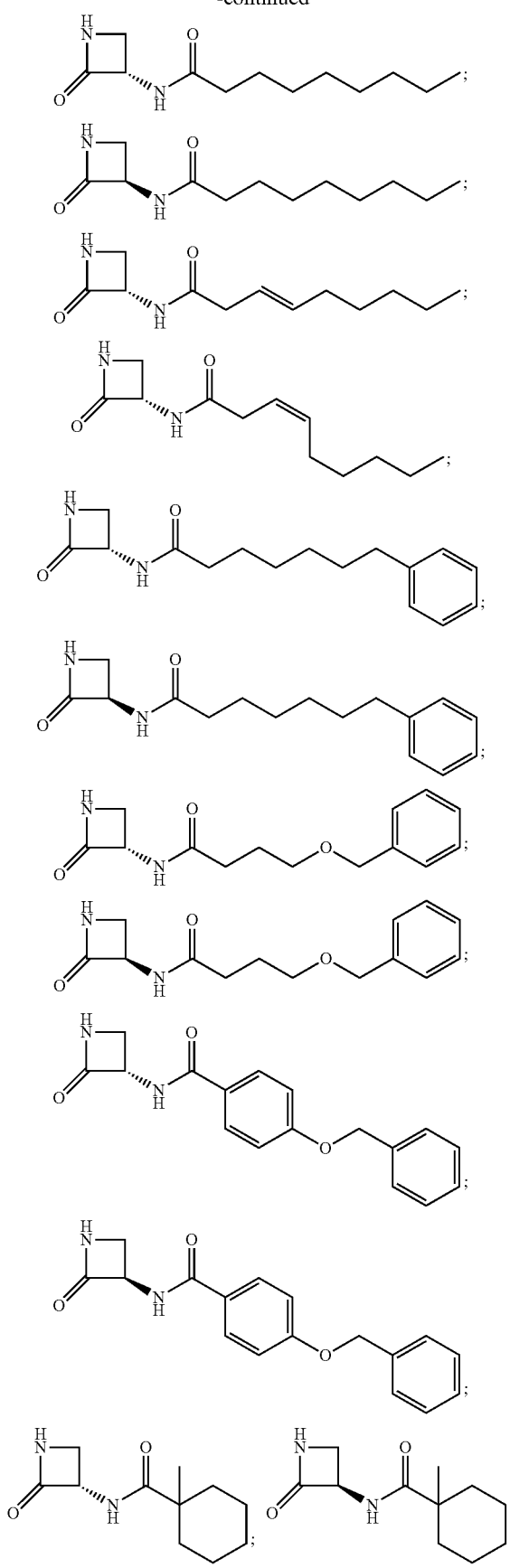
34
-continued
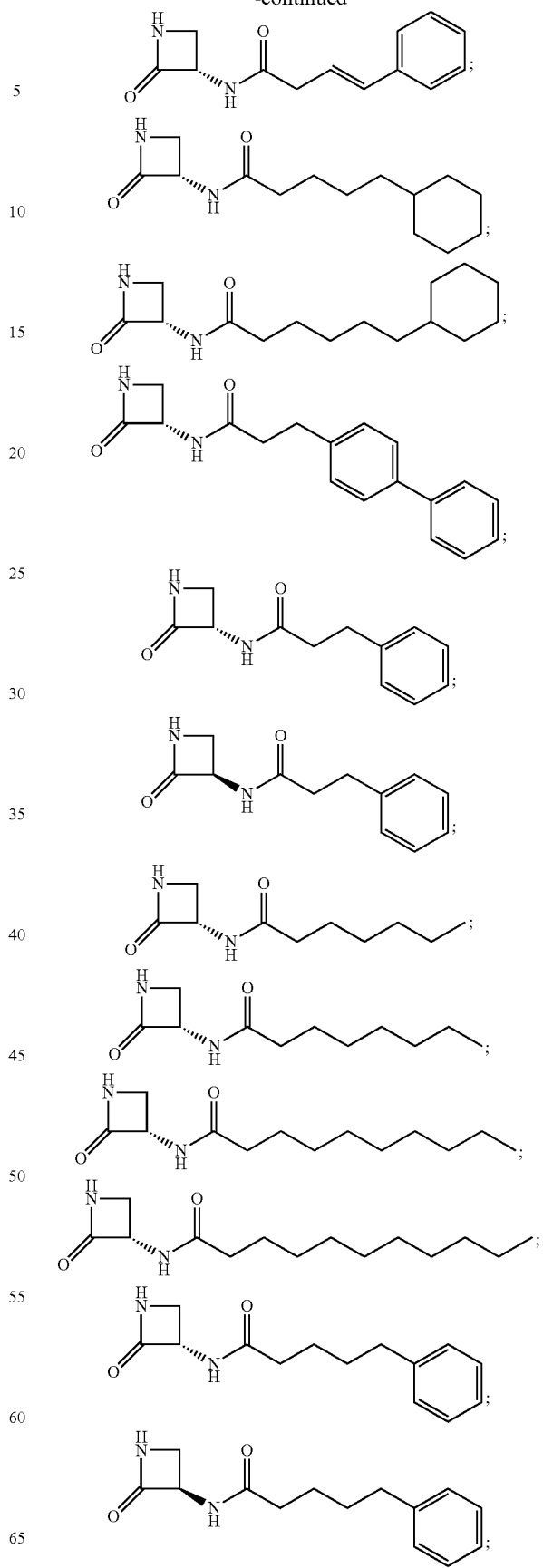

-continued

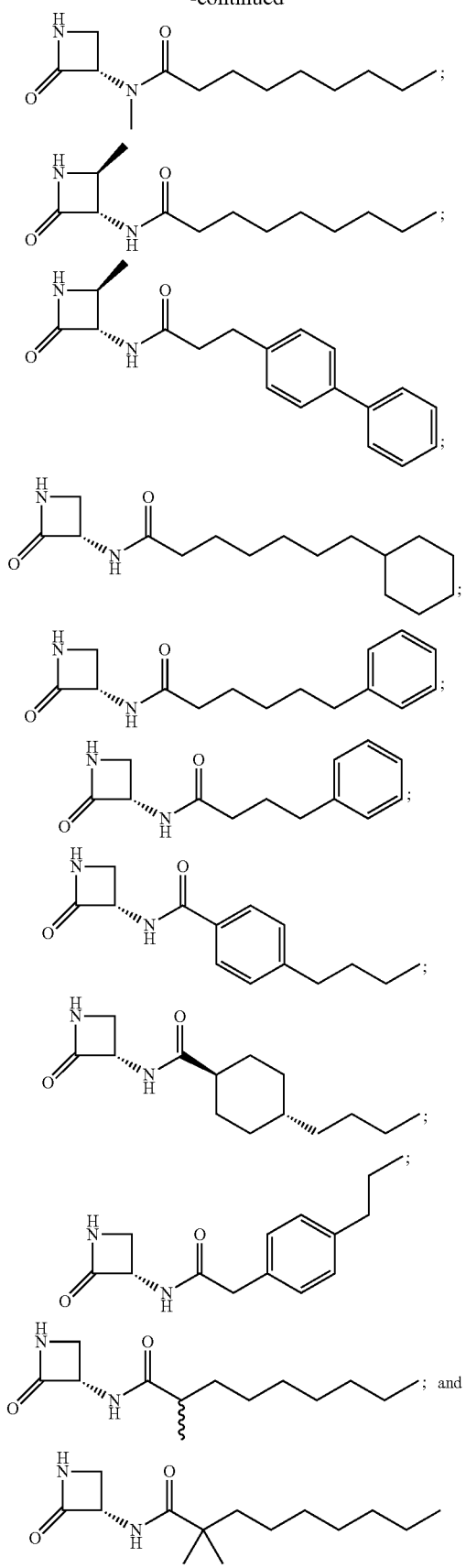

XI. Patient Populations

The compounds and compositions described herein are useful for treating the above diseases, conditions, and disorders. The present invention includes methods for treating such diseases, conditions, and disorders, including the treatment for pain and/or inflammation.

In some embodiments, the methods include administering the compounds and compositions of the present invention to adults (e.g, men, women) or children under the age of 18, 16, 14, 12 or 10 years. The women may be of child-bearing age or pregnant.

The compounds may be administered on any suitable schedule. In some embodiments, the compounds and compositions set forth herein are administered daily. In other embodiments, the compounds and compositions set forth herein can be administered two, three, four or five times a day. In still other embodiments, are administered weekly, twice, three, four or more times a week. The compound may be administered as needed to provide symptomatic relief (e.g., reduce the pain or inflammation as needed by the patient according to their perception of the pain or inflammation) or to reduce the disease process.

XII. Additional Embodiments

1. A compound having the structure of Formula I:

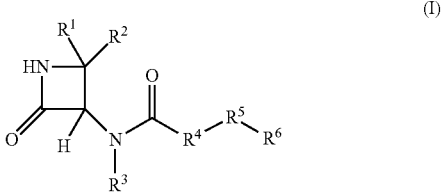

(I)

wherein: $R^1$ and $R^2$ are each independently selected from the group consisting of hydrogen, alkyl, aryl, cycloalkyl, arylalkyl, and cycloalkylalkyl; or $R^1$ and $R^2$ form a cycloalkyl substituent together with the carbon to which they are attached; $R^3$ is selected from the group consisting of hydrogen and alkyl; $R^4$ is selected from the group consisting of alkyl, alkenyl, alkynyl, aryl, cycloalkyl, heteroaryl, heterocyclyl, heteroarylalkyl, and heterocycloalkyl; $R^5$ is absent or is selected from the group consisting of alkyl, alkoxy, aryl, aryloxy, cycloalkyl, —O—, heteroaryl, and heterocyclyl; $R^6$ is absent or is selected from the group consisting of hydrogen, alkyl, alkoxy, aryl, aryloxy, arylalkyloxy, arylalkyl, cycloalkyl, heteroaryl, cycloalkyloxy, heterocycloalkyloxy and heterocyclyl; wherein $R^1$, $R^2$, $R^3$, $R^4$, $R^5$, and $R^6$ are each independently optionally substituted with 1-4 substituents selected from the group consisting of hydrogen, lower alkyl, lower alkoxy, aryl, $NR^aR^b$, cyano, halogen, and hydroxyl; wherein $R^a$ and $R^b$ are each independently selected from the group consisting of hydrogen and alkyl; or a pharmaceutically acceptable salt, ester, or prodrug thereof.

2. A compound of embodiment 1, having the structure selected from the group of Formulae II, III, IV, V, VI, and VII:

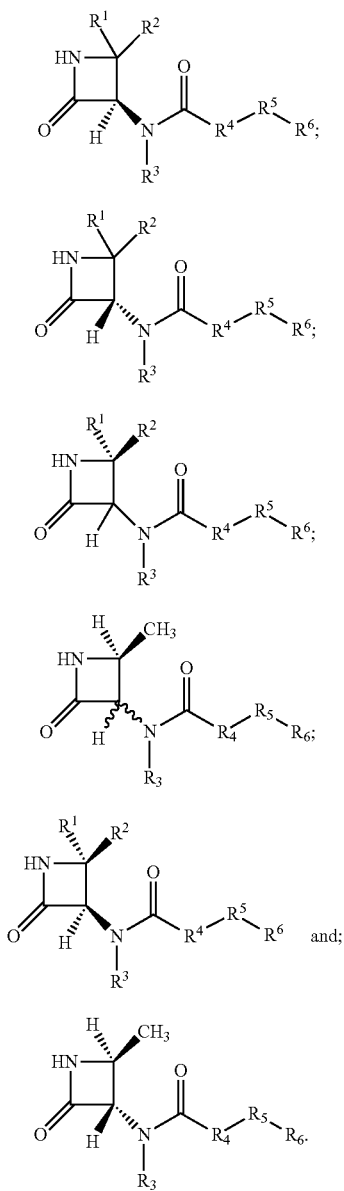

3. A compound of one of embodiments 1 to 2, wherein $R^1$ and $R^2$ are both hydrogen.

4. A compound of one of embodiments 1 to 2, wherein $R^1$ and $R^2$ are both methyl.

5. A compound of one of embodiments 1 to 2, wherein $R^1$ is hydrogen and $R^2$ is methyl.

6. A compound of one of embodiments 1 to 5, wherein $R^3$ is hydrogen or methyl.

7. A compound of one of embodiments 1 to 2, wherein $R^1$ and $R^2$ are both H, both methyl, or $R^1$ is hydrogen and $R^2$ is methyl; and wherein $R^3$ is methyl.

8. A compound of one of embodiments 1 to 7, wherein $R^4$ is aryl, phenyl, alkyl, alkenyl, or cycloalkyl.

9. A compound of embodiment 7, wherein $R^4$ is aryl, phenyl, alkyl, alkenyl, or cycloalkyl.

10. A compound of one of embodiments 1 to 8, wherein $R^4$ is selected from the group consisting of methyl, ethyl, i-propyl, n-propyl, n-butyl, t-butyl, i-butyl, pentyl, hexyl, heptyl, octyl, nonyl, decyl, undecyl, and dodecyl.

11. A compound of embodiment 9, wherein $R^4$ is selected from the group consisting of methyl, ethyl, i-propyl, n-propyl, n-butyl, t-butyl, i-butyl, pentyl, hexyl, heptyl, octyl, nonyl, decyl, undecyl, and dodecyl.

12. A compound of one of embodiments 1 to 8, wherein $R^4$ is selected from the group consisting of propenyl, 1-propenyl, 2-propenyl, 1-butenyl, 2-butenyl, 1-pentenyl, 2-pentenyl, 3-pentenyl, 1-hexenyl, 2-hexenyl, 3-hexenyl, 1-heptenyl, 2-heptenyl, 3-heptenyl, 4-heptenyl, 1-octenyl, 2-octenyl, 3-octenyl, and 4-octenyl.

13. A compound of embodiment 9, wherein $R^4$ is selected from the group consisting of propenyl, 1-propenyl, 2-propenyl, 1-butenyl, 2-butenyl, 1-pentenyl, 2-pentenyl, 3-pentenyl, 1-hexenyl, 2-hexenyl, 3-hexenyl, 1-heptenyl, 2-heptenyl, 3-heptenyl, 4-heptenyl, 1-octenyl, 2-octenyl, 3-octenyl, and 4-octenyl.

14. A compound of one of embodiments 1 to 8, wherein $R^4$ is cyclohexyl or 1-methyl-cyclohexyl.

15. A compound of embodiment 9, wherein $R^4$ is cyclohexyl or 1-methyl-cyclohexyl.

16. A compound of one of embodiments 1 to 15, wherein $R^5$ is absent.

17. A compound of one of embodiments 1 to 15, wherein $R^5$ is selected from the group consisting of alkyl, alkoxy, or aryl.

18. A compound of one of embodiments 1 to 15, wherein $R^5$ is selected from the group consisting of methyl, ethyl, propyl, and butyl.

19. A compound of one of embodiments 1 to 15, wherein $R^5$ is selected from the group consisting of methoxy, ethoxy, propoxy, and butoxy.

20. A compound of one of embodiments 1 to 15, wherein $R^5$ is phenyl.

21. A compound of one of embodiments 1 to 20, wherein $R^6$ is alkyl, aryl, or cycloalkyl.

22. A compound of one of embodiments 1 to 20, wherein $R^6$ is selected from the group consisting of methyl, ethyl, i-propyl, n-propyl, n-butyl, t-butyl, i-butyl, pentyl, hexyl, heptyl, octyl, nonyl, decyl, undecyl, and dodecyl.

23. A compound of one of embodiments 1 to 20, wherein $R^6$ is selected from the group consisting of cyclobutyl, cyclopentyl, and cyclohexyl.

24. A compound of one of embodiments 1 to 20, wherein $R^6$ is phenyl or benzyloxy.

25. A compound of one of embodiments 1 to 15 and 21 to 24, wherein $R^5$ is selected from the group consisting of alkyl, alkoxy, and aryl.

26. A compound of embodiment 9, wherein $R^5$ is selected from the group consisting of alkyl, alkoxy, or aryl.

27. A compound of embodiment 9, wherein $R^6$ is alkyl, aryl, or cycloalkyl.

28. A compound of one of embodiments 1 to 7, wherein $R^4$-$R^5$-$R^6$ is selected from the group consisting of biphenyl, octyl, trans-2-octenyl, cis-2-octenyl, hexyl-phenyl, propyl-benzyloxy, 4-benzyloxy-phenyl, 1-methyl-cyclohexyl, 3-phenyl-2-propenyl, butyl-cyclohexyl, pentyl-cyclohexyl, hexyl-cyclohexyl, 2-biphenyl-ethyl, 2-phenyl-ethyl, 4-phenyl-butyl, 5-phenyl-pentyl, pentyl, hexyl, heptyl, octyl, nonyl, and decyl.

29. A compound of embodiment 1, wherein the compound is selected from the group consisting of

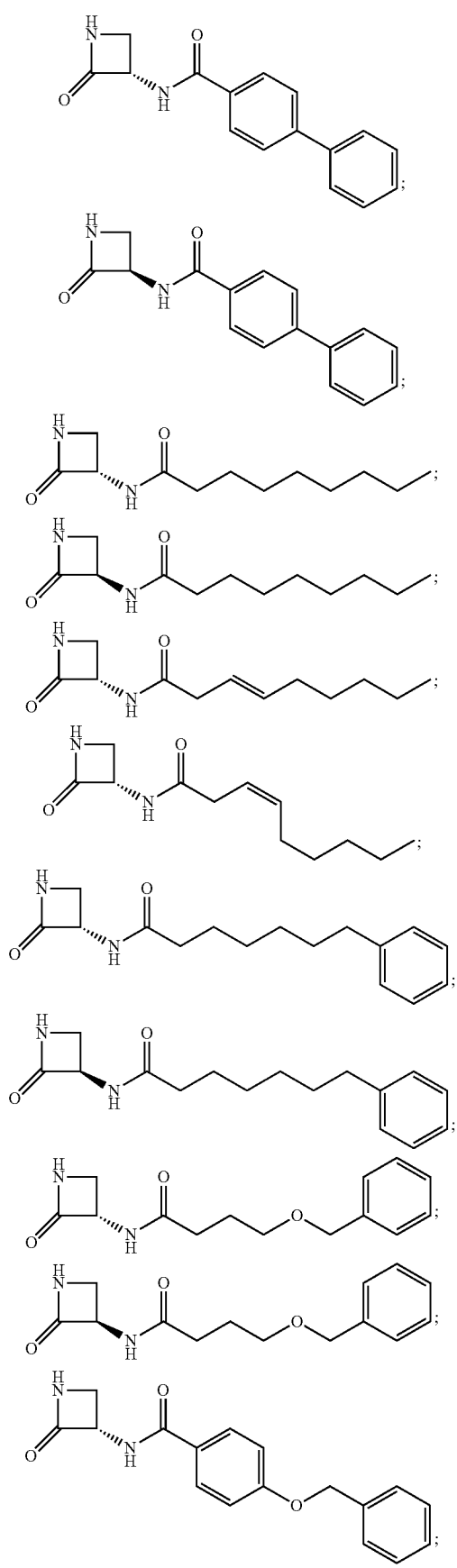
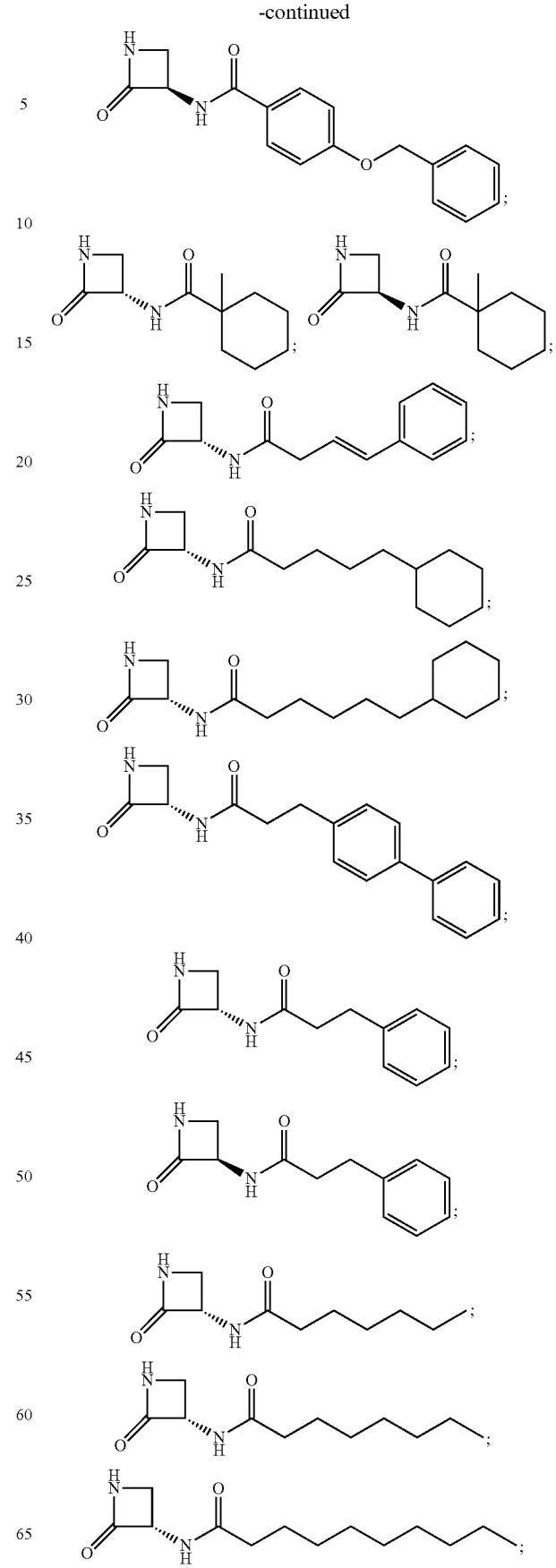

-continued

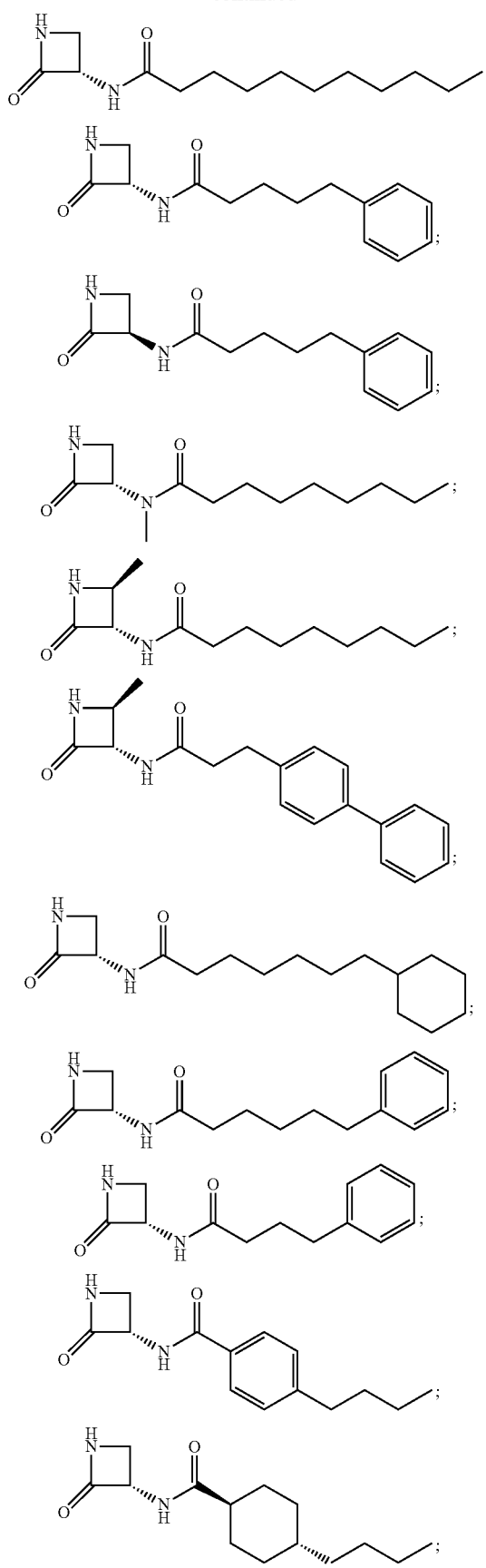

-continued

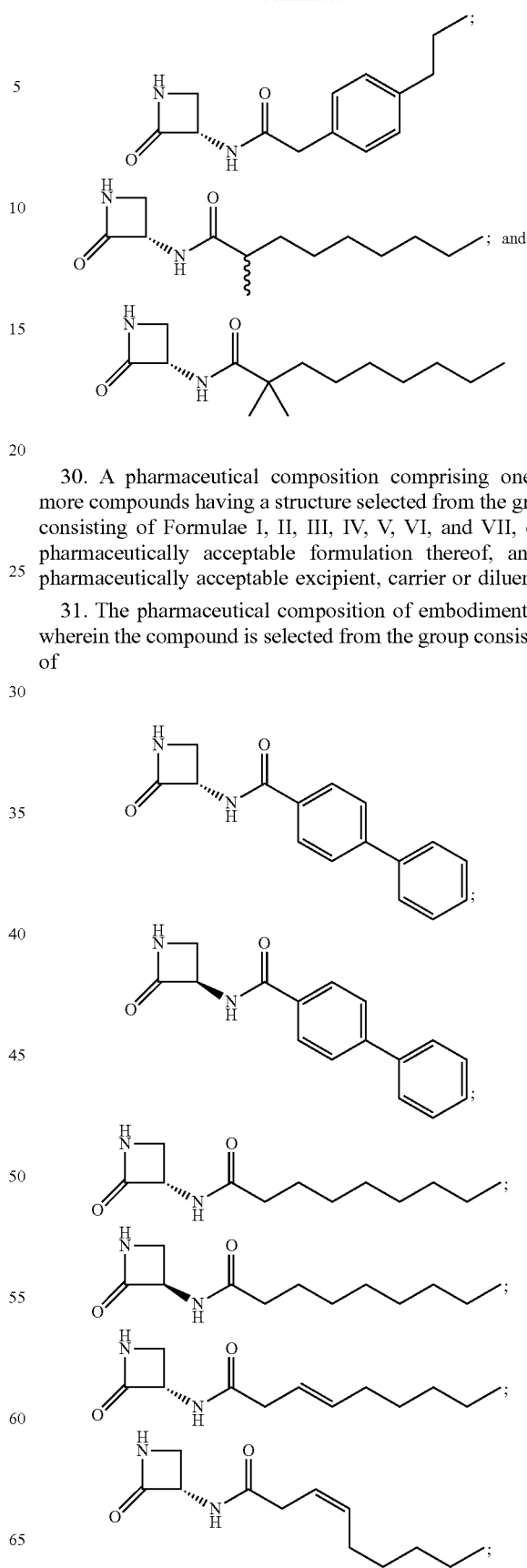

30. A pharmaceutical composition comprising one or more compounds having a structure selected from the group consisting of Formulae I, II, III, IV, V, VI, and VII, or a pharmaceutically acceptable formulation thereof, and a pharmaceutically acceptable excipient, carrier or diluent.

31. The pharmaceutical composition of embodiment 30, wherein the compound is selected from the group consisting of

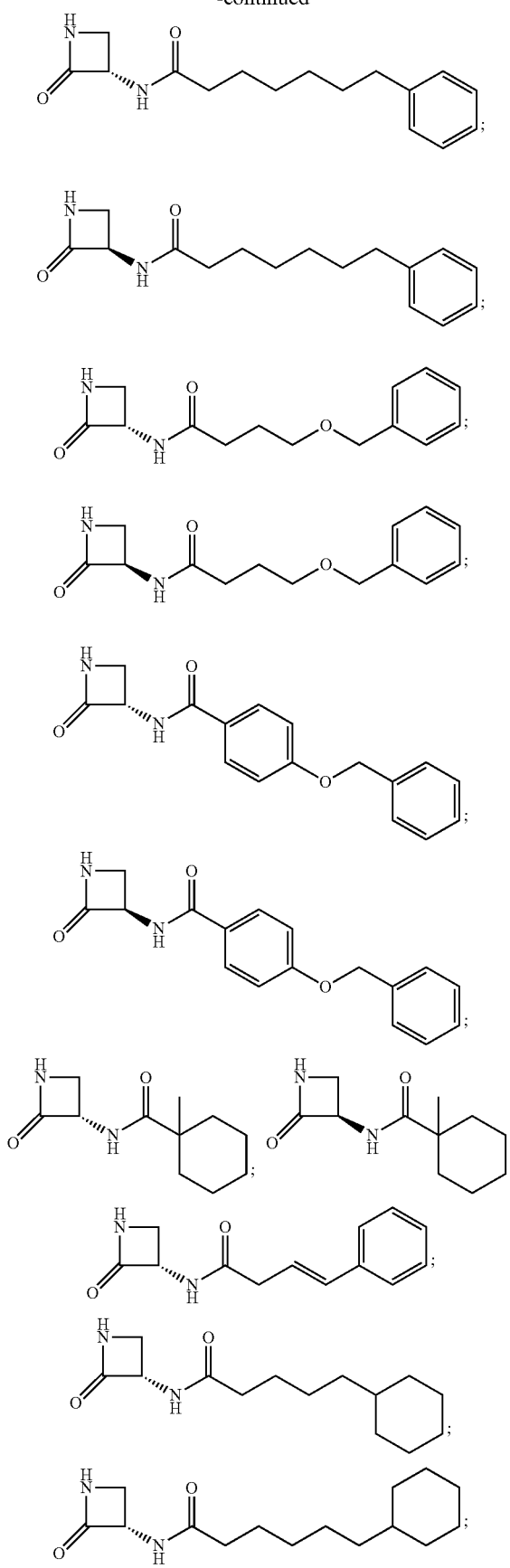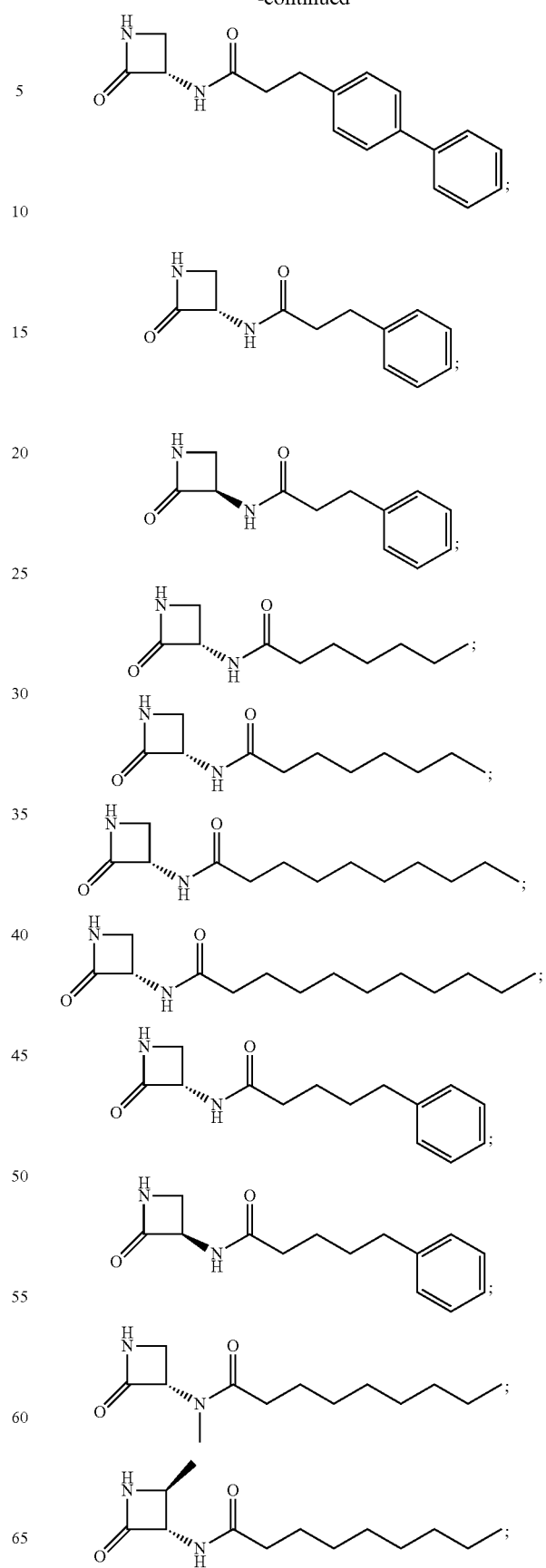

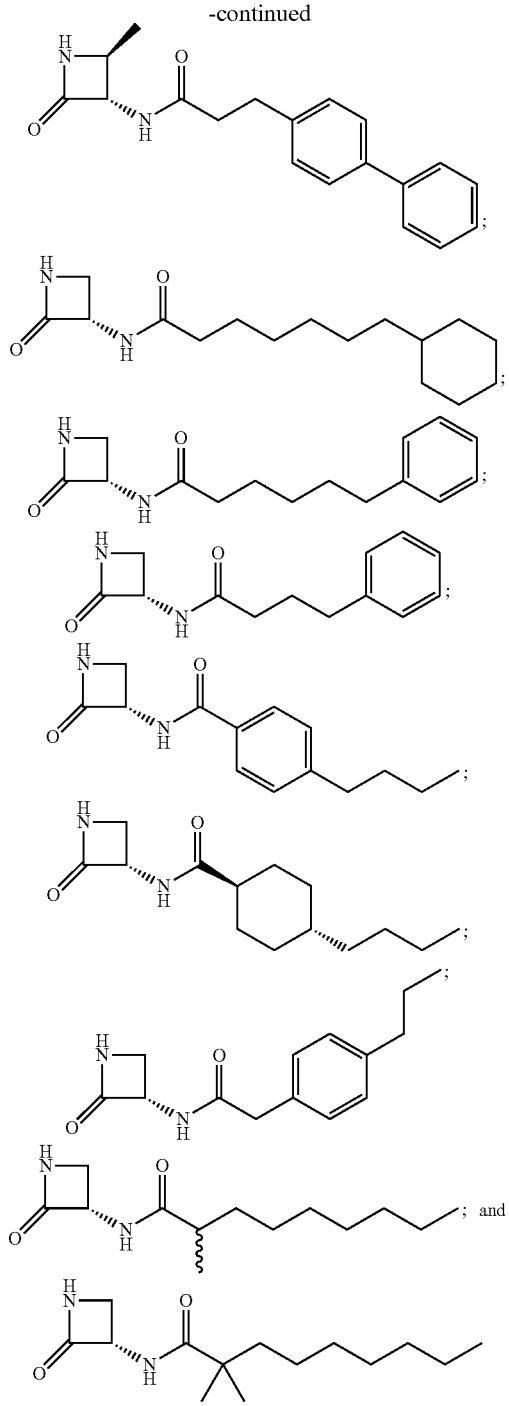

32. A method of treating a mammal suffering from an inflammatory condition comprising administering to the mammal a therapeutically effective amount of a compound having the structure selected from the group consisting of Formula I, II, III, IV, V, VI, and VII.

33. The method of embodiment 32 wherein the inflammatory condition is osteoarthritis, rheumatoid arthritis, asthma, chronic obstructive pulmonary disease (COPD), adult respiratory disease, chronic bronchitis, inflammatory bowel disease, ulcerative colitis, Crohn's disease, ileocolitis, ileitis, gastroduodenal Crohn's disease, jejunoileitis, lupus, graft vs. host reaction (i.e., graft vs. host disease), acute and chronic allograft rejection, acute respiratory distress syndrome, multiple sclerosis, restinosis, cystic fibrosis, crystal induced arthritis, ocular inflammation (including dry eye), corneal damage, hyperoxia-induced inflammation, myofascitis, polymyositis, carpal tunnel, sprains, contusions, dental pain, vasculitis, or periodontitis.

34. The method of one of embodiments 32 to 33, wherein the inflammatory condition is contact dermatitis, atopic dermatitis, seborrhoic dermatitis, eczema, urticaria, rosacea, acne, psoriasis, lichen, psoriatic arthritis acne, skin burns deriving from various origins, surgical skin incisions, or delayed skin healing induced by diabetes, immunosuppression or other causes.

35. A method of treating a mammal suffering from a painful or pruritogenic pathological state not attributable to inflammation comprising administering to the mammal a compound having the structure selected from the group consisting of Formula I, II, III, IV, V, VI, and VII.

36. The method of embodiment 35, wherein the pathological state is post herpetic neuralgia, trigeminal neuralgia, causalgia, diabetic neuropathy, neuropathic low back pain, peripheral or polyneuropathic pain, toxic neuropathy, chronic neuropathy caused by chemotherapeutic and antiviral agents, or pruritus induced by uremia, malignancies of various origin, polycythemia, jaundice or cholestasis, iron deficiency, athlete's foot, xerosis, wound healing, thyroid illness, hyperparathyroidism, or menopause.

37. A method of treating a mammal suffering from a neurodegenerative disorder, comprising administering to the mammal a therapeutic amount of a compound having the structure selected from the group consisting of Formula I, II, III, IV, V, VI, and VII.

38. The method of embodiment 37, wherein the neurodegenerative disorder is Alzheimer's dementia, Parkinson's disease, Huntington's disease, Amytrophic Lateral Sclerosis, or macular degeneration.

39. A method of inhibiting NAAA comprising contacting the NAAA in vitro with an effective amount of a compound having a structure selected from the group consisting of Formula I, II, III, IV, V, VI, and VII.

40. The method of one of embodiments 32 to 39 wherein the compound is selected from the group consisting of

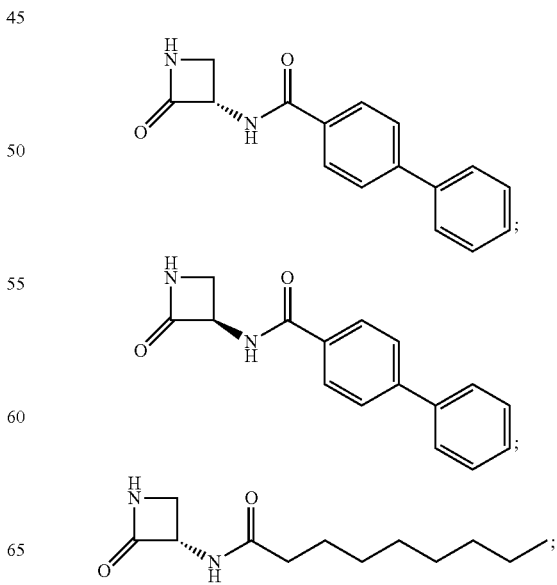

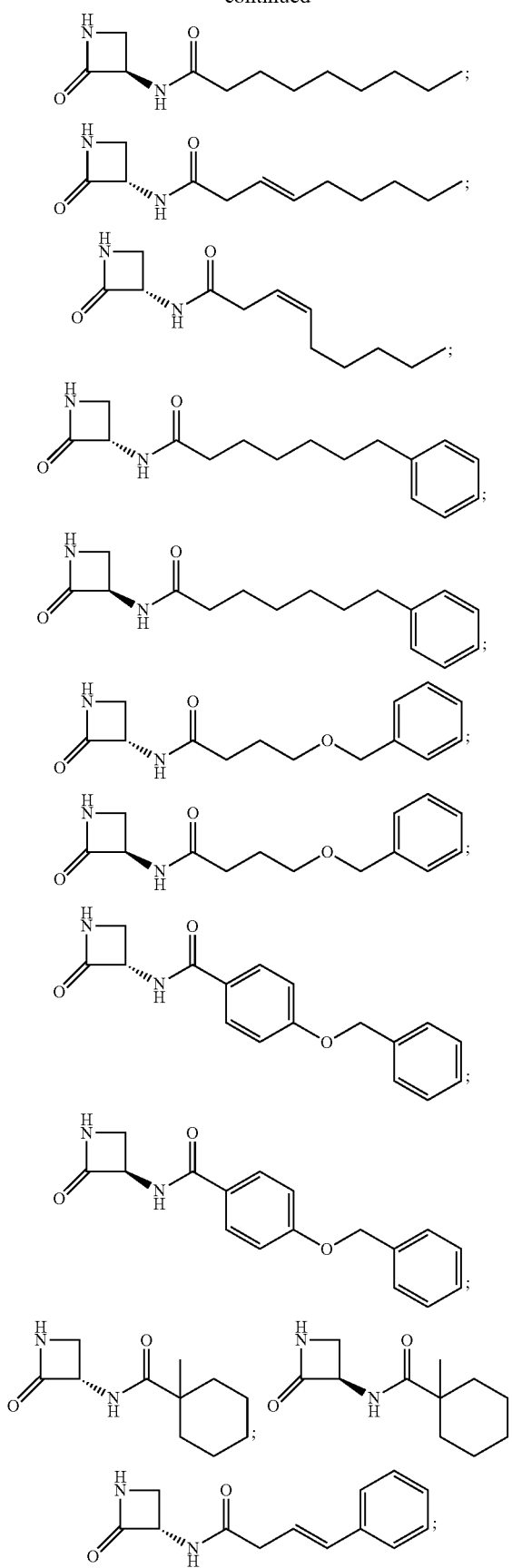
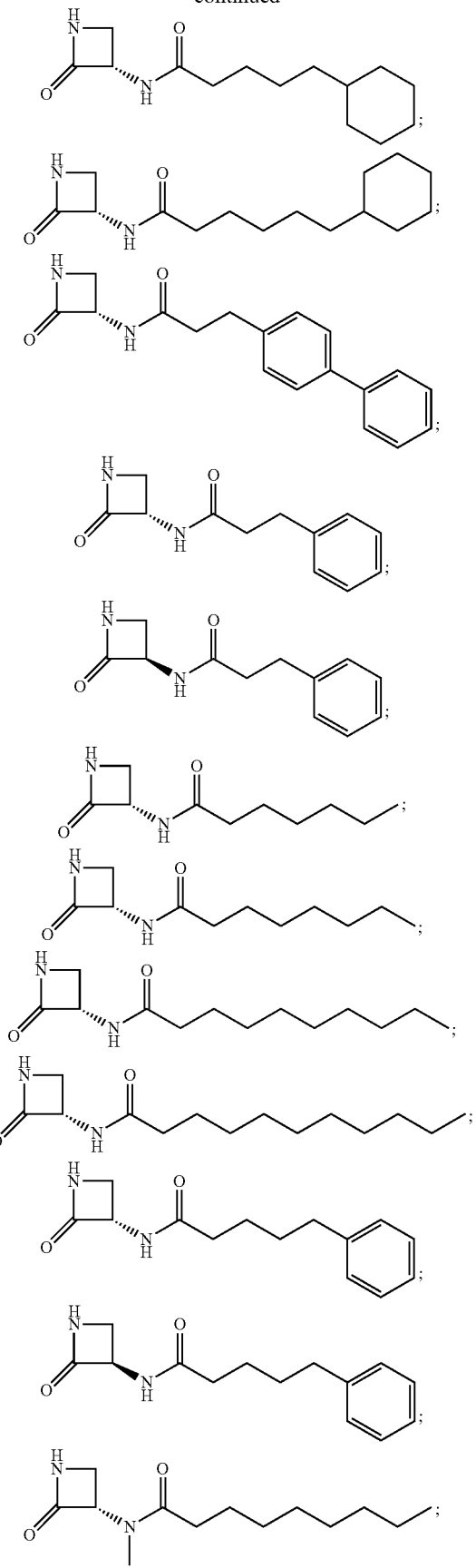

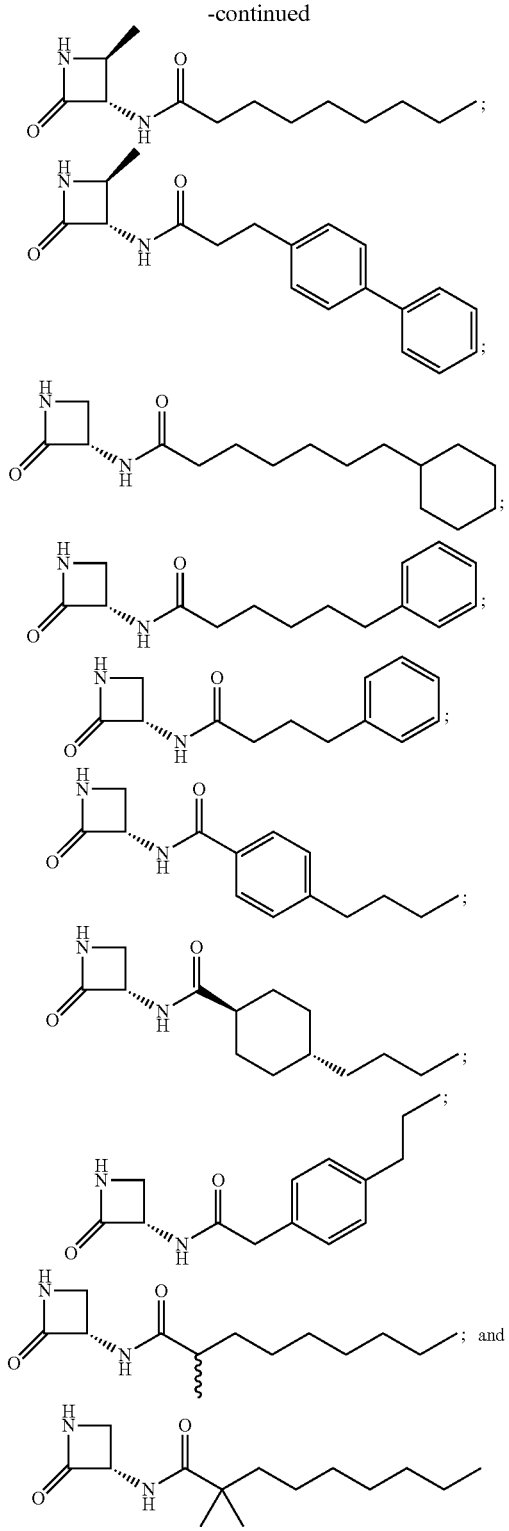

EXAMPLES

Methods for Testing Compounds on NAAA

UPLC/MS r-NAAA Assay

Lysosomal NAAA protein preparation was obtained by homogenizing male Sprague-Dawley rat lungs (Charles River) in 20 mM Tris-HCl buffer pH 7.4 containing 0.32M sucrose. Samples were centrifuged at 800×g for 15 min at 4° C. Supernatants were centrifuged at 12,000×g for 30 min at 4° C. Pellets were then resuspended in PBS pH 7.4 and subjected to a freeze/thaw cycle at −80° C. The suspension was finally centrifuged at 105,000 g for 1 h at 4° C. The supernatant was used in enzymatic assays.

NAAA preparations were pre-incubated with various concentrations of test compounds or vehicle control in 100 mM $NaH_2PO_4$/Citrate buffer, 1% Triton-X, 3 mM DTT (pH 4.5) for 30 min at 37° C. Samples were incubated with heptadecenoylethanolamide (50 µM, Avanti Polar Lipids) at 37° C. for 30 min. The reaction was terminated by addition of cold methanol containing heptadecanoic acid (NuCheck Prep) as internal standard. Samples were analyzed by UPLC/MS (Acquity, Waters). Heptadecenoic and heptadecanoic acids were eluted on an Acquity UPLC BEH C18 column (50 mm length, 2.1 mm i.d., 1.7 µm pore size, Waters) isocratically at 0.5 mL/min for 1.5 min with a solvent mixture of 95% methanol and 5% $H_2O$, both containing 0.25% Acetic Acid and 5.0 mM ammonium acetate. The column temperature was 40° C. Electrospray ionization was in the negative mode, capillary voltage was 0.5 kV, cone voltage was 25 kV, desolvation temperature was 500° C. $N_2$ was used as drying gas at a flow rate of 1000 L/hour and a temperature of 500° C. The $[M-H]^-$ ion was monitored in the selected-ion monitoring mode (m/z values: heptadecenoic acid 267.37, heptadecanoic acid 269.37). Calibration curves were generated using commercial heptadecenoic acid (NuCheck Prep) Inhibition of NAAA activity was calculated as reduction of heptadecanoic acid in the samples compared to vehicle controls. $IC_{50}$ values were calculated by non-linear regression analysis of log [concentration]/inhibition curves using GraphPad Prism 5 (GraphPad Software Inc., CA—USA) applying a standard slope curve fitting.

Fluorogenic h-NAAA Assay

Hek293 cells stably transfected with the human NAAA coding sequence cloned from a human spleen cDNA library were used as enzyme source. Recombinant HEK-hNAAA pellets were resuspended in homogenizing buffer, and sonicated. Samples were centrifuged at 800×g for 15 min at 4° C. and the supernatants were ultracentrifuged at 12,000×g for 30 min at 4° C. The pellets were resuspended in PBS pH 7.4 on ice and subjected to a freeze/thaw cycle at −80° C. (two freeze/thaw cycles at −80° C. for Examples 34-37). The suspension was finally centrifuged at 105,000×g for 1 h at 4° C. Protein concentration was measured and samples stored at −80° C. until use.

The assay was run in Optiplate 96-wells black plates, in a total reaction volume of 200 µL. NAAA protein preparation (4.0 µg for Examples except 34-37, which were 20.0 µg) was pre-incubated for 10 min with various concentrations of test compounds or vehicle control (5% DMSO) in 100 mM citrate/phosphate buffer (pH 4.5) containing 3.0 mM DTT, 0.1% Triton X-100, 0.05% BSA, 150 mM NaCl. N-(4-methyl-2-oxo-chromen-7-yl)-hexadecanamide was used as a substrate (5.0 µM) and the reaction carried over for 30 min at 37° C. The samples were then read in a Perkin Elmer Envision plate reader using an excitation wavelength of 360 nm and emission 460 nm. IC50 values were calculated by non-linear regression analysis of log [concentration]/inhibition curves using GraphPad Prism 5 (GraphPad Software Inc., CA—USA) applying a standard slope curve fitting.

The selectivity of selected compounds versus Acid Ceramidase (AC) was determined.

Rat AC (r-AC) Assay

Rat AC (r-AC) was cloned from a brain cDNA library using primers based on the sequence obtained from the National Center for Biotechnology Information (NCBI) database: 5'rAC (5'-GACCATGCTGGGCCGTAGT-3') (SEQ ID NO:1) and 3'rAC (5'-CCAGCCTATA-CAAGGGTCT-3') (SEQ ID NO:2). The PCR (High Fidelity PCR Master, Roche) product was subcloned into a pEF6-V5/His vector (Invitrogen) to construct a mammalian expression vector encoding V5/His-tagged rat AC. HEK293 cells were transfected with pEF6-rAC-V5/His using Super-Fect reagent (Qiagen) and screened with G418 (0.3 mg/mL). Cells were suspended in 20 mM Tris HCl (pH 7.5) containing 0.32M sucrose, sonicated and centrifuged at 800×g for 15 min at 4° C. The supernatants were centrifuged again at 12,000×g for 30 min at 4° C. The pellets were suspended in phosphate-buffered saline (PBS) and subjected to 2 freeze-thaw cycles at −80° C. The suspensions were centrifuged at 105,000×g for 1 hour at 4° C. The supernatants containing recombinant AC were kept at −80° C. until use. Protein concentration was measured using the bicinchoninic acid (BCA) assay (Pierce). Recombinant rat AC (50 µg) was preincubated with inhibitors (final DMSO concentration 1%) in assay buffer (100 mM sodium phosphate, 0.1% Nonidet P-40, 150 mM NaCl, 3 mM DTT, 100 mM sodium citrate, pH 4.5) for 30 min at 37° C. Reactions were started by the addition of 100 µM N-lauroyl ceramide (Nu-Chek Prep, Elysian, Minn.) and carried on for 30 min at 37° C. Reactions were stopped by addition of a mixture of chloroform/methanol (2:1, vol/vol) containing 1 nmol of heptadecanoic acid (HDA; NuChek Prep). The organic phases were collected, dried under N2, and analyzed by LC-MS in the negative-ion mode using heptadecenoic acid (HDA) as internal standard (m/z=199 for lauric acid, m/z=269 for HDA). HDA was eluted on an XDB Eclipse C18 column isocratically at 2.2 mL/min for 1 min with a solvent mixture of 95% methanol and 5% water, both containing 0.25% acetic acid and 5 mM ammonium acetate. The column temperature was 50° C. Electrospray ionization (ESI) was in the negative mode, capillary voltage as 4 kV, and fragmentor voltage was 100 V. N2 was used as drying gas at a flow rate of 13 L/min and a temperature of 350° C. Nebulizer pressure was set at 60 psi. We monitored [M+H]− in the selected-ion monitoring (SIM) mode using HDA as internal standard. Calibration curves were generated using commercial lauric acid (Nu-Chek Prep; m/z=199).

The $IC_{50}$ values of representative compounds of the invention on NAAA and AC are reported in Table 1.

The compounds of the present invention inhibited NAAA activity with $IC_{50}$ lower than 100 µM. The $IC_{50}$s of representative compounds of the invention are reported in Table 1.

TABLE 1

$IC_{50}$ values of representative compounds of the invention

| Example | r-NAAA UPLC/MS assay $IC_{50}$ (µM) | h-NAAA Fluorogenic assay $IC_{50}$ (µM) | r-AC UPLC/MS assay $IC_{50}$ (µM) |
|---|---|---|---|
| 1 | 15% inhib.@ 3 µM | | |
| 2 | 10% inhib.@ 3 µM | | |
| 3 | 0.24 | 0.108 | 25% inhib.@ 1 µM |
| 4 | | 40 | |
| 5 | 2.3 | 1.34 | |
| 6 | 0.68 | 1.94 | |
| 7 | 2.1 | 0.334 | 25% inhib.@ 1 µM |
| 8 | 30% inhib.@ 3 µM | | |
| 9 | n.a. | | |
| 10 | 10% inhib.@ 30 µM | | |
| 11 | 10% inhib.@ 30 µM | | |
| 12 | 10% inhib.@ 3 µM | | |
| 13 | n.a. | | |
| 14 | n.a. | | |
| 15 | 20% inhib.@ 30 µM | | |
| 16 | 1.0 | | |
| 17 | 0.13 | 0.275 | |
| 18 | | n.a. | |
| 19 | | 15% inhib.@ 50 µM | |
| 20 | | n.a. | |
| 21 | | 7.83 | |
| 22 | | 0.93 | |
| 23 | | 0.086 | 70% inhib.@ 1 µM |
| 24 | | 0.043 | |
| 25 | | 33.9 | |
| 26 | | n.a. | |
| 27 | 40% inhib.@ 3 µM | 20% inhib. 2.5 µM | |
| 28 | | 0.38 | |
| 29 | | 60% inhib.@ 50 µM | |
| 30 | | 0.21 | 45% inhib.@ 1 µM |
| 31 | | 13.4 | |
| 32 | | 110 | |
| 33 | | 16% inhib.@ 2.5 µM | |
| 34 | | 4.023 | |
| 35 | | 15.65 | |
| 36 | | 0.22 | |
| 37 | | 0.758 | | n.a. = <10% inhib.@100 µM

Methods for Screening Compounds for a Therapeutic Activity

A variety of animal models can be used to test the compounds of the present invention for their therapeutic effectiveness in treating inflammatory and pain states. With the aim to better illustrate the present invention, without limiting it, a method for testing the compounds of the present invention for therapeutic effectiveness is reported hereunder.

Pharmacological Testing

Carrageenan-Induced Inflammation

Paw edema was induced by injecting λ-carrageenan (1% weight/vol in sterile $H_2O$, 50 µL) into the left hind paw of lightly restrained mice (Sasso et al., *Pharmacol. Res.* 2012; 65: 553-632). All experiments were performed in a quiet room, and experimenters were blinded to the treatment protocol at the time of the test. Edema was measured with a plethysmometer (Ugo Basile, Comerio, Italy). Heat hyperalgesia was assessed measuring the latency to withdraw the hind paw from a focused beam of radiant heat (thermal intensity: infrared 3.0) applied to the plantar surface in a plantar test apparatus (Ugo Basile). The cutoff time was set at 30 s. Fresh drug solutions were prepared daily and given by intraperitoneal injection (in 80% sterile saline solution/10% PEG-400/10% Tween 80, 200 µL per animal), at the same time of carrageenan injection. Intraplantar administration of carrageenan in mice resulted in the development of paw edema and heat hyperalgesia. Both responses were markedly attenuated, in a dose- and time-dependent manner, by oral administration (p.o.) of compound 5 (3-30 mg/kg) as shown in FIG. 1.

Acute Inflammation Models

Carrageenan-Induced Lung Inflammation

Saline or saline containing 2% carrageenan (0.1 mL) was injected into the pleural cavity of mice, using a 1 mm needle at the level of the 6$^{th}$ intercostal space. 4 hours after the injection of carrageenan, mice were killed by inhalation of $CO_2$. The chest was carefully opened and the pleural cavity was rinsed with 1 mL of saline solution containing heparin (5 U/mL). The exudate and washing solution were removed by aspiration and the total volume of the fluid was measured. Any exudate that was contaminated with blood was discarded. The amount of exudate was calculated by subtracting the volume of washing fluid injected from the total volume recovered.

LPS-Induced Inflammation

Mice were anesthetized with ketamine and xylazine (100 and 10 mg/kg, respectively), and were submitted to intranasal instillation of LPS (1 µg/µL) or vehicle (saline 0.9%); the volume used was 1 µL/g body weight. In order to avoid drawing, the weight of each animal was divided by three; therefore each mouse received the respective volume of LPS or vehicle. Ex: animal 1 (24 g) received 3 times an intranasal instillation of 8 µL of LPS solution or vehicle.

The bronchoalveolar lavage and lung samples were collected 6 h or 24 h after the induction of inflammation.

General Purification and Analytical Methods

UPLC/MS analyses were run on a Waters ACQUITY UPLC/MS instrument consisting of a SQD Single Quadropole Mass Spectrometer equipped with an electrospray ionization interface and a photodiode array detector. The analyses were performed on an ACQUITY UPLC BEH C18 column (50×2.1 mmID, particle size 1.7 µm) with a VanGuard BEH C18 pre-column (5×2.1 mmID, particle size 1.7 µm). The mobile phases were 10 mM NH4OAc at pH 5 adjusted with AcOH (A) and 10 mM NH$_4$OAc in MeCN—H$_2$O (95:5) at pH 5 (B). Electrospray ionization in positive and negative mode was used in the mass scan range 100-500 Da.

Purifications by preparative HPLC/MS were run on a Waters Autopurification system consisting of a 3100 Single Quadropole Mass Spectrometer equipped with an electrospray ionization interface and a 2998 Photodiode Array Detector. The HPLC system included a 2747 Sample Manager, 2545 Binary Gradient Module, System Fluidic Organizer and 515 HPLC Pump. The purifications were performed on a XBridge™ Prep C$_{18}$ OBD column (100×19 mmID, particle size 5 µm) with a XBridge™ Prep C$_{18}$ (10×19 mmID, particle size 5 µm) Guard Cartridge. The mobile phases were either 1) H$_2$O and MeCN (B) or 2) 10 mM NH$_4$OAc at pH 5 adjusted with AcOH (A) and 10 mM NH$_4$OAc in MeCN—H$_2$O (95:5) at pH 5 (B). Electrospray ionization in positive and negative mode was used in the mass scan range 100-500 Da.

Automated column chromatography purification was done using a Teledyne ISCO apparatus (CombiFlash® Rf) with normal phase pre-packed silica gel columns of different sizes (from 4 g until 120 g). Typical silica gel column chromatography is intended as a purification performed using normal glass columns filled with Merck silica gel 60 (230-400 mesh) as stationary phase. Mixtures of solvents used as eluents are reported below.

Hydrogenation reactions were performed using H-Cube® continuous flow hydrogenation equipment (SS-reaction line version), employing disposable cartridges (CatCart®), preloaded with the required heterogeneous catalyst.

Microwave heating was performed using Explorer®-48 positions instrument (CEM).

NMR experiments were run on a Bruker Avance III 400 system (400.13 MHz for $^1$H, and 100.62 MHz for $^{13}$C), equipped with a BBI inverse probe and Z-gradients. Unless indicated, spectra were acquired at 300 K, using deuterated dimethylsulfoxyde (DMSO-d$_6$) and deuterated chloroform (CDCl$_3$) as solvents.

TABLE 2

Examples of compounds of the invention

| Example | Structure | Formula | Name |
|---|---|---|---|
| 1 | 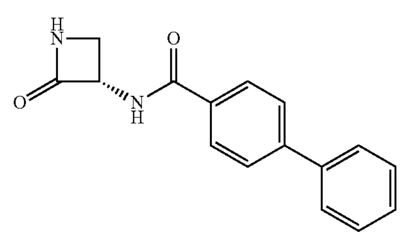 [SMILES: O=C(N[C@H]1CNC1=O)c1ccc(-c2ccccc2)cc1] | $C_{16}H_{14}N_2O_2$ | 4-Phenyl-N-[(3S)-2-oxoazetidin-3-yl]-benzamide |
| 2 | 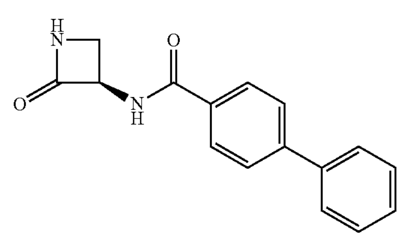 [SMILES: O=C(N[C@@H]1CNC1=O)c1ccc(-c2ccccc2)cc1] | $C_{16}H_{14}N_2O_2$ | 4-Phenyl-N-[(3R)-2-oxoazetidin-3-yl]-benzamide |
| 3 | 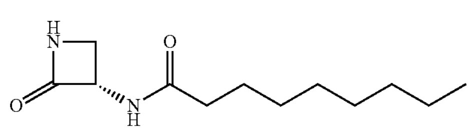 [SMILES: CCCCCCCCC(=O)N[C@H]1CNC1=O] | $C_{12}H_{22}N_2O_2$ | N-[(3S)-2-Oxoazetidin-3-yl]-nonanamide |

TABLE 2-continued

Examples of compounds of the invention

| Example | Structure | Formula | Name |
| --- | --- | --- | --- |
| 4 | 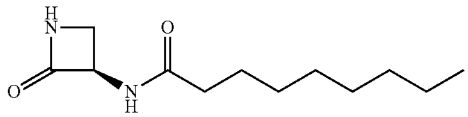 [SMILES: CCCCCCCCC(=O)N[C@@H]1CNC1=O] | $C_{12}H_{22}N_2O_2$ | N-[(3R)-2-Oxoazetidin-3-yl]-nonanamide |
| 5 | 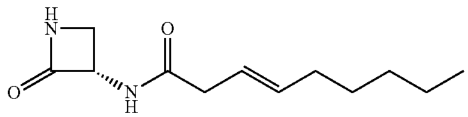 [SMILES: CCCCC/C=C/CC(=O)N[C@H]1CNC1=O] | $C_{12}H_{20}N_2O_2$ | (E)-N-[(3S)-2-Oxoazetidin-3-yl]-non-3-enamide |
| 6 | 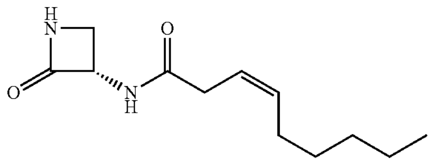 [SMILES: CCCCC/C=C\CC(=O)N[C@H]1CNC1=O] | $C_{12}H_{20}N_2O_2$ | (Z)-N-[(3S)-2-Oxoazetidin-3-yl]-non-3-enamide |
| 7 | 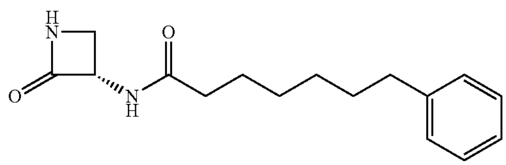 [SMILES: O=C(CCCCCCc1ccccc1)N[C@H]1CNC1=O] | $C_{16}H_{22}N_2O_2$ | 7-Phenyl-N-[(3S)-2-oxoazetidin-3-yl]-heptanamide |
| 8 | 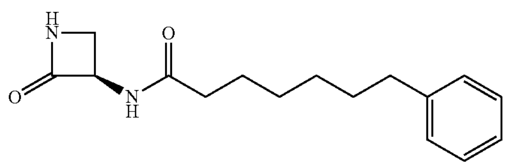 [SMILES: O=C(CCCCCCc1ccccc1)N[C@@H]1CNC1=O] | $C_{16}H_{22}N_2O_2$ | 7-Phenyl-N-[(3R)-2-oxoazetidin-3-yl]-heptanamide |
| 9 | 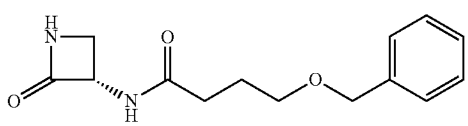 [SMILES: O=C(CCCOCc1ccccc1)N[C@H]1CNC1=O] | $C_{14}H_{18}N_2O_3$ | 4-Benzyloxy-N-[(3S)-2-oxoazetidin-3-yl]-butanamide |
| 10 | 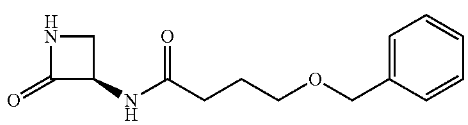 [SMILES: O=C(CCCOCc1ccccc1)N[C@@H]1CNC1=O] | $C_{14}H_{18}N_2O_3$ | 4-Benzyloxy-N-[(3R)-2-oxoazetidin-3-yl]-butanamide |
| 11 | 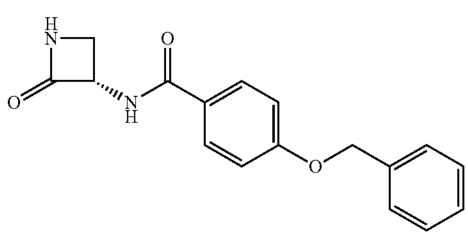 [SMILES: O=C(N[C@H]1CNC1=O)c1ccc(OCc2ccccc2)cc1] | $C_{17}H_{16}N_2O_3$ | 4-Benzyloxy-N-[(3S)-2-oxoazetidin-3-yl]-benzamide |
| 12 | 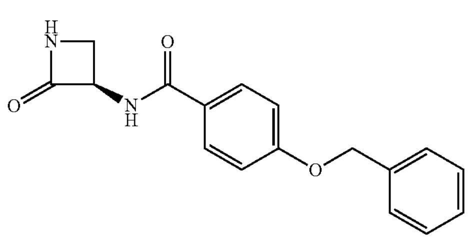 [SMILES: O=C(N[C@@H]1CNC1=O)c1ccc(OCc2ccccc2)cc1] | $C_{17}H_{16}N_2O_3$ | 4-Benzyloxy-N-[(3R)-2-oxoazetidin-3-yl]-benzamide |

TABLE 2-continued

Examples of compounds of the invention

| Example | Structure | Formula | Name |
|---|---|---|---|
| 13 | 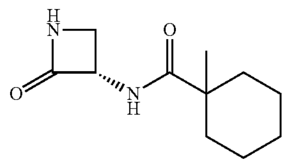 | $C_{11}H_{18}N_2O_2$ | 1-Methyl-N-[(3S)-2-oxoazetidin-3-yl]-cyclohexanecarboxamide |
| 14 | 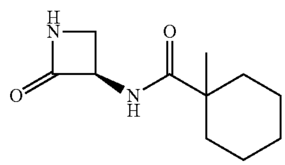 | $C_{11}H_{18}N_2O_2$ | 1-Methyl-N-[(3R)-2-oxoazetidin-3-yl]-cyclohexanecarboxamide |
| 15 | 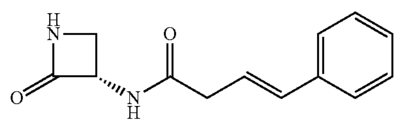 [SMILES: O=C(C/C=C/c1ccccc1)N[C@H]1CNC1=O] | $C_{13}H_{14}N_2O_2$ | (E)-N-[(3S)-2-Oxoazetidin-3-yl]-4-phenyl-but-3-enamide |
| 16 | 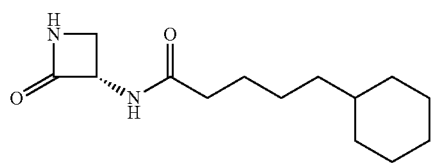 [SMILES: O=C(CCCCC1CCCCC1)N[C@H]1CNC1=O] | $C_{14}H_{24}N_2O_2$ | 5-Cyclohexyl-N-[(3S)-2-oxoazetidin-3-yl]-pentanamide |
| 17 | 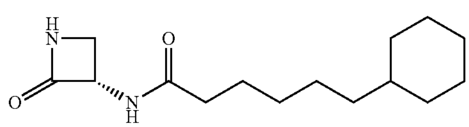 [SMILES: O=C(CCCCCC1CCCCC1)N[C@H]1CNC1=O] | $C_{15}H_{26}N_2O_2$ | 6-Cyclohexyl-N-[(3S)-2-oxoazetidin-3-yl]-hexanamide |
| 18 | 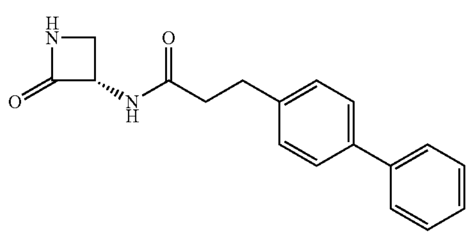 [SMILES: O=C(CCc1ccc(-c2ccccc2)cc1)N[C@H]1CNC1=O] | $C_{18}H_{18}N_2O_2$ | 3-(4-Phenylphenyl)-N-[(3S)-2-oxoazetidin-3-yl]-propanamide |
| 19 | 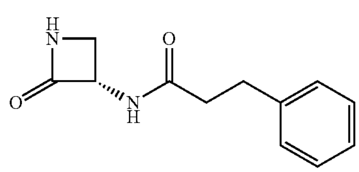 [SMILES: O=C(CCc1ccccc1)N[C@H]1CNC1=O] | $C_{12}H_{14}N_2O_2$ | 3-Phenyl-N-[(3S)-2-oxoazetidin-3-yl]-propanamide |
| 20 | 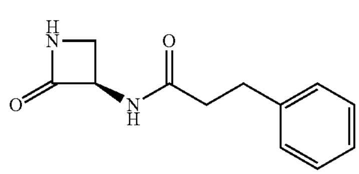 [SMILES: O=C(CCc1ccccc1)N[C@@H]1CNC1=O] | $C_{12}H_{14}N_2O_2$ | 3-Phenyl-N-[(3R)-2-oxoazetidin-3-yl]-propanamide |
| 21 | 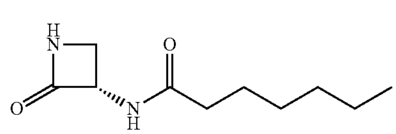 | $C_{10}H_{18}N_2O_2$ | N-[(3S)-2-Oxoazetidin-3-yl]-heptanamide |

TABLE 2-continued

Examples of compounds of the invention

| Example | Structure | Formula | Name |
|---|---|---|---|
| 22 | 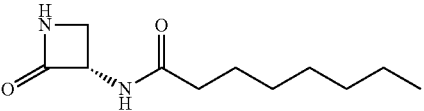 | $C_{11}H_{20}N_2O_2$ | N-[(3S)-2-Oxoazetidin-3-yl]-octanamide |
| 23 | 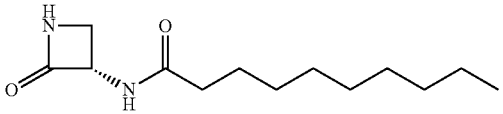 [SMILES: CCCCCCCCCC(=O)N[C@H]1CNC1=O] | $C_{13}H_{24}N_2O_2$ | N-[(3S)-2-Oxoazetidin-3-yl]-decanamide |
| 24 | 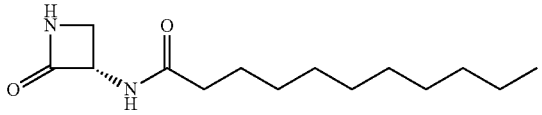 [SMILES: CCCCCCCCCCC(=O)N[C@H]1CNC1=O] | $C_{14}H_{16}N_2O_2$ | N-[(3S)-2-Oxoazetidin-3-yl]-undecanamide |
| 25 | 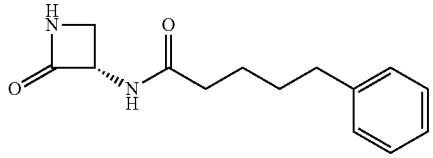 [SMILES: O=C(CCCCc1ccccc1)N[C@H]1CNC1=O] | $C_{14}H_{18}N_2O_2$ | 5-Phenyl-N-[(3S)-2-oxoazetidin-3-yl]-pentanamide |
| 26 | 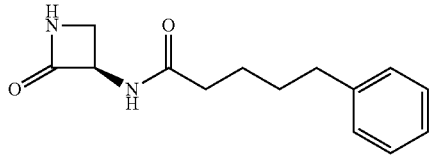 [SMILES: O=C(CCCCc1ccccc1)N[C@@H]1CNC1=O] | $C_{14}H_{18}N_2O_2$ | 5-Phenyl-N-[(3R)-2-oxoazetidin-3-yl]-pentanamide |
| 27 | 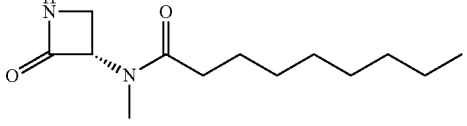 | $C_{13}H_{24}N_2O_2$ | N-Methyl-N-[(3S)-2-oxoazetidin-3-yl]-nonanamide |
| 28 | 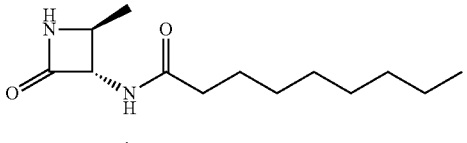 | $C_{13}H_{24}N_2O_2$ | N-[(2S,3S)-2-methyl-4-oxo-azetidin-3-yl]-nananamide |
| 29 | 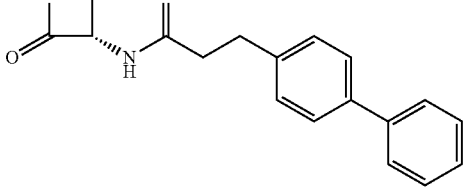 | $C_{19}H_{20}N_2O_2$ | 3-(4-phenylphenyl)-N-[(2S,3S)-2-methyl-4-oxo-azetidin-3-yl]-propanamide |
| 30 | 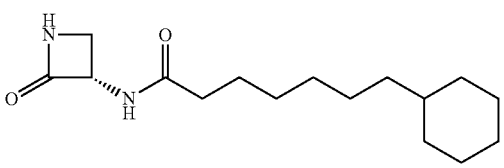 [SMILES: O=C(CCCCCCC1CCCCC1)N[C@H]1CNC1=O] | $C_{16}H_{28}N_2O_2$ | 7-cyclohexyl-N-[(3S)-2-oxoazetidin-3-yl]-heptanamide |
| 31 | 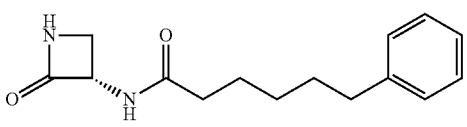 [SMILES: O=C(CCCCCc1ccccc1)N[C@H]1CNC1=O] | $C_{15}H_{20}N_2O_2$ | 6-phenyl-N-[(3S)-2-oxoazetidin-3-yl]-hexanamide |

TABLE 2-continued

Examples of compounds of the invention

| Example | Structure | Formula | Name |
|---|---|---|---|
| 32 | 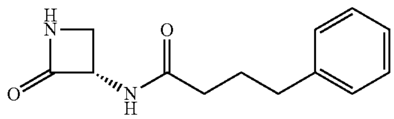 [SMILES: O=C(CCCc1ccccc1)N[C@H]1CNC1=O] | $C_{13}H_{16}N_2O_2$ | 4-phenyl-N-[(3S)-2-oxoazetidin-3-yl]-butanamide |
| 33 | 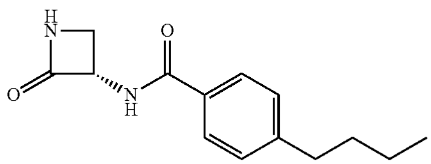 [SMILES: CCCCc1ccc(C(=O)N[C@H]2CNC2=O)cc1] | $C_{14}H_{18}N_2O_2$ | 4-butyl-N-[(3S)-2-oxoazetidin-3-yl]-benzamide |
| 34 | 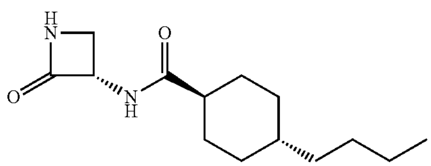 [SMILES: CCCC[C@H]1CC[C@H](C(=O)N[C@H]2CNC2=O)CC1] | $C_{14}H_{24}N_2O_2$ | (1r,4R)-4-butyl-N-((S)-2-oxoazetidin-3-yl)cyclohexanecarboxamide |
| 35 | 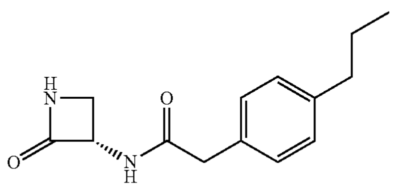 [SMILES: CCCc1ccc(CC(=O)N[C@H]2CNC2=O)cc1] | $C_{14}H_{18}N_2O_2$ | N-[(3S)-2-oxoazetidin-3-yl]-2-(4-propylphenyl)acetamide |
| 36 | 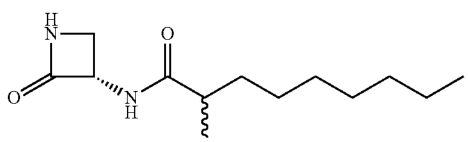 [SMILES: CCCCCCCC(C)C(=O)N[C@H]1CNC1=O] | $C_{13}H_{24}N_2O_2$ | (2R)-2-methyl-N-[(3S)-2-oxoazetidin-3-yl]nananamide and (2S)-2-methyl-N-[(3S)-2-oxoazetidin-3-yl]nonanamide |
| 37 | 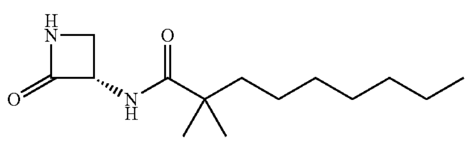 [SMILES: CCCCCCCC(C)(C)C(=O)N[C@H]1CNC1=O] | $C_{14}H_{16}N_2O_2$ | 2,2-dimethyl-N-[(3S)-2-oxoazetidin-3-yl]nonanamide |

The compounds reported in Table 2 were synthesized as described below.

Solvents and reagents were obtained from commercial suppliers and were used without further purification. For simplicity, solvents and reagents were indicated as follows: Tetrahydrofuran (THF), diethyl ether ($Et_2O$), ethyl acetate (EtOAc), dichloromethane ($CH_2Cl_2$), isopropanol (iPrOH), dimethylsulfoxyde (DMSO) hydrochloric acid (HCl), cyclohexane (Cy), acetic acid ($CH_3COOH$), trifluoroacetic acid (TFA), N,N-dimethylformamide (DMF), triethylamine ($Et_3N$), methanol (MeOH), acetonitrile ($CH_3CN$), methyl tert-butyl ether (MTBE), ethanol (EtOH), N,N-Diisopropylethylamine (DIPEA), sodium bicarbonate ($NaHCO_3$), sodium sulfate ($Na_2SO_4$), sodium hydroxide (NaOH), ammonium chloride ($NH_4Cl$), silica gel ($SiO_2$), sodium nitrite ($NaNO_2$), sodium carbonate ($Na_2CO_3$), potassium carbonate ($K_2CO_3$), potassium hydrogen sulfate ($KHSO_4$), 4-(dimethylamino)-pyridine (DMAP), di-2-pyridyl carbonate (2-DPC), carbonyl-diimidazole (CDI), lithium bis-(trimethylsilyl)-amide (LHMDS), n-butyllithium (BuLi), lithium aluminum hydride ($LiAlH_4$), sodium borohydride ($NaBH_4$), benzotriazol-1-yl-oxytripyrrolidinophosphonium hexafluorophosphate (PyBOP), O-benzotriazole-N,N,N',N'-tetramethyl-uronium hexafluorophosphate (HBTU), O-(benzotriazol-1-yl)-N,N,N',N'-tetra methyluronium tetra fluoroborate (TBTU), 1,3-dimethyl-3,4,5,6-tetrahydro-2(1H)-pyrimidinone (DMPU), triphenylphosphine ($PPh_3$), cerium (IV) ammonium nitrate (CAN), sodium hydride (NaH), cesium fluoride (CsF), tert-butyldimethylsilyl chloride (TBDM-SCl), potassium bis-(trimethylsilyl)-amide (KHMDS).

Preparation of [(3S)-2-oxoazetidin-3-yl]-ammonium acetate

The compound was synthesized according to a modified procedure described by Hanessian et al., *Can. J. Chem.* 1985, 63, 3613.

Step 1. Preparation of benzyl-N-[(1S)-1-(hydroxymethyl)-2-[(4-methoxyphenyl)-amino]-2-oxoethyl]-carbamate Under nitrogen atmosphere, to a cooled (0° C.), vigorously stirred solution of commercially available p-anisidine (141.5 g, 1.15 mol) in a 3:1 mixture of dry THF:$CH_2Cl_2$ (2.0

L), commercially available carbobenzyloxy-L-serine (50.0 g, 0.21 mol) and commercially available EDCI (43.9 g, 0.23 mol) were sequentially added. The resulting mixture was stirred at 0° C. for additional 0.5 h and then at r.t. for 16 h. After evaporation of the solvents, trituration with a 1:1 mixture Cy:EtOAc (3×0.4 L) mostly removed the excess of p-anisidine, and the resulting gummy residue was taken up in EtOAc (0.5 L) and washed with a 0.1 M HCl solution (10×0.4 L). The organic layer was dried over $Na_2SO_4$, filtered and concentrated to dryness affording the pure title compound (58.6 g, 82%), as a white solid. $R_t$=1.97 min. MS (ESI) m/z: 345 [M−H]⁺, 367 [M−Na]⁺, 383 [M−K]⁺. ¹H NMR (CDCl₃): δ 8.50-8.27 (bs, 1H), 7.44-7.29 (m, 6H), 6.90-6.81 (d, 2H, J=9.1 Hz), 5.97-5.80 (bs, 1H), 5.17 (s, 2H), 4.37-4.21 (m, 2H), 3.80 (s, 3H), 3.77-3.66 (m, 1H), 2.92-2.75 (bs, 1H).

Step 2. Preparation of benzyl-N-[(3S)-1-(4-methoxyphenyl)-2-oxo-azetidin-3-yl]-carbamate Under nitrogen atmosphere, to a cooled (0° C.), stirred solution of benzyl-N-[(1S)-1-(hydroxymethyl)-2-[(4-methoxyphenyl)-amino]-2-oxo-ethyl]-carbamate (58.6 g, 0.170 mol) in dry DMF (1.6 L), commercially available 1,1'-sulfonyldiimidazole (50.6 g, 0.256 mol) was added. The resulting mixture was stirred at 0° C. for additional 0.5 h and then cooled to −20° C. Under vigorous stirring, commercially available NaH (60% in mineral oil, 10.2 g, 0.256 mol) was added portion wise. The resulting suspension was vigorously stirred at −20° C. for additional 1 h, followed by the addition of MeOH (2.0 mL) and distilled H₂O (1.0 L). A precipitate was observed and filtered off. The solid was washed with additional H₂O (0.2 L) and the collected solid fractions were dried under reduced pressure at 40° C. for 5 h, affording the pure title compound (42.2 g, 76%), as a white solid. $R_t$=2.31 min. MS (ESI) m/z: 327 [M−H]⁺, 349 [M−Na]⁺, 365 [M−K]⁺. ¹H NMR (DMSO-d₆): δ 8.08 (d, 1H, J=8.5 Hz), 7.42-7.28 (m, 5H), 7.30 (d, 2H, J=8.9 Hz), 6.95 (d, 2H, J=8.9 Hz), 5.06 (s, 2H), 4.86 (ddd, 1H, J=8.5, 5.6, 2.6 Hz), 3.90 (t, 1H, J=5.6 Hz), 3.73 (s, 3H), 3.55 (dd, 1H, J=5.6, 2.6 Hz).

Step 3. Preparation of benzyl-N-[(3S)-2-oxoazetidin-3-yl]-carbamate

To a cooled (0° C.), vigorously stirred suspension of benzyl-N-[(3S)-1-(4-methoxyphenyl)-2-oxo-azetidin-3-yl]-carbamate (9.0 g, 0.028 mol) in MeCN (0.5 L) and H₂O (0.4 L), a solution of commercially available CAN (45.4 g, 0.083 mol) in H₂O (100 mL) was added dropwise over 45 min. The resulting mixture was stirred at 0° C. for additional 0.5 h and then NaHCO₃ saturated solution (0.5 L) was cautiously added followed by EtOAc (0.5 L). A colloidal precipitate was observed, filtered off and washed with additional EtOAc (0.2 L). The collected biphasic solution was partitioned and the organic phase was dried over $Na_2SO_4$. Activated charcoal was added to the solution and the organic phase was filtered through a pad of Celite and evaporated. Immediate trituration with Et₂O afforded the pure title compound (4.85 g, 80%), as an off-white solid. $R_t$=1.54 min. MS (ESI) m/z: 221 [M−H]⁺, 243 [M−Na]⁺, 259 [M−K]⁺. ¹H NMR (DMSO-d₆): δ 7.97 (d, 1H, J=8.7 Hz), 7.94 (bs, 1H), 7.42-7.30 (m, 5H), 5.05 (s, 2H), 4.67 (ddd, 1H, J=8.7, 5.4, 2.7 Hz), 3.40 (t, 1H, J=5.4 Hz,), 3.09 (dd, 1H, J=5.4, 2.7 Hz).

Step 4. Preparation of [(3S)-2-oxoazetidin-3-yl]-ammonium acetate

Under nitrogen atmosphere, to a 0.05 M solution of benzyl-N-[(3S)-2-oxoazetidin-3-yl]-carbamate (3.28 g, 0.015 mol) in EtOH (0.3 L), cyclohexadiene (14.1 mL, 0.149 mol) and 10% Pd on activated charcoal (3.27 g) were sequentially added. The resulting suspension was stirred at r.t. for 12 h, then filtered off on a short pad of Celite. The outcoming solution was immediately trapped into a solution of AcOH (0.93 mL, 0.0164 mol) in EtOAc (0.245 L). Evaporation of solvents under reduced pressure, at a temperature below 35° C., gave a solid crude product (1.90 g). Trituration with THF afforded the pure title compound (1.72 g, 79%), as a white solid. ¹H NMR (DMSO-d₆): δ 7.68 (bs, 1H), 3.99 (ddd, 1H, J=5.2, 2.4, 1.2 Hz), 3.32 (t, 1H, J=5.2 Hz), 2.79 (dd, 1H, J=5.2, 2.4 Hz), 1.90 (s, 3H).

Preparation of [(3R)-2-oxoazetidin-3-yl]-ammonium acetate

Step 1. Preparation of benzyl-N-[(1R)-1-(hydroxymethyl)-2-[(4-methoxyphenyl)-amino]-2-oxo-ethyl]-carbamate Under nitrogen atmosphere, to a cooled (0° C.), vigorously stirred solution of commercially available p-anisidine (14.15 g, 0.115 mol) in a 3:1 mixture of dry THF:CH₂Cl₂ (0.2 L), commercially available carbobenzyloxy-D-serine (5.0 g, 0.021 mol) and commercially available EDCI (4.39 g, 0.023 mol) were sequentially added. The resulting mixture was stirred at 0° C. for additional 0.5 h and then at r.t. for 16 h. After evaporation of the solvents, trituration with a 1:1 mixture Cy:EtOAc (3×40 mL) mostly removed the excess of p-anisidine, and the resulting gummy residue was taken up in EtOAc (1.0 L) and washed with a 0.1 M HCl solution (10×0.4 L). The organic layer was dried over $Na_2SO_4$, filtered and concentrated to dryness affording the pure title compound (6.46 g, 90%), as a white solid. $R_t$=1.97 min. MS (ESI) m/z: 345 [M−H]⁺, 367 [M−Na]⁺, 383 [M−K]⁺. ¹H NMR (CDCl₃): δ 8.50-8.27 (bs, 1H), 7.44-7.29 (m, 6H), 6.90-6.81 (d, 2H, J=9.1 Hz), 5.97-5.80 (bs, 1H), 5.17 (s, 2H), 4.37-4.21 (m, 2H), 3.80 (s, 3H), 3.77-3.66 (m, 1H), 2.92-2.75 (bs, 1H).

Step 2. Preparation of benzyl-N-[(3R)-1-(4-methoxyphenyl)-2-oxo-azetidin-3-yl]-carbamate Under nitrogen atmosphere, to a cooled (0° C.), stirred solution of benzyl-N-[(1R)-1-(hydroxymethyl)-2-[(4-methoxyphenyl)-amino]-2-oxo-ethyl]-carbamate (6.46 g, 0.019 mol) in dry DMF (0.17 L), commercially available 1,1'-sulfonyldiimidazole (5.69 g, 0.028 mol) was added. The resulting mixture was stirred at 0° C. for additional 0.5 h and then cooled to −20° C. Under vigorous stirring, commercially available NaH (60% in mineral oil, 1.125 g, 0.028 mol) was added portion wise. The resulting suspension was vigorously stirred at −20° C. for additional 1 h, followed by the addition of MeOH (0.5 mL) and distilled H₂O (0.22 L). A precipitate was observed and filtered off. The solid was washed with additional H₂O (4×0.05 L) and the collected solid fractions were dried under reduced pressure at 40° C. for 16 h, affording the pure title compound (4.616 g, 75%), as a white solid. $R_t$=2.31 min. MS (ESI) m/z: 327 [M−H]⁺, 349 [M−Na]⁺, 365 [M−K]⁺. ¹H NMR (DMSO-d₆): δ 8.08 (d, 1H, J=8.5 Hz), 7.42-7.28 (m, 5H), 7.30 (d, 2H, J=8.9 Hz), 6.95 (d, 2H, J=8.9 Hz), 5.06 (s, 2H), 4.86 (ddd, 1H, J=8.5, 5.6, 2.6 Hz), 3.90 (t, 1H, J=5.6 Hz), 3.73 (s, 3H), 3.55 (dd, 1H, J=5.6, 2.6 Hz).

Step 3. Preparation of benzyl-N-[(3R)-2-oxoazetidin-3-yl]-carbamate

To a cooled (0° C.), vigorously stirred suspension of benzyl-N-[(3R)-1-(4-methoxyphenyl)-2-oxo-azetidin-3-yl]- carbamate (4.616 g, 0.014 mol) in MeCN (260 mL) and H₂O (200 mL), a solution of commercially available CAN (23.26 g, 0.042 mol) in H₂O (50 mL) was added dropwise over 45 min. The resulting mixture was stirred at 0° C. for additional 0.5 h and then NaHCO₃ saturated solution (250 mL) was cautiously added followed by EtOAc (150 mL). A colloidal precipitate was observed, filtered off and washed with additional EtOAc (150 mL). The collected biphasic solution was partitioned and the organic phase was dried over Na₂SO₄. Activated charcoal was added to the solution and the organic phase was filtered through a pad of Celite and evaporated. Immediate trituration with Et₂O afforded the pure title compound (2.29 g, 74%), as an off-white solid. $R_t$=1.54 min. MS (ESI) m/z: 221 [M–H]⁺, 243 [M–Na]⁺, 259 [M–K]⁺. ¹H NMR (DMSO-d₆): δ 7.97 (d, 1H, J=8.7 Hz), 7.94 (bs, 1H), 7.42-7.30 (m, 5H), 5.05 (s, 2H), 4.67 (ddd, 1H, J=8.7, 5.4, 2.7 Hz), 3.40 (t, 1H, J=5.4 Hz,), 3.09 (dd, 1H, J=5.4, 2.7 Hz).

Step 4. Preparation of
[(3R)-2-oxoazetidin-3-yl]-ammonium acetate

Under nitrogen atmosphere, to a 0.05 M solution of benzyl-N-[(3R)-2-oxoazetidin-3-yl]-carbamate (2.29 g, 0.01 mol) in EtOH (210 mL), cyclohexadiene (10.2 mL, 0.104 mol) and 10% Pd on activated charcoal (2.29 g) were sequentially added. The resulting suspension was stirred at r.t. for 16 h, then filtered off on a short pad of Celite. The outcoming solution was immediately trapped into a solution of AcOH (0.66 mL, 0.0115 mmol) in EtOAc (170 mL). Evaporation of solvents under reduced pressure afforded the pure title compound (1.46 g, quant.), as a white solid. ¹H NMR (DMSO-d₆): δ 7.68 (bs, 1H), 3.99 (ddd, 1H, J=5.2, 2.4, 1.2 Hz), 3.32 (t, 1H, J=5.2 Hz), 2.79 (dd, 1H, J=5.2, 2.4 Hz), 1.90 (s, 3H).

Example 1

4-Phenyl-N-[(3S)-2-oxoazetidin-3-yl]-benzamide

Step 1. Preparation of
4-phenyl-N-[(3S)-2-oxoazetidin-3-yl]-benzamide

Under nitrogen atmosphere, at 0° C., to a stirred suspension of [(3S)-2-oxoazetidin-3-yl]-ammonium acetate (0.13 g, 0.89 mmol) in a 3:1 mixture of dry CH₂Cl₂/DMF (4.0 mL), dry Et₃N (0.26 mL, 1.87 mmol) and 4-phenylbenzoyl chloride (0.21 g, 0.98 mmol) were added. The resulting mixture was stirred at r.t. for 6 h, then diluted with methyl ethyl ketone (70 mL) and washed with sat. NaHCO₃ solution (2×15 mL) and brine (10 mL). The organic layer was dried over Na₂SO₄, filtered and concentrated to dryness giving crude product (0.18 g). Trituration with EtOAc afforded the pure title compound (0.10 g, 42%), as a white solid. $R_t$=1.89 min. MS (ESI) m/z: 267 [M–H]⁺, 289 [M–Na]⁺. MS (ESI) m/z: 265 [M–H]⁻. ¹H NMR (DMSO-d₆): δ 9.14 (d, 1H, J=8.5 Hz), 8.05 (bs, 1H), 7.97 (d, 2H, J=8.4 Hz), 7.79 (d, 2H, J=8.4 Hz), 7.74 (d, 2H, J=7.4 Hz), 7.50 (t, 2H, J=7.6 Hz), 7.45-7.38 (m, 1H), 5.09 (ddd, 1H, J=8.1, 5.2, 2.5 Hz), 3.49 (t, 1H, J=5.2 Hz), 3.27 (dd, 1H, J=5.2, 2.5 Hz).

Example 2

4-Phenyl-N-[(3R)-2-oxoazetidin-3-yl]-benzamide

Step 1. Preparation of
4-phenyl-N-[(3R)-2-oxoazetidin-3-yl]-benzamide

Under nitrogen atmosphere, at 0° C., to a stirred suspension of [(3R)-2-oxoazetidin-3-yl]-ammonium acetate (0.050 g, 0.34 mmol) in a 3:1 mixture of dry CH₂Cl₂/DMF (2.0 mL), dry Et₃N (0.10 mL, 0.71 mmol) and 4-phenylbenzoyl chloride (0.081 g, 0.37 mmol) were added. The resulting mixture was stirred at r.t. for 6 h, then diluted with methyl ethyl ketone (40 mL) and washed with sat. NaHCO₃ solution (2×10 mL) and brine (5.0 mL). The organic layer was dried over Na₂SO₄, filtered and concentrated to dryness giving crude product (0.056 g). Trituration with EtOAc afforded the pure title compound (0.021 g, 21%), as a white solid. $R_t$=1.89 min. MS (ESI) m/z: 267 [M–H]⁺, 289 [M–Na]⁺. MS (ESI) m/z: 265 [M–H]⁻. ¹H NMR (DMSO-d₆): δ 9.14 (d, 1H, J=8.5 Hz), 8.05 (bs, 1H), 7.97 (d, 2H, J=8.4 Hz), 7.79 (d, 2H, J=8.4 Hz), 7.74 (d, 2H, J=7.4 Hz), 7.50 (t, 2H, J=7.6 Hz), 7.45-7.38 (m, 1H), 5.09 (ddd, 1H, J=8.1, 5.2, 2.5 Hz), 3.49 (t, 1H, J=5.2 Hz), 3.27 (dd, 1H, J=5.2, 2.5 Hz).

Example 3

N-[(3S)-2-Oxoazetidin-3-yl]-nonanamide

Step 1. Preparation of
N-[(3S)-2-oxoazetidin-3-yl]-nonanamide

Under nitrogen atmosphere, at 0° C., to a stirred suspension of [(3S)-2-oxoazetidin-3-yl]-ammonium acetate (0.60 g, 4.1 mmol) in dry CH₂Cl₂ (48 mL), dry Et₃N (1.20 mL, 8.6 mmol) and nonanoyl chloride (0.81 mL, 4.51 mmol) were added dropwise. The resulting reaction mixture was stirred at r.t. for 8 h, then diluted with CH₂Cl₂ (50 mL) and sequentially washed with sat. NH₄Cl solution (2×10 mL), sat. NaHCO₃ solution (2×10 mL) and brine (5.0 mL). The organic layer was dried over Na₂SO₄, filtered and concentrated to dryness giving crude product (0.70 g). Trituration with EtOAc afforded the pure title compound (0.60 g, 65%), as a white solid. $R_t$=2.13 min. MS (ESI) m/z: 227 [M–H]⁺, 249 [M–Na]⁺, 265 [M–K]⁺. MS (ESI) m/z: 225 [M–H]⁻. ¹H NMR (DMSO-d₆): δ 8.42 (d, 1H, J=8.3 Hz), 7.94 (bs, 1H), 4.83 (ddd, 1H, J=8.3, 5.3, 2.7 Hz), 3.38 (t, 1H, J=5.3 Hz), 3.02 (dd, 1H, J=5.3, 2.7 Hz), 2.08 (t, 2H, J=7.3 Hz), 1.53-1.42 (m, 2H), 1.31-1.18 (m, 10H), 0.86 (t, 3H, J=6.8 Hz).

Example 4

N-[(3R)-2-Oxoazetidin-3-yl]-nonanamide

Step 1. Preparation of
N-[(3R)-2-oxoazetidin-3-yl]-nonanamide

Under nitrogen atmosphere, at 0° C., to a stirred suspension of [(3R)-2-oxoazetidin-3-yl]-ammonium acetate (0.090 g, 0.62 mmol) in dry CH₂Cl₂ (3.0 mL), dry Et₃N (0.18 mL, 1.03 mmol) and nonanoyl chloride (0.122 mL, 0.68 mmol) were added dropwise under nitrogen atmosphere. The resulting reaction mixture was stirred at r.t. for 8 h, then diluted with CH₂Cl₂ (3.0 mL) and sequentially washed with sat. NH₄Cl solution (2×5.0 mL), sat. NaHCO₃ solution (2×5.0 mL) and brine (5.0 mL). The organic layer was dried over Na₂SO₄, filtered and concentrated to dryness giving crude product (0.13 g). Trituration with EtOAc afforded the pure title compound (0.044 g, 32%), as a white solid. $R_t$=2.13 min. MS (ESI) m/z: 227 [M–H]⁺, 249 [M–Na]⁺, 265 [M–K]⁺. MS (ESI) m/z: 225 [M–H]⁻. ¹H NMR (DMSO-d₆): δ 8.42 (d, 1H, J=8.3 Hz), 7.94 (bs, 1H), 4.83 (ddd, 1H, J=8.3, 5.3, 2.7 Hz), 3.38 (t, 1H, J=5.3 Hz), 3.02 (dd, 1H, J=5.3, 2.7

Hz), 2.08 (t, 2H, J=7.3 Hz), 1.53-1.42 (m, 2H), 1.31-1.18 (m, 10H), 0.86 (t, 3H, J=6.8 Hz).

Example 5

(E)-N-[(3S)-2-Oxoazetidin-3-yl]-non-3-enamide

Step 1. Preparation of (E)-non-3-enoic acid

To a vigorously stirred solution of methyl (E)-3-nonenoate (0.1 g, 0.59 mmol) in a 1:1:1 mixture of THF/MeOH/H$_2$O (3.0 mL), LiOH (0.056 g, 2.35 mmol) was added in one portion. The reaction mixture was stirred at r.t. for 1 h, and then solvents were evaporated under reduced pressure. The crude product was diluted with H$_2$O (5.0 mL) and treated with 0.5 M H$_2$SO$_4$ solution until pH 3. After extraction with EtOAc (3×15 mL), the organic layer was dried over Na$_2$SO$_4$, filtered and concentrated to dryness affording the title compound (0.092 g, quant.), as a yellow liquid, which was used in the next step without any further purification. $^1$H NMR (DMSO-d$_6$): δ 12.10 (s, 1H), 5.50-5.40 (m, 2H), 2.93 (d, 2H, J=5.8 Hz), 1.98 (dd, 2H, J=13.6, 6.7 Hz), 1.37-1.19 (m, 6H), 0.86 (t, 3H, J=6.9 Hz).

Step 2. Preparation of (E)-N-[(3S)-2-oxoazetidin-3-yl]-non-3-enamide

Under nitrogen atmosphere, at 0° C., to a stirred solution of (E)-3-nonenoic acid (0.058 g, 0.37 mmol) in dry CH$_2$Cl$_2$ (4.0 mL), dry Et$_3$N (0.10 mL, 0.75 mmol) was added dropwise. Subsequently TBTU (0.12 g, 0.37 mmol) was added at the same temperature and the resulting reaction mixture was stirred for 30 min. Then, [(3S)-2-oxoazetidin-3-yl]-ammonium acetate (0.05 g, 0.34 mmol) was added and the reaction solution was stirred at r.t. for 16 h. The mixture was diluted with CH$_2$Cl$_2$ (10 mL) and washed with sat. NH$_4$Cl solution (10 mL) and sat. NaHCO$_3$ solution (10 mL). The organic layer was dried over Na$_2$SO$_4$, filtered and concentrated to dryness giving a fine powder (0.18 g). Trituration with EtOAc afforded the pure title compound (0.035 g, 46%), as a white solid. R$_t$=2.04 min. MS (ESI) m/z: 225 [M–H]$^+$, 247 [M–Na]$^+$, 263 [M–K]$^+$. $^1$H NMR (DMSO-d$_6$): δ 8.45 (d, 1H, J=8.4 Hz), 7.96 (s, 1H), 5.54-5.41 (m, 2H), 4.81 (ddd, 1H, J=8.4, 5.5, 2.6 Hz), 3.38 (t, 1H, J=5.5 Hz), 3.03 (dd, 1H, J=5.5, 2.6 Hz), 2.83 (d, 2H, J=5.6 Hz), 2.01-1.93 (m, 2H), 1.37-1.19 (m, 6H), 0.86 (t, 3H, J=7.1 Hz).

Example 6

(Z)—N-[(3S)-2-Oxoazetidin-3-yl]-non-3-enamide

Step 1. Preparation of (Z)-non-3-enal

Under nitrogen atmosphere, at 0° C., to a stirred solution of 3-nonen-1-ol (0.4 g, 2.8 mmol) in dry CH$_2$Cl$_2$ (28 mL), Dess-Martin periodinane (1.55 g, 3.66 mmol) was added in one portion. The resulting reaction mixture was stirred at 0° C. for 1 h, then warmed up to r.t. and stirred for additional 1 h. The solution was diluted with pentane (100 mL) and washed with H$_2$O (4×50 mL). The organic layer was dried over Na$_2$SO$_4$, filtered and concentrated to dryness affording the title compound (0.37 g, 94%), which was used in the next step without any further purification. $^1$H NMR (CDCl$_3$): δ 9.65 (t, 1H, J=1.9 Hz), 5.74-5.65 (m, 1H), 5.57-5.49 (m, 1H), 3.18 (dt, 2H, J=7.3, 1.6 Hz), 2.07-1.99 (m, 2H), 1.41-1.22 (m, 6H), 0.88 (t, 3H, J=7.1 Hz).

Step 2. Preparation of (Z)-non-3-enoic acid

To a stirred suspension of 3-nonen-1-al (0.18 g, 1.29 mmol) in t-BuOH (30 mL) and H$_2$O (8.0 mL), 2-methyl-2-butene (1.3 mL, 12.90 mmol) and NaH$_2$PO$_4$ (0.37 g, 3.05 mmol) were added in one portion. The resulting reaction mixture was stirred for 20 min, then NaClO$_2$ (0.83 g, 9.22 mmol) was added in one portion and stirring was maintained for additional 1 h. The solution was then acidified with 1N HCl solution until pH 4 and product was extracted with CH$_2$Cl$_2$ (3×15 mL). The organic layer was dried over Na$_2$SO$_4$, filtered and concentrated to dryness affording the title compound (0.20 g, quant.), which was used in the next step without any further purification. R$_t$=2.15 min. MS (ESI) m/z: 155 [M–H]$^-$. $^1$H NMR (DMSO-d$_6$): δ 12.16 (s, 1H), 5.53-5.44 (m, 2H), 3.00-2.97 (m, 2H), 2.03-1.95 (m, 2H), 1.36-1.18 (m, 6H), 0.86 (t, 3H, J=7.1 Hz).

Step 3. Preparation of (Z)—N-[(3S)-2-oxoazetidin-3-yl]-non-3-enamide

Under nitrogen atmosphere, at 0° C., to a stirred solution of (Z)-3-nonenoic acid (0.059 g, 0.38 mmol) in dry CH$_2$Cl$_2$ (3.0 mL), dry Et$_3$N (0.1 mL, 0.71 mmol) was added dropwise. Subsequently TBTU (0.12 g, 0.38 mmol) was added at the same temperature and the resulting reaction mixture was stirred for 30 min. Then [(3S)-2-oxoazetidin-3-yl]-ammonium acetate (0.050 g, 0.34 mmol) was added and the reaction solution was stirred at r.t. for 16 h. The mixture was diluted with CH$_2$Cl$_2$ (15 mL) and washed with sat. NH$_4$Cl solution (2×10 mL) and sat. NaHCO$_3$ solution (2×10 mL). The organic layer was dried over Na$_2$SO$_4$, filtered and concentrated to dryness giving a fine powder (0.165 g). Trituration with EtOAc afforded the pure title compound (0.034 g, 45%), as a white solid. R$_t$=1.98 min. MS (ESI) m/z: 225 [M–H]$^+$, 247 [M–Na]$^+$, 263 [M–K]$^+$. MS (ESI) m/z: 223 [M–H]$^-$. $^1$H NMR (DMSO-d$_6$): δ 8.50 (d, 1H, J=8.4 Hz), 7.97 (s, 1H), 5.52-5.42 (m, 2H), 4.82 (ddd, 1H, J=8.1, 5.4, 2.5 Hz), 3.39 (t, 1H, J=5.4 Hz), 3.03 (dd, 1H, J=5.4, 2.5 Hz), 2.94-2.86 (m, 2H), 2.04-1.96 (m, 2H), 1.37-1.18 (m, 6H), 0.86 (t, 3H, J=7.1 Hz).

Example 7

7-Phenyl-N-[(3S)-2-Oxoazetidin-3-yl]-heptanamide

Step 1. Preparation of 7-phenyl-N-[(3S)-2-oxoazetidin-3-yl]-heptanamide

Under nitrogen atmosphere, at 0° C., to a stirred solution of 7-phenylheptanoic acid (0.065 mL, 0.23 mmol) in dry CH$_2$Cl$_2$ (3.0 mL), dry Et$_3$N (0.06 mL, 0.46 mmol) was added dropwise. Subsequently TBTU (0.073 g, 0.23 mmol) was added at the same temperature and the resulting reaction mixture was stirred for 30 min. Then [(3S)-2-oxoazetidin-3-yl]-ammonium acetate (0.030 g, 0.21 mmol) was added and the reaction solution was stirred at r.t. for 16 h. The mixture was diluted with CH$_2$Cl$_2$ (20 mL) and washed with sat. NH$_4$Cl solution (2×10 mL), sat. NaHCO$_3$ solution (2×10 mL) and brine (10 mL). The organic layer was dried over Na$_2$SO$_4$, filtered and concentrated to dryness giving crude product (0.054 g). Trituration with EtOAc afforded the pure title compound (0.022 g, 38%), as a white solid. R$_t$=2.19 min. MS (ESI) m/z: 275 [M–H]$^+$, 297 [M–Na]$^+$, 313

[M−K]⁺. ¹H NMR (DMSO-d₆): δ 8.43 (d, 1H, J=8.5 Hz,), 7.94 (bs, 1H), 7.29-7.23 (m, 2H), 7.20-7.13 (m, 3H), 4.82 (ddd, 1H, J=8.2, 5.3, 2.6 Hz,), 3.38 (t, 1H, J=5.3 Hz), 3.02 (dd, 1H, J=5.3, 2.6 Hz), 2.59-2.53 (m, 2H), 2.08 (t, 2H, J=7.4 Hz), 1.60-1.42 (m, 4H), 1.32-1.21 (m, 4H).

Example 8

7-Phenyl-N-[(3R)-2-Oxoazetidin-3-yl]-heptanamide

Step 1. Preparation of 7-phenyl-N-[(3R)-2-oxoazetidin-3-yl]-heptanamide

Under nitrogen atmosphere, at 0° C., to a stirred solution of 7-phenylheptanoic acid (0.065 mL, 0.23 mmol) in dry CH₂Cl₂ (3.0 mL), dry Et₃N (0.06 mL, 0.46 mmol) was added dropwise. Subsequently TBTU (0.073 g, 0.23 mmol) was added at the same temperature and the resulting reaction mixture was stirred for 30 min. Then [(3R)-2-oxoazetidin-3-yl]-ammonium acetate (0.050 g, 0.34 mmol) was added and the reaction solution was stirred at r.t. for 16 h. The mixture was diluted with CH₂Cl₂ (20 mL) and washed with sat. NH₄Cl solution (2×10 mL), sat. NaHCO₃ solution (2×10 mL) and brine (10 mL). The organic layer was dried over Na₂SO₄, filtered and concentrated to dryness, giving crude product (0.074 g). Trituration with EtOAc afforded the pure title compound (0.032 g, 34%), as a white solid. R$_f$=2.19 min. MS (ESI) m/z: 275 [M−H]⁺, 297 [M−Na]⁺, 313 [M−K]⁺. ¹H NMR (DMSO-d₆): δ 8.43 (d, 1H, J=8.5 Hz,), 7.94 (bs, 1H), 7.29-7.23 (m, 2H), 7.20-7.13 (m, 3H), 4.82 (ddd, 1H, J=8.2, 5.3, 2.6 Hz,), 3.38 (t, 1H, J=5.3 Hz), 3.02 (dd, 1H, J=5.3, 2.6 Hz), 2.59-2.53 (m, 2H), 2.08 (t, 2H, J=7.4 Hz), 1.60-1.42 (m, 4H), 1.32-1.21 (m, 4H).

Example 9

4-Benzyloxy-N-[(3S)-2-oxoazetidin-3-yl]-butanamide

Step 1. Preparation of 4-benzyloxy-N-[(3S)-2-oxoazetidin-3-yl]-butanamide

Under nitrogen atmosphere, at 0° C., to a stirred solution of 4-benzyloxybutyric acid (0.040 g, 0.23 mmol) in dry CH₂Cl₂ (3.0 mL), dry Et₃N (0.060 mL, 0.45 mmol) was added dropwise. Subsequently TBTU (0.073 g, 0.23 mmol) was added at the same temperature and the resulting reaction mixture was stirred for 30 min. Then [(3S)-2-oxoazetidin-3-yl]-ammonium acetate (0.030 g, 0.21 mmol) was added and the reaction mixture was stirred at r.t. for 16 h. The reaction mixture was concentrated to dryness giving crude product (0.069 g). Purification by typical silica gel flash chromatography eluting with EtOAc afforded the pure title compound (0.024 g, 23%), as a white solid. R$_f$=1.57 min. MS (ESI) m/z: 263 [M−H]⁺, 285 [M−Na]⁺, 301 [M−K]⁺. ¹H NMR (DMSO-d₆): δ 8.48 (d, 1H, J=8.4 Hz), 7.94 (bs, 1H), 7.37-7.24 (m, 5H), 4.83 (ddd, 1H, J=8.2, 5.4, 2.6 Hz), 4.44 (s, 2H), 3.41 (t, 2H, J=6.4 Hz), 3.37 (d, 1H, J=5.4 Hz), 3.02 (dd, 1H, J=5.4, 2.6 Hz), 2.25-2.14 (m, 2H), 1.76 (p, 2H, J=7.0 Hz).

Example 10

4-Benzyloxy-N-[(3R)-2-oxoazetidin-3-yl]-butanamide

Step 1. Preparation of 4-benzyloxy-N-[(3R)-2-oxoazetidin-3-yl]-butanamide

Under nitrogen atmosphere, at 0° C., to a stirred solution of 4-benzyloxybutyric acid (0.073 g, 0.37 mmol) in dry CH₂Cl₂ (3.0 mL), dry Et₃N (0.10 mL, 0.75 mmol) was added dropwise under nitrogen atmosphere. Subsequently TBTU (0.12 g, 0.37 mmol) was added at the same temperature and the resulting reaction mixture was stirred for 30 min. Then (3R)-2-oxoazetidin-3-yl]-ammonium acetate (0.050 g, 0.34 mmol) was added and the reaction mixture was stirred at r.t. for 16 h. The reaction mixture was concentrated to dryness giving crude product (0.31 g). Purification by typical silica gel flash chromatography eluting with EtOAc afforded the pure title compound (0.043 g, 48%), as a white solid. R$_f$=1.57 min. MS (ESI) m/z: 263 [M−H]⁺, 285 [M−Na]⁺, 301 [M−K]⁺. ¹H NMR (DMSO-d₆): δ 8.48 (d, 1H, J=8.4 Hz), 7.94 (bs, 1H), 7.37-7.24 (m, 5H), 4.83 (ddd, 1H, J=8.2, 5.4, 2.6 Hz), 4.44 (s, 2H), 3.41 (t, 2H, J=6.4 Hz), 3.37 (d, 1H, J=5.4 Hz), 3.02 (dd, 1H, J=5.4, 2.6 Hz,), 2.25-2.14 (m, 2H), 1.76 (p, 2H, J=7.0 Hz).

Example 11

4-Benzyloxy-N-[(3S)-2-oxoazetidin-3-yl]-benzamide

Step 1. Preparation of 4-benzyloxy-N-[(3S)-2-oxoazetidin-3-yl]-benzamide

Under nitrogen atmosphere, at 0° C., to a stirred suspension of [(3S)-2-oxoazetidin-3-yl]-ammonium acetate (0.030 g, 0.21 mmol) in dry CH₂Cl₂ (3.0 mL), dry Et₃N (0.06 mL, 0.44 mmol) and benzyloxy benzoyl chloride (0.056 mg, 0.23 mmol) were added dropwise. The resulting reaction mixture was stirred at r.t. for 12 h, then concentrated to dryness giving a crude product (0.17 g). Purification by typical silica gel flash chromatography, eluting with EtOAc, and trituration with CH₂Cl₂ afforded the pure title compound (0.034 mg, 28%), as a white solid. R$_f$=1.99 min. MS (ESI) m/z: 297 [M−H]⁺, 319 [M−Na]⁺, 335 [M−K]⁺. ¹H NMR (DMSO-d₆): δ 8.92 (d, 1H, J=8.3 Hz), 8.01 (s, 1H), 7.87-7.82 (m, 2H), 7.49-7.31 (m, 5H), 7.12-7.07 (m, 2H), 5.17 (s, 2H), 5.03 (ddd, 1H, J=8.3, 5.5, 2.7 Hz), 3.45 (t, 1H, J=5.2 Hz), 3.23 (dd, 1H, J=5.2, 2.7 Hz).

Example 12

4-Benzyloxy-N-[(3R)-2-oxoazetidin-3-yl]-benzamide

Step 1. Preparation of 4-benzyloxy-N-[(3R)-2-oxoazetidin-3-yl]-benzamide

Under nitrogen atmosphere, at 0° C., to a stirred suspension of [(3R)-2-oxoazetidin-3-yl]-ammonium acetate (0.050 g, 0.34 mmol) in dry CH₂Cl₂ (4.0 mL), dry Et₃N (0.1 mL, 0.71 mmol) and 4-benzyloxy benzoyl chloride (0.092 g, 0.37 mmol) were added dropwise. The resulting reaction mixture was stirred at r.t. for 12 h, then concentrated to dryness giving crude product (0.23 g). Purification by typical silica gel flash chromatography, eluting with EtOAc, and trituration with CH₂Cl₂ afforded the pure title compound (0.020 g, 20%), as a white solid. R$_f$=1.99 min. MS (ESI) m/z: 297 [M−H]⁺, 319 [M−Na]⁺, 335 [M−K]⁺. ¹H NMR (DMSO-d₆): δ 8.92 (d, 1H, J=8.3 Hz), 8.01 (s, 1H), 7.87-7.82 (m, 2H), 7.49-7.31 (m, 5H), 7.12-7.07 (m, 2H), 5.17 (s, 2H), 5.03 (ddd, 1H, J=8.3, 5.5, 2.7 Hz), 3.45 (t, 1H, J=5.2 Hz), 3.23 (dd, 1H, J=5.2, 2.7 Hz).

Example 13

1-Methyl-N-[(3S)-2-oxoazetidin-3-yl]-cyclohexane-carboxamide

Step 1. Preparation of 1-methyl-N-[(3S)-2-oxoazetidin-3-yl]-cyclohexane-carboxamide Under nitrogen atmosphere, at 0° C., to a stirred suspension of [(3S)-2-oxoazetidin-3-yl]-ammonium acetate (0.030 g, 0.21 mmol) in dry $CH_2Cl_2$ (3.0 mL), dry $Et_3N$ (0.06 mL, 0.44 mmol) and 1-methyl-1-cyclohexanecarboxylic acid chloride (0.036 g, 0.23 mmol) were added dropwise. The resulting reaction mixture was stirred at r.t. for 12 h, then concentrated to dryness giving a crude product (0.16 g). Purification by typical silica gel flash chromatography, eluting with EtOAc, and trituration with $CH_2Cl_2$ afforded the pure title compound (0.034 g, 40%), as a white solid. $R_t$=1.56 min. MS (ESI) m/z: 211 $[M-H]^+$, 233 $[M-Na]^+$, 249 $[M-K]^+$. $^1H$ NMR (DMSO-$d_6$): δ 8.05 (d, 1H, J=8.4 Hz), 7.89 (bs, 1H), 4.84 (ddd, 1H, J=8.4, 5.3, 2.7 Hz), 3.36 (t, 1H, J=5.3 Hz), 3.10 (dd, 1H, J=5.3, 2.7 Hz), 1.97-1.86 (m, 2H), 1.51-1.37 (m, 3H), 1.36-1.10 (m, 5H), 1.03 (s, 3H).

Example 14

1-Methyl-N-[(3R)-2-oxoazetidin-3-yl]-cyclohexane-carboxamide

Step 1. Preparation of 1-methyl-N-[(3R)-2-oxoazetidin-3-yl]-cyclohexane-carboxamide Under nitrogen atmosphere, at 0° C., to a stirred suspension of [(3R)-2-oxoazetidin-3-yl]-ammonium acetate (0.050 g, 0.34 mmol) in dry $CH_2Cl_2$ (4.0 mL), dry $Et_3N$ (0.10 mL, 0.71 mmol) and 1-methyl-1-cyclohexanecarboxylic acid chloride (0.06 g, 0.37 mmol) were added dropwise. The resulting reaction mixture was stirred at r.t. for 12 h, then concentrated to dryness affording a crude product (0.27 g). Purification by typical silica gel flash chromatography, eluting with EtOAc, and trituration with $CH_2Cl_2$ afforded the pure title compound (0.042 g, 57%), as a white solid. $R_t$=1.56 min. MS (ESI) m/z: 211 $[M-H]^+$, 233 $[M-Na]^+$, 249 $[M-K]^+$. $^1H$ NMR (DMSO-$d_6$): δ 8.05 (d, 1H, J=8.4 Hz), 7.89 (bs, 1H), 4.84 (ddd, 1H, J=8.4, 5.3, 2.7 Hz), 3.36 (t, 1H, J=5.3 Hz), 3.10 (dd, 1H, J=5.3, 2.7 Hz), 1.97-1.86 (m, 2H), 1.51-1.37 (m, 3H), 1.36-1.10 (m, 5H), 1.03 (s, 3H).

Example 15

(E)-N-[(3S)-2-Oxoazetidin-3-yl]-4-phenyl-but-3-enamide

Step 1. Preparation of (E)-N-[(3S)-2-Oxoazetidin-3-yl]-4-phenyl-but-3-enamide

Under nitrogen atmosphere, at 0° C., to a stirred solution of trans-styrylacetic acid (0.061 g, 0.38 mmol) in dry $CH_2Cl_2$ (2.0 mL), dry $Et_3N$ (0.10 mL, 0.75 mmol) was added dropwise. Subsequently TBTU (0.12 g, 0.38 mmol) was added at the same temperature and the resulting reaction mixture was stirred for 30 min. Then [(3S)-2-oxoazetidin-3-yl]-ammonium acetate (0.050 g, 0.34 mmol) was added and the reaction solution was stirred at r.t. for 16 h. The mixture was diluted with $CH_2Cl_2$ (10 mL) and washed with sat. $NH_4Cl$ solution (10 mL), sat. $NaHCO_3$ solution (10 mL) and brine (10 mL). The organic layer was dried over $Na_2SO_4$, filtered and concentrated to dryness giving a fine powder (0.22 g). Purification by typical silica gel flash chromatography (Cy/EtOAc from 100:0 to 20:70) afforded the pure title compound (0.035 g, 44%), as a white solid. $R_t$=1.60 min. MS (ESI) m/z: 231 $[M-H]^+$, 253 $[M-Na]^+$, 269 $[M-K]^+$. MS (ESI) m/z: 229 $[M-H]^-$. $^1H$ NMR (DMSO-$d_6$): δ 8.59 (d, 1H, J=8.4 Hz), 7.98 (s, 1H), 7.40 (d, 2H, J=7.4 Hz), 7.32 (t, 2H, J=7.4 Hz), 7.23 (t, 1H, J=7.4 Hz), 6.48 (d, 1H, J=16.0 Hz), 6.32 (dt, 1H, J=16.0, 7.0 Hz), 4.86 (ddd, 1H, J=8.4, 5.4, 2.5 Hz), 3.40 (t, 1H, J=5.4 Hz), 3.12-3.05 (m, 3H).

Example 16

5-Cyclohexyl-N-[(3S)-2-oxoazetidin-3-yl]-pentanamide

Step 1. Preparation of 5-cyclohexyl-N-[(3S)-2-oxoazetidin-3-yl]-pentanamide

Under nitrogen atmosphere, at 0° C., to a stirred solution of 5-cyclohexylpentanoic acid (0.072 mL, 0.38 mmol) in dry $CH_2Cl_2$ (3.0 mL), dry $Et_3N$ (0.1 mL, 0.71 mmol) was added dropwise. Subsequently TBTU (0.12 g, 0.38 mmol) was added at the same temperature and the resulting reaction mixture was stirred for 30 min. Then [(3S)-2-oxoazetidin-3-yl]-ammonium acetate (0.050 g, 0.34 mmol) was added, and the reaction mixture was stirred at r.t. for 16 h. The mixture was diluted with $CH_2Cl_2$ (10 mL), and washed with sat. $NH_4Cl$ solution (10 mL) and sat. $NaHCO_3$ solution (10 mL). The organic layer was dried over $Na_2SO_4$, filtered and concentrated giving a fine powder (0.14 g). Trituration with $Et_2O$ afforded the pure title compound (0.061 g, 71%), as a white solid. $R_t$=2.31 min. MS (ESI) m/z: =253 $[M-H]^+$, 275 $[M-Na]^+$, 291 $[M-K]^+$. MS (ESI) m/z: =251 $[M-H]^-$. $^1H$-NMR (DMSO-$d_6$): δ 8.44 (d, 1H, J=8.4 Hz), 7.95 (s, 1H), 4.86-4.80 (ddd, 1H, J=8.4, 5.4, 2.7 Hz), 3.38 (t, 1H, J=5.4 Hz), 3.02 (dd, 1H, J=5.4, 2.7 Hz), 2.08 (t, 2H, J=7.6 Hz), 1.70-1.55 (s, 5H), 1.46 (p, 2H, J=7.6 Hz), 1.30-1.10 (m, 8H), 0.90-0.76 (m, 2H).

Example 17

6-Cyclohexyl-N-[(3S)-2-oxoazetidin-3-yl]-hexanamide

Step 1. Preparation of 4-cyclohexylbutanal

Under nitrogen atmosphere, at −78° C., to a stirred solution of oxalyl chloride (0.28 mL, 3.3 mmol) in dry $CH_2Cl_2$ (20 mL), DMSO (0.22 mL, 3.08 mmol) was added dropwise. After 15 min, a solution of 4-cyclohexylbutanol (0.40 g, 2.56 mmol) in dry $CH_2Cl_2$ (5.0 mL) was slowly added and the resulting reaction mixture was stirred at −78° C. for 1 h. Then $Et_3N$ (1.0 mL, 7.7 mmol) was added dropwise. The resulting solution was warmed up to r.t., and after evaporation of the solvents, the crude mixture was taken up in $Et_2O$ (20 mL) and washed with sat. $NH_4Cl$ solution (2×10 mL). The organic layer was dried over $Na_2SO_4$, filtered and concentrated to dryness giving the title compound (0.40 g), which was used in the next step without any further purification. $^1H$-NMR (DMSO-$d_6$): δ 9.65 (t, 1H, J=1.7 Hz), 2.39 (td, 2H, J=7.3, 1.7 Hz), 1.71-1.57 (m, 6H), 1.52 (p, 2H, J=7.8 Hz), 1.25-1.08 (m, 7H), 0.91-0.78 (t, 2H).

Step 2. Preparation of ethyl (E)-6-cyclohexylhex-2-enoate

Under nitrogen atmosphere, at 0° C., to a stirred suspension of NaH (95% pure, 0.069 g, 2.86 mmol) in dry THF (15 mL), a solution of triethyl phosphonoacetate (0.566 mL, 2.86 mmol) in dry THF (5.0 mL) was added dropwise. The resulting mixture was stirred for 15 min, then a solution of 4-cyclohexylbutanal (0.4 g, 2.6 mmol) in dry THF (5.0 mL) was added dropwise to the reaction mixture. After stirring for 16 h, $H_2O$ (20 mL) and $Et_2O$ (30.0 mL) were sequentially added, and the solution was stirred for additional 15 min. The organic phase was separated and dried over $Na_2SO_4$, filtered and concentrated to dryness, giving a crude product (0.856 g). Purification by typical silica gel flash chromatography (Cy/EtOAc, from 100:0 to 83:17) afforded the pure title compound (0.513 g, 89%, over two steps), as an oil. $R_t$=1.62 min. MS (ESI) m/z: 225 [M–H]$^+$, 247 [M–Na]$^-$. $^1$H NMR (DMSO-d$_6$): δ 6.87 (dt, 1H, J=15.7, 7.0 Hz), 5.84 (dt, 1H, J=15.7, 1.6 Hz), 4.10 (q, 2H, J=7.1 Hz), 2.17 (qd, 2H, J=7.1, 1.2 Hz), 1.71-1.54 (m, 5H), 1.41 (p, 2H, J=7.5 Hz), 1.26-1.07 (m, 9H), 0.91-0.78 (m, 2H).

Step 3. Preparation of ethyl 6-cyclohexylhexanoate

A 0.05 M solution of ethyl (E)-6-cyclohexylhex-2-enoate (0.25 g, 1.12 mmol) in EtOH (22 mL) was passed through the H-Cube® hydrogenator flow reactor, provided with a 10% Pd/C cartridge (flow rate: 1.0 mL/min; P=10 bars; T=45° C.). The outcoming solution was looped through the H-Cube® for a second hydrogenation step in the same reaction conditions. Evaporation of solvent afforded the title compound (0.233 g), as a colorless liquid, which was used in the next step without any further purification. $^1$H NMR (DMSO-d$_6$): δ 4.04 (q, 2H, J=7.2 Hz), 2.26 (t, 2H, J=7.2 Hz), 1.70-1.55 (m, 5H), 1.51 (p, 2H, J=7.1 Hz), 1.30-1.07 (m, 13H), 0.89-0.77 (m, 2H).

Step 4. Preparation of 6-cyclohexylhexanoic acid

Under vigorous stirring, to a solution of ethyl 6-cyclohexylhexanoate (0.23 g, 1.02 mmol) in a 1:1:1 mixture of THF/MeOH/H2O (6.0 mL), LiOH (0.098 g, 4.07 mmol) was added in one portion. After 1 h at the same temperature, evaporation of the solvents gave a crude mixture which was diluted with $H_2O$ (5.0 mL) and treated with 0.5 M $H_2SO_4$ solution until pH 3. After extraction with EtOAc (3×15 mL), the organic layer was dried over $Na_2SO_4$, filtered and concentrated to dryness, affording the crude title compound (0.16 g), as yellowish oil, which was used in the next step without any further purification. $R_t$=0.63 min. MS (ESI) m/z: 197 [M–H]$^-$. $^1$H-NMR (DMSO-d$_6$): δ 11.95 (s, 1H), 2.18 (t, 2H, J=7.4 Hz), 1.70-1.56 (m, 5H), 1.48 (p, 2H, J=7.0 Hz), 1.32-1.07 (m, 10H), 0.91-0.77 (m, 2H).

Step 5. Preparation of 6-cyclohexyl-N-[(3S)-2-oxoazetidin-3-yl]-hexanamide

Under nitrogen atmosphere, at 0° C., to a stirred solution of 6-cyclohexyl-hexanoic acid (0.111 g, 0.56 mmol) in dry $CH_2Cl_2$ (6.0 mL), dry $Et_3N$ (0.149 mL, 1.07 mmol) was added dropwise. Subsequently TBTU (0.18 g, 0.56 mmol) was added at the same temperature and the resulting reaction mixture was stirred for 30 min. Then [(3S)-2-oxoazetidin-3-yl]-ammonium acetate (0.075 g, 0.51 mmol) was added, and the reaction mixture was left at r.t. for 16 h. The mixture was diluted with $CH_2Cl_2$ (15 mL), and washed with sat. $NH_4Cl$ solution (2×20 mL), sat. $NaHCO_3$ solution (2×20 mL) and brine (20 mL). The organic layer was dried over $Na_2SO_4$, filtered and concentrated to afford a fine powder (0.22 g). Trituration with $Et_2O$ afforded the pure title compound (0.070 g, 52%), as a white solid. $R_t$=2.54 min. MS (ESI) m/z: 267 [M–H] 289 [M–Na] 305 [M–K]$^+$. MS (ESI) m/z: 265 [M–H]$^-$. $^1$H NMR (DMSO-d6): δ 8.43 (d, 1H, J=8.3 Hz), 7.94 (s, 1H), 4.82 (ddd, 1H, J=8.3, 5.4, 2.6 Hz), 3.38 (t, 1H, J=5.4 Hz), 3.02 (dd, 1H, J=2.6, 5.4 Hz), 2.08 (t, 2H, J=7.5 Hz), 1.70-1.56 (m, 5H), 1.48 (p, 2H, J=7.1 Hz), 1.31-1.07 (m, 10H), 0.90-0.77 (m, 2H).

Example 18

3-(4-Phenylphenyl)-N-[(3S)-2-oxoazetidin-3-yl]-propanamide

Step 1. Preparation of 3-(4-phenylphenyl)-N-[(3S)-2-oxoazetidin-3-yl]-propanamide Under nitrogen atmosphere, at 0° C., to a stirred solution of 3-(4-phenylphenyl)-propanoic acid (0.07 g, 0.31 mmol) in a 3:1 mixture of dry $CH_2Cl_2$/DMF (5.0 mL), dry $Et_3N$ (0.09 mL, 0.68 mmol) was added dropwise. Subsequently TBTU (0.11 g, 0.34 mmol) was added at the same temperature and the resulting reaction mixture was stirred for 30 min. Then [(3S)-2-oxoazetidin-3-yl]-ammonium acetate (0.05 g, 0.34 mmol) was added, and the reaction mixture was left at r.t. for 16 h. The mixture was diluted with $CH_2Cl_2$ (15 mL), and washed with sat. $NH_4Cl$ solution (2×20 mL), sat. $NaHCO_3$ solution (2×20 mL) and brine (20 mL). The organic layer was dried over $Na_2SO_4$, filtered and concentrated to dryness to afford a crude powder (0.12 g). Trituration with $Et_2O$ gave the pure title compound (0.016 g, 17%), as a grey solid. $R_t$=2.10 min; MS (ESI) m/z: 295 [M–H]$^+$. MS (ESI) m/z: 293 [M–H]$^-$. $^1$H NMR (DMSO-d$_6$) δ 8.54 (d, 1H, J=8.3 Hz), 7.96 (s, 1H), 7.68-7.60 (m, 2H), 7.59-7.54 (m, 2H), 7.49-7.40 (m, 2H), 7.37-7.27 (m, 3H), 4.84 (ddd, 1H, J=8.3, 5.5, 2.6 Hz), 3.41-3.38 (m, 1H), 3.01 (dd, 1H, J=5.3, 2.7 Hz), 2.85 (t, 2H, J=7.8 Hz), 2.44 (d, 2H, J=7.8 Hz).

Example 19

3-Phenyl-N-[(3S)-2-oxoazetidin-3-yl]-propanamide

Step 1. Preparation of 3-phenyl-N-[(3S)-2-Oxoazetidin-3-yl]-propanamide

Under nitrogen atmosphere, at 0° C., to a stirred suspension of [(3S)-2-oxoazetidin-3-yl]-ammonium acetate (0.050 g, 0.34 mmol) in dry $CH_2Cl_2$ (5.0 mL), dry $Et_3N$ (0.10 mL, 0.71 mmol) and 3-phenylpropanoyl chloride (0.056 mL, 0.38 mmol) were added dropwise. The resulting reaction mixture was stirred at r.t. for 16 h, then diluted with $CH_2Cl_2$ (15 mL) and washed with sat. $NH_4Cl$ solution (2×20 mL), sat. $NaHCO_3$ solution (2×20 mL) and brine (20 mL). The organic layer was dried over $Na_2SO_4$, filtered and concentrated to dryness giving a crude product (0.11 g). Trituration with EtOAc afforded the pure title compound (0.080 g, 15%), as a white solid. $R_t$=1.40 min. MS (ESI) m/z: 219 [M–H]$^+$, 241 [M–Na]$^+$, 257 [M–K]$^+$. MS (ESI) m/z: 217 [M–H]$^-$. $^1$H NMR (DMSO-d$_6$): δ 8.51 (d, 1H, J=8.2 Hz), 7.96 (s, 1H), 7.29-7.24 (m, 2H), 7.22-7.14 (m, 3H), 4.87-4.80 (m, 1H), 3.38 (t, 1H, J=5.4 Hz), 2.99 (dd, 1H, J=5.4, 2.6 Hz), 2.81 (t, 2H, J=7.9 Hz), 2.41 (t, 2H, J=7.9 Hz).

Example 20

3-Phenyl-N-[(3R)-2-oxoazetidin-3-yl]-propanamide

Under nitrogen atmosphere, at 0° C., to a stirred suspension of [(3R)-2-oxoazetidin-3-yl]-ammonium acetate (0.060 g, 0.41 mmol) in dry CH$_2$Cl$_2$ (5.0 mL), dry Et$_3$N (0.11 mL, 0.86 mmol) and 3-phenylpropanoyl chloride (0.066 mL, 0.45 mmol) were added dropwise. The resulting reaction mixture was stirred at r.t. for 16 h, then diluted with CH$_2$Cl$_2$ (15 mL) and washed with sat. NH$_4$Cl solution (2×20 mL), sat. NaHCO$_3$ solution (2×20 mL) and brine (20 mL). The organic layer was dried over Na$_2$SO$_4$, filtered and concentrated to dryness giving a crude product (0.074 g). Trituration with EtOAc afforded the pure title compound (0.029 g, 32%), as a white solid. R$_t$=1.40 min. MS (ESI) m/z: 219 [M–H]$^+$, 241 [M–Na]$^+$, 257 [M–K]$^+$. MS (ESI) m/z: 217 [M–H]$^-$. $^1$H NMR (DMSO-d$_6$): δ 8.51 (d, 1H, J=8.2 Hz), 7.96 (s, 1H), 7.29-7.24 (m, 2H), 7.22-7.14 (m, 3H), 4.87-4.80 (m, 1H), 3.38 (t, 1H, J=5.4 Hz), 2.99 (dd, 1H, J=5.4, 2.6 Hz), 2.81 (t, 2H, J=7.9 Hz), 2.41 (t, 2H, J=7.9 Hz).

Example 21

N-[(3S)-2-Oxoazetidin-3-yl]-heptanamide

Step 1. Preparation of
N-[(3S)-2-oxoazetidin-3-yl]-heptanamide

Under nitrogen atmosphere, at 0° C., to a stirred suspension of [(3S)-2-oxoazetidin-3-yl]-ammonium acetate (0.050 g, 0.34 mmol) in dry CH$_2$Cl$_2$ (5.0 mL), dry Et$_3$N (0.1 mL, 0.71 mmol) and heptanoyl chloride (0.058 mL, 0.38 mmol) were added dropwise. The resulting reaction mixture was stirred at r.t. for 16 h, then diluted with CH$_2$Cl$_2$ (15 mL) and washed with sat. NH$_4$Cl solution (2×20 mL), sat. NaHCO$_3$ solution (2×20 mL) and brine (20 mL). The organic layer was dried over Na$_2$SO$_4$, filtered and concentrated to dryness giving a crude product (0.13 g). Purification by typical silica gel flash chromatography (DCM/MeOH, from 100:0 to 96:4) afforded the pure title compound (0.023 g, 34%), as a white solid. R$_t$=1.63 min. MS (ESI) m/z: 199 [M–H]$^+$, 221 [M–Na]$^+$, 237 [M–K]$^+$. MS (ESI) m/z: 197 [M–H]$^-$. $^1$H NMR (DMSO-d$_6$): δ 8.43 (d, 1H, J=8.3 Hz), 7.94 (s, 1H), 4.82 (ddd, 1H, J=8.3, 5.4, 2.7 Hz), 3.38 (t, 1H, J=5.4 Hz), 3.02 (dd, 1H, J=5.4, 2.7 Hz), 2.08 (t, 2H, J=7.4 Hz), 1.53-1.42 (m, 2H), 1.32-1.17 (m, 6H), 0.85 (t, 3H, J=7.0 Hz).

Example 22

N-[(3S)-2-Oxoazetidin-3-yl]-octanamide

Step 1. Preparation of
N-[(3S)-2-oxoazetidin-3-yl]-octanamide

Under nitrogen atmosphere, at 0° C., to a stirred suspension of [(3S)-2-oxoazetidin-3-yl]-ammonium acetate (0.060 g, 0.41 mmol) in dry CH$_2$Cl$_2$ (5.0 mL), dry Et$_3$N (0.11 mL, 0.86 mmol) and octanoyl chloride (0.076 mL, 0.45 mmol) were added dropwise. The resulting reaction mixture was stirred at r.t. for 16 h, then diluted with CH$_2$Cl$_2$ (15 mL) and washed with sat. NH$_4$Cl solution (2×20 mL), sat. NaHCO$_3$ solution (2×20 mL) and brine (20 mL). The organic layer was dried over Na$_2$SO$_4$, filtered and concentrated to dryness giving a crude product (0.060 g). Trituration in EtOAc afforded the pure title compound (0.019 g, 22%), as a white solid. R$_t$=1.88 min. MS (ESI) m/z: 213 [M–H]$^+$, 251 [M–K]$^+$. $^1$H NMR (DMSO-d$_6$): δ 8.43 (d, 1H, J=8.2 Hz), 7.94 (s, 1H), 4.82 (ddd, 1H, J=8.2, 5.4, 2.4 Hz), 3.38 (t, 1H, J=5.4 Hz), 3.02 (dd, 1H, J=5.4, 2.4 Hz), 2.08 (t, 2H, J=7.4 Hz), 1.53-1.42 (m, 2H), 1.32-1.17 (m, 8H), 0.85 (t, 3H, J=7.0 Hz).

Example 23

N-[(3S)-2-Oxoazetidin-3-yl]-decanamide

Step 1. Preparation of
N-[(3S)-2-oxoazetidin-3-yl]-decanamide

Under nitrogen atmosphere, at 0° C., to a stirred suspension of [(3S)-2-oxoazetidin-3-yl]-ammonium acetate (0.050 g, 0.34 mmol) in dry CH$_2$Cl$_2$ (6.0 mL), dry Et$_3$N (0.11 mL, 0.71 mmol) and decanoyl chloride (0.077 mL, 0.38 mmol) were added dropwise. The resulting reaction mixture was stirred at r.t. for 16 h, then diluted with CH$_2$Cl$_2$ (15 mL) and washed with sat. NH$_4$Cl solution (2×20 mL), sat. NaHCO$_3$ solution (2×20 mL) and brine (20 mL). The organic layer was dried over Na$_2$SO$_4$, filtered and concentrated to dryness affording a crude product (0.12 g) which after purification by typical silica gel flash chromatography (DCM/MeOH, from 100:0 to 96:4) afforded the pure title compound (0.051 g, 63%), as a white solid. R$_t$=2.31 min. MS (ESI) m/z: 241 [M–H]$^+$, 263 [M–Na]$^+$, 279 [M–K]$^+$. MS (ESI) m/z: 239 [M–H]$^-$. $^1$H NMR (DMSO-d$_6$): δ 8.43 (d, 1H, J=8.5 Hz), 7.94 (s, 1H), 4.82 (ddd, 1H, J=8.2, 5.4, 2.7 Hz), 3.38 (t, 1H, J=5.4 Hz), 3.02 (dd, 1H, J=5.4, 2.7 Hz), 2.08 (t, 2H, J=7.5 Hz), 1.53-1.42 (m, 2H), 1.33-1.16 (m, 12H), 0.86 (t, 3H, J=7.1 Hz).

Example 24

N-[(3S)-2-Oxoazetidin-3-yl]-undecanamide

Step 1. Preparation of
N-[(3S)-2-oxoazetidin-3-yl]undecanamide

Under nitrogen atmosphere, at 0° C., to a stirred solution of undecanoic acid (0.084 g, 0.45 mmol) in dry CH$_2$Cl$_2$ (4.0 mL), dry Et$_3$N (0.12 mL, 0.90 mmol) was added dropwise. Subsequently TBTU (0.14 g, 0.45 mmol) was added at the same temperature and the resulting reaction mixture was stirred for 30 min. Then [(3S)-2-oxoazetidin-3-yl]-ammonium acetate (0.060 g, 0.41 mmol) was added, and the reaction mixture was left at r.t. for 16 h. The mixture was diluted with CH$_2$Cl$_2$ (15 mL), and washed with sat. NH$_4$Cl solution (2×20 mL), sat. NaHCO$_3$ solution (2×20 mL) and brine (20 mL). The organic layer was dried over Na$_2$SO$_4$, filtered and concentrated to afford a fine powder (0.12 g). Trituration with EtOAc afforded the pure title compound (0.065 g, 62%), as a white solid. R$_t$=2.54 min. MS (ESI) m/z: 255 [M–H]$^+$, 293 [M–K]$^+$. $^1$H NMR (DMSO-d$_6$): δ 8.43 (d, 1H, J=8.3 Hz), 7.94 (s, 1H), 4.82 (ddd, 1H, J=8.3, 5.4, 2.5 Hz), 3.38 (t, 1H, J=5.4 Hz), 3.02 (dd, 1H, J=5.4, 2.5 Hz), 2.08 (t, 2H, J=7.4 Hz), 1.54-1.42 (m, 4H), 1.24 (s, 12H), 0.84 (t, 3H, J=6.4 Hz).

Example 25

5-Phenyl-N-[(3S)-2-oxoazetidin-3-yl]-pentanamide

Step 1. Preparation of
5-phenyl-N-[(3S)-2-oxoazetidin-3-yl]-pentanamide

Under nitrogen atmosphere, at 0° C., to a stirred solution of 5-phenylpentanoic acid (0.067 g, 0.38 mmol) in dry CH$_2$Cl$_2$ (6.0 mL), dry Et$_3$N (0.1 mL, 0.71 mmol) was added dropwise. Subsequently TBTU (0.12 g, 0.38 mmol) was added at the same temperature and the resulting reaction mixture was stirred for 30 min. [(3S)-2-oxoazetidin-3-yl]- ammonium acetate (0.050 g, 0.34 mmol) was then added, and the reaction was left at r.t. for 16 h. The mixture was diluted with $CH_2Cl_2$ (15 mL), washed with sat. $NH_4Cl$ solution (2×20 mL), sat. $NaHCO_3$ solution (2×20 mL) and brine (20 mL). The organic layer was dried over $Na_2SO_4$, filtered and concentrated to afford a fine powder (0.13 g), which after trituration with $Et_2O$ afforded the pure title compound (0.028 g, 33%), as a white solid. $R_t$=1.79 min. MS (ESI) m/z: 247 [M−H]$^+$, 269 [M−Na]$^+$, 285 [M−K]$^+$. MS (ESI) m/z: 245 [M−H]$^−$. $^1$H NMR (DMSO-d$_6$): δ 8.46 (d, 1H, J=8.3 Hz), 7.94 (s, 1H), 7.30-7.23 (m, 2H), 7.21-7.13 (m, 3H), 4.82 (ddd, 1H, J=8.3, 5.4, 2.6 Hz), 3.38 (t, 1H, J=5.4 Hz), 3.02 (dd, 1H, J=5.4, 2.6 Hz), 2.56 (t, 2H, J=7.2 Hz), 2.12 (t, 2H, J=6.8 Hz), 1.60-1.45 (m, 4H).

Example 26

5-Phenyl-N-[(3R)-2-oxoazetidin-3-yl]-pentanamide

Step 1. Preparation of 5-phenyl-N-[(3R)-2-oxoazetidin-3-yl]-pentanamide

Under nitrogen atmosphere, at 0° C., to a solution of 5-phenylpentanoic acid (0.080 g, 0.45 mmol) in dry $CH_2Cl_2$ (4.0 mL), dry $Et_3N$ (0.12 mL, 0.90 mmol) was added dropwise. Subsequently TBTU (0.14 g, 0.45 mmol) was added at the same temperature and the resulting reaction mixture was stirred for 30 min. [(3R)-2-oxoazetidin-3-yl]-ammonium acetate (0.060 g, 0.41 mmol) was then added, and the reaction was left at r.t. for 16 h. The mixture was diluted with $CH_2Cl_2$ (15 mL), washed with sat. $NH_4Cl$ solution (2×15 mL), sat. $NaHCO_3$ solution (2×15 mL) and brine (15 mL). The organic layer was dried over $Na_2SO_4$, filtered and concentrated to afford a fine powder (0.12 g), which after trituration with $Et_2O$ afforded the pure title compound (0.032 g, 33%), as a white solid. $R_t$=1.79 min. MS (ESI) m/z: 247 [M−H]$^+$, 269 [M−Na]$^+$, 285 [M−K]$^+$. MS (ESI) m/z: 245 [M−H]$^−$. $^1$H NMR (DMSO-d$_6$): δ 8.46 (d, 1H, J=8.3 Hz), 7.94 (s, 1H), 7.30-7.23 (m, 2H), 7.21-7.13 (m, 3H), 4.82 (ddd, 1H, J=8.3, 5.4, 2.6 Hz), 3.38 (t, 1H, J=5.4 Hz), 3.02 (dd, 1H, J=5.4, 2.6 Hz), 2.56 (t, 2H, J=7.2 Hz), 2.12 (t, 2H, J=6.8 Hz), 1.60-1.45 (m, 4H).

Example 27

N-Methyl-N-[(3S)-2-Oxoazetidin-3-yl]-nonanamide

Step 1. Preparation of benzyl N-methyl-N-[(3S)-1-(4-methoxyphenyl)-2-oxo-azetidin-3-yl]-carbamate Under nitrogen atmosphere, at 0° C., to a stirred solution of benzyl N-[(3S)-1-(4-methoxyphenyl)-2-oxo-azetidin-3-yl]-carbamate (0.74 g, 2.27 mmol) [compound synthesized as reported by Hanessian et al., Can. J. Chem. 1985, 63, 3613] in dry DMF (15 mL), NaH (95% pure, 0.069 g, 2.72 mmol) was added in one portion, and the resulting suspension was stirred at 0° C. for 30 min. MeI (0.65 g, 4.54 mmol) was then added and stirring was maintained at 0° C. for additional 1 h. The solution was diluted with $Et_2O$ (70 mL) and washed with $H_2O$ (3×70 mL). The organic layer was dried over $Na_2SO_4$, filtered and concentrated to dryness affording the title compound (0.69 g, 90%), which was used in the next step without any further purification. $R_t$=2.52 min. MS (ESI) m/z: 341 [M−H]$^+$, 363 [M−Na]$^+$, 379 [M−K]$^+$. $^1$H NMR (DMSO-d$_6$): δ 7.45-7.21 (m, 7H), 6.99-6.93 (m, 2H), 5.36-5.29 (s, 1H), 5.12 (s, 2H), 3.90 (t, 1H, J=5.9 Hz), 3.76-3.71 (m, 4H), 2.93-2.89 (m, 3H).

Step 2. Preparation of benzyl N-methyl-N-[(3S)-2-oxoazetidin-3-yl]-carbamate

Benzyl N-methyl-N-[(3S)-1-(4-methoxyphenyl)-2-oxoazetidin-3-yl]-carbamate (0.69 g, 2.03 mmol) was suspended in a 1:1 mixture of MeCN/$H_2O$ (86 mL). The solution was cooled to 0° C. and, under vigorous stirring, a solution of CAN (0.48 g, 0.88 mmol) in $H_2O$ (3.0 mL) was added dropwise over 5 min. After additional 10 min, EtOAc (50 mL) and sat. $NaHCO_3$ solution (10 mL) were added to the reaction. After separation of the layers, the organic phase was dried over $Na_2SO_4$, filtered and concentrated to dryness affording the title compound (0.5 g, 92%), which was used in the next step without any further purification. $R_t$=1.72 min. MS (ESI) m/z: =235 [M−H]$^+$, 257 [M−Na]$^+$, 273 [M−K]$^+$. $^1$H NMR (DMSO-d$_6$): δ 8.10 (s, 1H), 7.41-7.29 (m, 5H), 5.25-5.16 (bs, 1H), 5.15-5.05 (m, 2H), 3.38 (t, 1H, J=5.7 Hz), 3.23 (dd, 1H, J=5.9, 2.6 Hz), 2.84 (s, 3H).

Step 3. Preparation of methyl-[(3S)-2-oxoazetidin-3-yl]-ammonium acetate

A 0.05 M THF solution (18 mL) of benzyl N-methyl-N-[(3S)-2-oxoazetidin-3-yl]-carbamate (0.20 g, 0.86 mmol) was passed through the H-Cube® hydrogenator flow reactor, provided with a 10% Pd/C cartridge (flow rate: 1.0 mL/min; P=1.0 bar; T=35° C.). The outcoming solution was immediately trapped into a solution of AcOH (0.054 mL, 0.94 mmol) in EtOAc (4.0 mL) then concentrated to dryness, affording the title compound (0.1 g, 78%), which was used in the next step without any further purification. $^1$H NMR (DMSO-d$_6$): δ 7.76 (bs, 1H), 4.00 (ddd, 1H, J=5.2, 2.5, 1.6 Hz), 3.21 (t, 1H, J=5.2 Hz), 2.98 (dd, 1H, J=5.2, 2.5 Hz), 2.28 (s, 3H), 1.91 (s, 3H).

Step 4. Preparation of N-methyl-N-[(3S)-2-oxoazetidin-3-]-nonanamide

Under nitrogen atmosphere, at 0° C., to a stirred suspension of methyl-[(3S)-2-oxoazetidin-3-yl]-ammonium acetate (0.05 g, 0.31 mmol) in dry $CH_2Cl_2$ (3.0 mL), dry $Et_3N$ (0.091 mL, 0.66 mmol) and commercially available nonanoyl chloride (0.076 mL, 0.34 mmol) were added dropwise. The resulting mixture was stirred at r.t. for 6 h, then diluted with $CH_2Cl_2$ (20 mL) and sequentially washed with sat. $NH_4Cl$ solution (2×10 mL), sat. $NaHCO_3$ solution (2×10 mL) and brine (10 mL). The organic layer was dried over $Na_2SO_4$, filtered and concentrated to dryness giving a crude product (0.145 g). Purification by preparative HPLC afforded the pure title compound (0.027 g, 33%), as 1:1 mixture of two rotamers, as an oil. $R_t$=2.31 min. MS (ESI) m/z: 241 [M−H]$^+$, 263 [M−Na]$^+$, 279 [M−K]$^+$. $^1$H NMR (DMSO-d$_6$): δ 8.14 (s, 1H), 8.07 (s, 1H), 5.50-545 (m, 1H), 5.33-5.27 (m, 1H), 3.43 (t, 1H, J=5.8 Hz), 3.35 (t, 1H, J=5.8 Hz), 3.22 (dd, 1H, J=5.8, 2.5 Hz), 3.17 (dd, 1H, J=5.8, 2.5 Hz), 2.90 (s, 3H), 2.74 (s, 3H), 2.42-2.23 (m, 4H), 1.53-1.40 (m, 4H), 1.33-1.16 (m, 20H), 0.86 (t, 6H, J=7.0 Hz).

Preparation of [(2S,3S)-2-methyl-4-oxo-azetidin-3-yl]-ammonium toluene-4-sulfonate Step 1. Preparation of benzyl-N-[(1S,2R)-2-hydroxy-1-(methoxycarbamoyl)-propyl]-carbamate To a suspension of commercially available N-carbobenzyloxy-L-threonine (3.39 g, 13.4 mmol) in dry THF (100 mL), methoxyamine hydrochloride (3.26 g, 40.2 mmol), EDC (7.7 g, 40.2 mmol) and $H_2O$ (30 mL) were sequentially added. The biphasic solution was stirred at r.t. for 3 h, and then sat. NaCl solution was added. The crude mixture was extracted with EtOAc (4×100 mL) and the combined organic extracts were dried over $Na_2SO_4$ and concentrated to dryness to afford a solid residue (3.60 g), as a mixture (75:25 ratio) of the title compound and unreacted starting material, which was used in the next step without any further purification. $R_t$=1.50 min; MS (ESI) m/z: 283 [M−H]$^+$; 305 [M−Na]$^+$; (ESI) m/z: 281 [M−H]$^−$. $^1$H NMR (DMSO-d$_6$): δ 11.19 (s, 1H), 7.42-7.27 (m, 5H), 7.02 (d, 1H, J=8.5 Hz), 5.05 (d, 1H, J=12.0 Hz), 5.01 (d, 1H, J=12.0 Hz), 3.91-3.78 (m, 1H), 3.74 (dd, 1H, J=8.5, 5.3 Hz), 3.57 (s, 3H), 1.04 (d, 3H, J=6.3 Hz).

Step 2. Preparation of [(1S,2R)-2-(benzyloxycarbonylamino)-3-(methoxyamino)-1-methyl-3-oxo-propyl]-methanesulfonate The crude mixture (3.40 g) containing benzyl-N-[(1S,2R)-2-hydroxy-1-(methoxycarbamoyl)-propyl]-carbamate (2.64 g, 7.34 mmol) was dissolved in dry pyridine (30 mL) and cooled to −5° C. Methanesulfonyl chloride (1.62 g, 14.68 mmol) was added over a period of 15 min, the mixture was stirred for 3 h at 0° C., and then poured into iced $H_2O$ (50 mL). The aqueous solution was adjusted to pH 4 with 2.0 N HCl solution, washed with sat. NaCl solution and extracted with EtOAc (4×20 mL). The combined organic layer was dried over $Na_2SO_4$ and concentrated to dryness to afford a solid residue which was purified by column chromatography using a Teledyne ISCO apparatus (Cy/TBME from 100:0 to 0:100) to afford the pure title compound (2.38 g, 73%), as white solid. $R_t$=1.78 min; MS (ESI) m/z: 361 [M−H]$^+$, 399 [M−K]$^+$, (ESI) m/z: 359 [M−H]$^−$. $^1$H NMR (DMSO-d$_6$): δ 11.55 (s, 1H), 7.77 (d, 1H, J=9.41 Hz), 7.47-7.25 (m, 5H), 5.07 (q, 2H, J=12.60 Hz), 4.83 (t, 1H, J=6.34 Hz), 4.14 (dd, 1H, J=9.41, 6.34 Hz), 3.60 (s, 3H), 3.09 (s, 3H), 1.31 (d, 3H, J=6.34 Hz).

Step 3. Preparation of benzyl-N-[(2S,3S)-1-methoxy-2-methyl-4-oxo-azetidin-3-yl]-carbamate To a refluxing (90° C.) slurry of powdered $K_2CO_3$ (2.44 g, 17.67 mmol) in acetone (100 mL), a solution of [(1S,2R)-2-(benzyloxycarbonylamino)-3-(methoxyamino)-1-methyl-3-oxo-propyl]-methanesulfonate (1.59 g, 4.42 mmol) in acetone (60 mL) was added. The resulting suspension was stirred at 100° C. for 3 h. Upon cooling, the thick slurry was filtered through celite, and the collected solid was extracted with EtOAc (50 mL). After being washed sequentially with 1.0 N HCl solution (60 mL), sat. $NaHCO_3$ solution (60 mL) and brine (60 mL), the organic solution was dried over $Na_2SO_4$ and concentrated to dryness. The crude product was purified using a Teledyne ISCO apparatus (Cy/TBME from 100:0 to 20:80) to afford the pure title compound (0.91 g, 78%). $R_t$=1.94 min; MS (ESI) m/z: 265 [M−H]$^+$, 287 [M−Na]$^+$. $^1$H NMR (DMSO-d$_6$): δ 8.03 (d, 1H, J=8.12 Hz), 7.45-7.29 (m, 5H), 5.06 (s, 2H), 4.09 (dd, 1H, J=8.12, 2.06 Hz), 3.95-3.84 (m, 1H), 3.74 (s, 3H), 1.39-1.29 (m, 3H).

Step 4. Preparation of benzyl-N-[(2S,3S)-2-methyl-4-oxo-azetidin-3-yl]-carbamate To a stirred mixture of benzyl-N-[(2S,3S)-1-methoxy-2-methyl-4-oxo-azetidin-3-yl]-carbamate (1.07 g, 4.0 mmol) in dry THF (25 mL), a 0.5 M solution of $SmI_2$ in THF (162 mL, 15.2 mmol) was dropwise added via cannula. The reaction mixture was left to stir at r.t. for 30 min until complete disappearance of starting material. The crude mixture was diluted with EtOAc and washed twice with a 10% $Na_2S_2O_3$ solution and brine. The organic fraction was dried over $Na_2SO_4$, filtered and concentrated to dryness to give a crude product. Purification by column chromatography using a Teledyne ISCO apparatus (Cy/MTBE from 100:0 to 0:100) afforded the pure title compound (0.57 g, 60%), as a white sticky solid. $R_t$=1.67 min. $^1$H NMR (DMSO-d$_6$): δ 8.08 (s, 1H), 7.96 (d, 1H, J=8.6 Hz), 7.42-7.28 (m, 5H), 5.05 (d, 1H, J=12.2 Hz), 5.01 (d, 1H, J=12.2 Hz), 4.11 (dd, 1H, J=8.6, 2.3 Hz), 3.56-3.48 (m, 1H), 1.24 (d, 3H, J=6.1 Hz).

Step 5. Preparation of [(2S,3S)-2-methyl-4-oxo-azetidin-3-yl]-ammonium toluene-4-sulfonate To a stirred mixture of benzyl-N-[(2S,3S)-2-methyl-4-oxo-azetidin-3-yl]-carbamate (0.44 g, 1.90 mmol) in EtOH (37 mL), previously submitted to few cycles of vacuum/argon flow, commercially available cyclohexadiene (1.79 mL, 18.99 mmol) and 10% Pd on charcoal (0.44 g) were added. The reaction mixture was left to react at r.t. for 2 h, diluted with EtOAc and filtered over a pad of Celite into a p-TsOH (0.38 g, 1.99 mmol) solution in EtOAc (37 mL). The solution was concentrated to dryness to give the pure title compound (0.54 g, quant.), as a white fluffy solid. $^1$H NMR (DMSO-d$_6$): δ 8.61 (s, 3H), 8.56 (s, 1H), 7.49 (d, 2H, J=7.9 Hz), 7.12 (d, 2H, J=7.9 Hz), 4.01 (s, 1H), 3.65-3.58 (m, 1H), 2.29 (s, 3H), 1.29 (d, 3H, J=6.1 Hz).

Example 28

N-[(2S,3S)-2-methyl-4-oxo-azetidin-3-yl]-nonanamide

Under nitrogen atmosphere, at 0° C., to a stirred suspension of [(2S,3S)-2-methyl-4-oxo-azetidin-3-yl]-ammonium toluene-4-sulfonate (0.85 g, 0.31 mmol) in dry $CH_2Cl_2$ (4 mL), dry $Et_3N$ (0.095 mL, 0.69 mmol) and commercially available nonanoyl chloride (0.06 mL, 0.34 mmol) were added dropwise. The resulting reaction mixture was stirred at r.t. for 15 h and concentrated to dryness to give a crude product. Purification by column chromatography using a Teledyne ISCO apparatus (Cy/EtOAc from 100:0 to 0:100) afforded the pure title compound (0.04 g, 52%), as a white solid. $R_t$=2.24 min. MS (ESI) m/z: 241 [M−H]$^+$, 263 [M−Na]$^+$, 279 [M−K]$^+$. MS (ESI) m/z: 239 [M−H]$^−$. $^1$H NMR (DMSO-d$_6$): δ 8.43 (d, J=8.14 Hz, 1H), 8.10 (s, 1H), 4.29 (dd, J=2.16, 8.14 Hz, 1H), 3.44 (dq, J=2.16, 6.09 Hz, 1H), 2.08 (t, J=7.43 Hz, 2H), 1.48 (p, J=7.00 Hz, 2H), 1.33-1.16 (m, 13H), 0.86 (t, J=6.69 Hz, 3H).

Example 29

N-[(2S,3S)-2-methyl-4-oxo-azetidin-3-yl]-3-(4-phenylphenyl)-propanamide

Under nitrogen atmosphere, at 0° C., to a solution of 3-(4-phenylphenyl)-propanoic acid (0.074 g, 0.33 mmol) in a dry $CH_2Cl_2$ (5.0 mL), dry $Et_3N$ (0.09 mL, 0.68 mmol) was added dropwise. Then, TBTU (0.11 g, 0.34 mmol) was added at the same temperature and the resulting reaction mixture was stirred for 30 min. [(2S,3S)-2-methyl-4-oxo-azetidin-3-yl]-ammonium toluene-4-sulfonate (0.085 g, 0.31 mmol) was then added, and the reaction mixture was stirred at r.t. for 15 h. The crude mixture was concentrated to dryness to give a crude product. Purification by column chromatography using a Teledyne ISCO apparatus (Cy/EtOAc from 100:0 to 0:100) and trituration with $Et_2O$ afforded the pure title compound (0.07 g, 70%), as a white solid. $R_t$=2.16 min; MS (ESI) m/z: 309 $[M-H]^+$, 331 $[M-Na]^+$, 347 $[M-K]^+$. MS (ESI) m/z: 307 $[M-H]^-$. $^1H$ NMR (DMSO-d6): δ 8.54 (d, J=8.10 Hz, 1H), 8.11 (s, 1H), 7.65-7.61 (m, 2H), 7.59-7.54 (m, 2H), 7.48-7.42 (m, 2H), 7.37-7.27 (m, 3H), 4.32 (dd, J=2.19, 8.10 Hz, 1H), 3.46-3.38 (m, 1H), 2.86 (t, J=7.74 Hz, 2H), 2.45 (t, 2H), 1.24 (d, J=6.06 Hz, 3H).

Example 30

7-Cyclohexyl-N-[(3S)-2-oxoazetidin-3-yl]-heptanamide

Step 1. Preparation of 5-cyclohexylpentanol

Under nitrogen atmosphere, at 0° C., to a suspension of $LiAlH_4$ (2.0 M THF solution, 10.8 mL, 21.74 mmol) in dry $Et_2O$ (60 mL), 5-cyclohexylpentanoic acid (1.0 g, 5.43 mmol) in dry $Et_2O$ (10 mL) was added dropwise. The resulting reaction mixture was stirred at r.t. for 1 h, and then cooled to 0° C. $H_2O$ (0.5 mL) was slowly and cautiously added, followed by 3.0 M KOH solution (0.5 mL) and additional $H_2O$ (2.2 mL). The mixture was stirred at 0° C. for 1 h and then filtered off. The organic layer was dried over $Na_2SO_4$, filtered and concentrated to dryness, affording the title compound (1.02 g, quant.), which was used in the next step without any further purification. $^1H$ NMR (DMSO-d6): δ 4.30 (s, 1H), 3.37 (t, 2H, J=6.3 Hz), 1.71-1.56 (m, 5H), 1.45-1.36 (m, 2H), 1.30-1.07 (m, 10H), 0.90-0.78 (m, 2H).

Step 2. Preparation of 5-cyclohexylpentanal

Under nitrogen atmosphere, at 0° C., to a stirred solution of oxalyl chloride (0.66 mL, 7.80 mmol) in dry $CH_2Cl_2$ (30 mL), DMSO (0.51 mL, 7.20 mmol) in dry $CH_2Cl_2$ (10.0 mL) was added dropwise. After 15 min, a solution of 5-cyclohexylpentanol (1.02 g, 6.00 mmol) in dry $CH_2Cl_2$ (10.0 mL) was slowly added and the resulting reaction mixture was stirred at −78° C. for 1 h. Then $Et_3N$ (2.38 mL, 18.0 mmol) was added dropwise. The resulting solution was warmed up to r.t., and after evaporation of the solvents, the crude mixture was taken up in $Et_2O$ (40 mL) and washed with sat. $NH_4Cl$ solution (2×30 mL). The organic layer was dried over $Na_2SO_4$, filtered and concentrated to dryness giving the title compound (1.02 g, quant.), which was used in the next step without any further purification. $^1H$-NMR (DMSO-d6): δ 9.66 (t, 1H, J=1.6 Hz), 2.41 (td, 2H, J=7.3, 1.6 Hz), 1.71-1.57 (m, 5H), 1.50 (p, 2H, J=7.5 Hz), 1.32-1.08 (m, 8H), 0.91-0.78 (t, 2H).

Step 3. Preparation of ethyl (E)-7-cyclohexylhept-2-enoate

Under nitrogen atmosphere, at 0° C., to a stirred suspension of NaH (95% pure, 0.169 g, 6.65 mmol) in dry THF (50 mL), a solution of triethyl phosphonoacetate (1.32 mL, 6.65 mmol) in dry THF (10.0 mL) was added dropwise. The resulting mixture was stirred for 15 min, then a solution of 5-cyclohexylpentanal (1.02 g, 6.05 mmol) in dry THF (10.0 mL) was added dropwise to the reaction mixture. After stirring for 16 h, $H_2O$ (20 mL) and $Et_2O$ (30.0 mL) were sequentially added, and the solution was stirred for additional 15 min. The organic phase was separated and dried over $Na_2SO_4$, filtered and concentrated to dryness, giving a crude product. Purification by typical silica gel flash chromatography (Cy/EtOAc, from 100:0 to 83:17) afforded the pure title compound (0.900 g, 77% brsm), as an oil. $R_t$=1.62 min. $^1H$ NMR (DMSO-d6): δ 6.88 (dt, 1H, J=15.5, 7.0 Hz), 5.84 (dt, 1H, J=15.5, 1.6 Hz), 4.11 (q, 2H, J=7.2 Hz), 2.19 (qd, 2H, J=7.2, 1.2 Hz), 1.71-1.56 (m, 6H), 1.44-10.5 (m, 12H), 0.91-0.78 (m, 2H).

Step 4. Preparation of ethyl 7-cyclohexylheptanoate

A 0.05 M solution of ethyl (E)-7-cyclohexylhept-2-enoate (0.25 g, 1.05 mmol) in EtOH (20 mL) was passed through the H-Cube® hydrogenator flow reactor, provided with a 10% Pd/C cartridge (flow rate: 1.0 mL/min; P=20 bars; T=45° C.). Evaporation of solvent afforded the title compound (0.233 g, 92%), as a colorless liquid, which was used in the next step without any further purification. $^1H$ NMR (DMSO-d6): δ 4.05 (q, 2H, J=7.2 Hz), 2.26 (t, 2H, J=7.2 Hz), 1.70-1.56 (m, 6H), 1.55-1.46 (m, 2H), 1.32-1.07 (m, 14H), 0.91-0.78 (m, 2H).

Step 5. Preparation of ethyl 7-cyclohexylheptanoic acid

Under vigorous stirring, to a solution of ethyl 7-cyclohexylheptanoate (0.23 g, 0.96 mmol) in a 1:1:1 mixture of $THF/MeOH/H_2O$ (6.0 mL), LiOH (0.092 g, 3.83 mmol) was added in one portion. After 1 h at the same temperature, evaporation of the solvents gave a crude mixture which was diluted with $H_2O$ (5.0 mL) and treated with 0.5 M $H_2SO_4$ solution until pH 3. After extraction with EtOAc (3×25 mL), the organic layer was dried over $Na_2SO_4$, filtered and concentrated to dryness, affording the crude title compound (0.21 g), as yellowish oil, which was used in the next step without any further purification. $^1H$-NMR (DMSO-d6): δ 11.96 (s, 1H), 2.19 (t, 2H, J=7.5 Hz), 1.71-1.55 (m, 5H), 1.53-1.44 (m, 2H), 1.31-1.08 (m, 12H), 0.91-0.78 (m, 2H).

Step 6. Preparation of 6-cyclohexyl-N-[(3S)-2-oxoazetidin-3-yl]-hexanamide

Under nitrogen atmosphere, at 0° C., to a stirred solution of 7-cyclohexylheptanoic acid (0.08 g, 0.38 mmol) in dry $CH_2Cl_2$ (6.0 mL), dry $Et_3N$ (0.100 mL, 0.75 mmol) was added dropwise. Subsequently TBTU (0.12 g, 0.38 mmol) was added at the same temperature and the resulting reaction mixture was stirred for 30 min. Then [(3S)-2-oxoazetidin-3-yl]-ammonium acetate (0.050 g, 0.34 mmol) was added, and the reaction mixture was left at r.t. for 16 h. The mixture was diluted with $CH_2Cl_2$ (15 mL), and washed with sat. $NH_4Cl$ solution (2×20 mL), sat. $NaHCO_3$ solution (2×20 mL) and brine (20 mL). The organic layer was dried over $Na_2SO_4$, filtered and concentrated to afford a fine powder (0.10 g). Trituration with $Et_2O$ afforded the pure title compound (0.033 g, 35%), as a white solid. $R_t$=2.73 min. MS (ESI) m/z: 281 $[M-H]^+$, 303 $[M-Na]^+$, 319 $[M-K]^+$. MS (ESI) m/z: 279 $[M-H]^-$. $^1H$ NMR (DMSO-d6): δ 8.42 (d, 1H, J=8.3 Hz), 7.94 (s, 1H), 4.85-4.79 (m, 1H), 3.38 (t, 1H, J=5.3 Hz), 3.02 (dd, 1H, J=5.3, 2.7 Hz), 2.08 (t, 2H, J=7.4 Hz), 1.70-1.55 (m, 5H), 1.53-1.42 (m, 2H), 1.28-1.07 (m, 12H), 0.89-0.77 (m, 2H).

Example 31

6-Phenyl-N-[(3S)-2-oxoazetidin-3-yl]-hexanamide

Step 1. Preparation of 6-phenyl-N-[(3S)-2-oxoazetidin-3-yl]-hexanamide

Under nitrogen atmosphere, at 0° C., to a solution of 6-phenylhexanoic acid (0.084 mL, 0.45 mmol) in dry $CH_2Cl_2$ (3.0 mL), dry $Et_3N$ (0.12 mL, 0.90 mmol) was added dropwise. Subsequently TBTU (0.144 g, 0.45 mmol) was added at the same temperature and the resulting reaction mixture was stirred for 30 min. Then [(3S)-2-oxoazetidin-3-yl]-ammonium acetate (0.060 g, 0.41 mmol) was added and the reaction solution was stirred at r.t. for 16 h. The mixture was diluted with $CH_2Cl_2$ (60 mL) and sequentially washed with sat. $NH_4Cl$ solution (2×15 mL), sat. $NaHCO_3$ solution (2×15 mL) and brine (20 mL). The organic layer was dried over $Na_2SO_4$, filtered and concentrated to dryness giving crude product (0.190 g). Trituration with $Et_2O$ afforded the pure title compound (0.032 g, 30%), as a white solid. $R_t$=1.98 min. MS (ESI) m/z: 261 [M−H]$^+$, 283 [M−Na]$^+$, 299 [M−K]$^+$. $^1$H NMR (DMSO-d$_6$): δ 8.44 (d, 1H, J=8.2 Hz), 7.94 (bs, 1H), 7.29-7.23 (m, 2H), 7.20-7.13 (m, 3H), 4.82 (ddd, 1H, J=8.2, 5.4, 2.5 Hz), 3.38 (t, 1H, J=5.4 Hz), 3.01 (dd, 1H, J=5.4, 2.5 Hz), 2.58-2.52 (m, 2H), 2.08 (t, 2H, J=7.4 Hz), 1.60-1.42 (m, 4H), 1.32-1.20 (m, 2H).

Example 32

4-Phenyl-N-[(3S)-2-oxoazetidin-3-yl]-butanamide

Step 1. Preparation of 4-phenyl-N-[(3S)-2-oxoazetidin-3-yl]-butanamide

Under nitrogen atmosphere, at 0° C., to a solution of 4-phenylbutanoic acid (0.074 g, 0.45 mmol) in dry $CH_2Cl_2$ (3.0 mL), dry $Et_3N$ (0.12 mL, 0.90 mmol) was added dropwise. Subsequently TBTU (0.144 g, 0.45 mmol) was added at the same temperature and the resulting reaction mixture was stirred for 30 min. Then [(3S)-2-oxoazetidin-3-yl]-ammonium acetate (0.06 g, 0.41 mmol) was added and the reaction solution was stirred at r.t. for 16 h. The mixture was diluted with $CH_2Cl_2$ (60 mL) and sequentially washed with sat. $NH_4Cl$ solution (2×15 mL), sat. $NaHCO_3$ solution (2×15 mL) and brine (20 mL). The organic layer was dried over $Na_2SO_4$, filtered and concentrated to dryness giving crude product (0.170 g). Purification by silica gel flash chromatography using a Teledyne ISCO apparatus (Cy/EtOAc from 100:0 to 10:90) afforded the pure title compound (0.032 g, 34%), as a white solid. $R_t$=1.63 min. MS (ESI) m/z: 233 [M−H]$^+$, 250 [M−Na]$^+$, 271 [M−K]$^+$. $^1$H NMR (DMSO-d$_6$): δ 8.46 (d, 1H, J=8.4 Hz,), 7.94 (bs, 1H), 7.33-7.24 (m, 2H), 7.20-7.16 (m, 3H), 4.82 (ddd, 1H, J=8.4, 5.4, 2.5 Hz), 3.39 (t, 1H, J=5.4 Hz), 3.03 (dd, 1H, J=5.4, 2.5 Hz), 2.55 (t, 2H, J=7.5 Hz), 2.12 (t, 2H, J=7.5 Hz), 1.79 (p, 2H, J=7.5 Hz).

Example 33

4-Butyl-N-[(3S)-2-oxoazetidin-3-yl]-benzamide

Step 1. Preparation of 4-butyl-N-[(3S)-2-oxoazetidin-3-yl]-benzamide

Under nitrogen atmosphere, at 0° C., to a solution of 4-butylbenzoic acid (0.080 g, 0.45 mmol) in dry $CH_2Cl_2$ (3.0 mL), dry $Et_3N$ (0.12 mL, 0.90 mmol) was added dropwise. Subsequently TBTU (0.144 g, 0.45 mmol) was added at the same temperature and the resulting reaction mixture was stirred for 30 min. Then [(3S)-2-oxoazetidin-3-yl]-ammonium acetate (0.060 g, 0.41 mmol) was added and the reaction solution was stirred at r.t. for 16 h. The mixture was diluted with $CH_2Cl_2$ (60 mL) and sequentially washed with sat. $NH_4Cl$ solution (2×15 mL), sat. $NaHCO_3$ solution (2×15 mL) and brine (20 mL). The organic layer was dried over $Na_2SO_4$, filtered and concentrated to dryness giving crude product (0.140 g). Trituration with $Et_2O$ afforded the pure title compound (0.029 g, 29%), as a white solid. $R_t$=2.07 min. MS (ESI) m/z: 247 [M−H]$^+$, 269 [M−Na]$^+$, 285 [M−K]$^+$. $^1$H NMR (DMSO-d$_6$): δ 8.99 (d, 1H, J=8.4 Hz,), 8.02 (bs, 1H), 7.78 (d, 2H, J=8.2 Hz), 7.29 (d, 2H, J=8.2 Hz), 5.05 (ddd, 1H, J=8.4, 5.4, 2.6 Hz,), 3.46 (t, 1H, J=5.4 Hz), 3.24 (dd, 1H, J=5.4, 2.6 Hz), 2.63 (t, 2H, J=7.5 Hz), 1.63-1.50 (m, 2H), 1.37-1.20 (m, 2H), 0.89 (t, 3H, J=7.4 Hz).

Example 34

(1r,4R)-4-butyl-N—((S)-2-oxoazetidin-3-yl)cyclohexanecarboxamide

Step 1. Preparation of (1r, 4R)-4-butyl-N—((S)-2-oxoazetidin-3-yl)cyclohexanecarboxamide Under nitrogen atmosphere, to a cooled (0° C.) suspension of commercially available 4-butylcyclohexanecarboxylic acid (0.061 g, 0.34 mmol) in a 3:1 mixture of dry $CH_2Cl_2$/DMF (3.3 mL), dry $Et_3N$ (0.090 mL, 0.68 mmol) was added dropwise. Subsequently TBTU (0.109 g, 0.34 mmol) was added at the same temperature and the resulting reaction mixture was stirred for 30 min. Then [(3S)-2-oxoazetidin-3-yl]-ammonium acetate (0.045 g, 0.31 mmol) was added and the reaction solution was stirred at r.t. for 16 h. The mixture was diluted with $CH_2Cl_2$ (40 mL) and sequentially washed with sat. $NH_4Cl$ solution (2×10 mL), sat. $NaHCO_3$ solution (2×10 mL) and brine (15 mL). The organic layer was dried over $Na_2SO_4$, filtered and concentrated to dryness giving crude product (0.12 g). Trituration with EtOAc afforded the pure title compound (0.025 g, 32%), as a white solid. $R_t$=2.33 min. MS (ESI) m/z: 253 [M−H]$^+$, 270 [M−NH$_4$]$^+$, 291 [M−K]$^+$. $^1$H NMR (DMSO-d$_6$): δ 8.36 (d, 1H, J=8.4 Hz), 7.93 (bs, 1H), 4.82 (ddd, 1H, J=8.4, 5.4, 2.5 Hz), 3.37 (t, 1H, J=5.4 Hz), 3.01 (dd, 1H, J=5.4, 2.5 Hz), 2.06-2.02 (m, 1H), 1.74-1.70 (m, 4H), 1.40-1.20 (m, 6H), 1.19-1.11 (m, 3H), 0.89-0.86 (m, 5H).

Example 35

N-[(3S)-2-oxoazetidin-3-yl]-2-(4-propylphenyl)acetamide

Step 1. Preparation of N-[(3S)-2-oxoazetidin-3-yl]-2-(4-propylphenyl)acetamide Under nitrogen atmosphere, to a cooled (0° C.) suspension of commercially available 2-(4-propylphenyl) acetic acid (0.061 g, 0.34 mmol) in a 3:1 mixture of dry $CH_2Cl_2$/DMF (3.3 mL), dry $Et_3N$ (0.090 mL, 0.68 mmol) was added dropwise. Subsequently TBTU (0.109 g, 0.34 mmol) was added at the same temperature and the resulting reaction mixture was stirred for 30 min. Then [(3S)-2-oxoazetidin-3-yl]-ammonium acetate (0.045 g, 0.31 mmol) was added and the reaction solution was stirred at r.t. for 16 h. The mixture was diluted with CH$_2$Cl$_2$ (40 mL) and sequentially washed with sat. NH$_4$Cl solution (2×10 mL), sat. NaHCO$_3$ solution (2×10 mL) and brine (15 mL). The organic layer was dried over Na$_2$SO$_4$, filtered and concentrated to dryness giving crude product (0.13 g). Trituration with EtOAc afforded the pure title compound (0.028 g, 37%), as a white solid. R$_t$=1.95 min. MS (ESI) m/z: 247 [M−H]$^+$, 264 [M−NH$_4$]$^+$, 285 [M−K]$^+$. $^1$H NMR (DMSO-d$_6$): δ 8.71 (d, 1H, J=8.2 Hz), 7.97 (bs, 1H), 7.15 (d, 2H, J=8.2 Hz), 7.10 (d, 2H, J=8.2 Hz), 4.82 (ddd, 1H, J=8.2, 5.4, 2.5 Hz), 3.40-3.37 (m, 3H), 3.03 (dd, 1H, J=5.4, 2.5 Hz), 2.55-2.53 (m, 2H), 1.56 (h, 2H, J=7.4 Hz), 0.88 (t, 3H, J=7.4 Hz).

Example 36

(2R)-2-methyl-N-[(3S)-2-oxoazetidin-3-yl]nonanamide and (2S)-2-methyl-N-[(3S)-2-oxoazetidin-3-yl]nonanamide Step 1. Preparation of (2R)-2-methyl-N-[(3S)-2-oxoazetidin-3-yl]nonanamide and (2S)-2-methyl-N-[(3S)-2-oxoazetidin-3-yl]nonanamide Under nitrogen atmosphere, to a cooled (0° C.) suspension of commercially available 2-methylnonanoic acid (0.059 g, 0.34 mmol) in a 3:1 mixture of dry CH$_2$Cl$_2$/DMF (3.3 mL), dry Et$_3$N (0.090 mL, 0.68 mmol) was added dropwise. Subsequently TBTU (0.109 g, 0.34 mmol) was added at the same temperature and the resulting reaction mixture was stirred for 30 min. Then [(3S)-2-oxoazetidin-3-yl]-ammonium acetate (0.045 g, 0.31 mmol) was added and the reaction solution was stirred at r.t. for 16 h. The mixture was diluted with CH$_2$Cl$_2$ (40 mL) and sequentially washed with sat. NH$_4$Cl solution (2×10 mL), sat. NaHCO$_3$ solution (2×10 mL) and brine (15 mL). The organic layer was dried over Na$_2$SO$_4$, filtered and concentrated to dryness giving crude product (0.12 g). Purification by silica gel flash chromatography using a Teledyne ISCO apparatus (Cy/EtOAc from 90:10 to 0:100) afforded the pure title compound (0.024 g, 32%), as a mixture (1:1 ratio) of isomers, as a colorless oil. R$_t$=2.28 min. MS (ESI) m/z: 241 [M−H]$^+$, 258 [M-NH$_4$]$^+$, 279 [M−K]$^+$. $^1$H NMR (DMSO-d$_6$): δ 8.41 (t, 2H, J=8.0 Hz), 7.94 (bs, 2H), 4.85-4.78 (m, 2H), 3.44-3.36 (m, 2H), 3.01 (ddd, 2H, J=7.7, 5.2, 2.7 Hz), 2.30-2.15 (m, 2H), 1.50-1.44 (m, 2H), 1.23 (s, 22H), 0.99-0.97 (m, 6H), 0.85 (t, 6H, J=6.8 Hz).

Example 37

2,2-dimethyl-N-[(3S)-2-oxoazetidin-3-yl]nonanamide

Step 1. Preparation of 2,2-dimethyl-N-[(3S)-2-oxoazetidin-3-yl]nonanamide

Under nitrogen atmosphere, to a cooled (0° C.) suspension of commercially available 2,2-dimethylnonanoic acid (0.064 g, 0.34 mmol) in a 3:1 mixture of dry CH$_2$Cl$_2$/DMF (3.3 mL), dry Et$_3$N (0.090 mL, 0.68 mmol) was added dropwise. Subsequently TBTU (0.109 g, 0.34 mmol) was added at the same temperature and the resulting reaction mixture was stirred for 30 min. Then [(3S)-2-oxoazetidin-3-yl]-ammonium acetate (0.045 g, 0.31 mmol) was added and the reaction solution was stirred at r.t. for 16 h. The mixture was diluted with CH$_2$Cl$_2$ (40 mL) and sequentially washed with sat. NH$_4$Cl solution (2×10 mL), sat. NaHCO$_3$ solution (2×10 mL) and brine (15 mL). The organic layer was dried over Na$_2$SO$_4$, filtered and concentrated to dryness giving crude product (0.110 g). Purification by preparative HPLC afforded the pure title compound (0.026 g, 33%), as a colorless oil. R$_t$=2.47 min. MS (ESI) m/z: 255 [M−H]$^+$, 272 [M−NH$_4$]$^+$, 277 [M−Na]$^+$. $^1$H NMR (DMSO-d$_6$) δ 8.01 (d, 1H, J=8.4 Hz), 7.88 (bs, 1H), 4.79 (ddd, 1H, J=8.3, 5.4, 2.8 Hz), 3.34 (t, 1H, J=5.4 Hz), 3.09 (dd, 1H, J=5.4, 2.8 Hz), 1.45-1.36 (m, 2H), 1.29-1.07 (m, 10H), 1.04 (s, 6H), 0.84 (t, 3H, J=6.9 Hz).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:
1. A compound having the structure of Formula I:

(I)

wherein:
R$^1$ and R$^2$ are each independently selected from the group consisting of hydrogen, alkyl, aryl, cycloalkyl, arylalkyl, and cycloalkylalkyl;
or R$^1$ and R$^2$ form a cycloalkyl substituent together with the carbon to which they are attached;
R$^3$ is selected from the group consisting of hydrogen and alkyl;
wherein R$^4$-R$^5$-R$^6$ is an alkyl selected from the group consisting of unsubstituted octyl, unsubstituted nonyl, unsubstituted decyl, methyl substituted with an unsubstituted cyclohexyl, ethyl substituted with an unsubstituted cyclohexyl, propyl substituted with an unsubstituted cyclohexyl, butyl substituted with an unsubstituted cyclohexyl, pentyl substituted with an unsubstituted cyclohexyl, hexyl substituted with an unsubstituted cyclohexyl, heptyl substituted with an unsubstituted cyclohexyl, octyl substituted with an unsubstituted cyclohexyl, nonyl substituted with an unsubstituted cyclohexyl and docyl substituted with an unsubstituted cyclohexyl;
or a pharmaceutically acceptable salt or ester thereof.

2. A compound of claim 1, having the structure:

(III)

3. A compound of claim 1, wherein R$^1$ and R$^2$ are both hydrogen.
4. A compound of claim 1, wherein R$^1$ is hydrogen and R$^2$ is methyl.
5. A compound of claim 1, wherein the compound is selected from the group consisting of 6. A pharmaceutical composition comprising a compound of claim 1, or a pharmaceutically acceptable salt thereof, and a pharmaceutically acceptable excipient, carrier or diluent.

7. A compound of claim 1, wherein the compound is or a pharmaceutically acceptable salt thereof.

8. A compound of claim 1, wherein the compound is or a pharmaceutically acceptable salt thereof.

* * * * *

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 1
gaccatgctg ggccgtagt                                               19

<210> SEQ ID NO 2
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 2
ccagcctata caagggtct                                               19
```